(12) United States Patent
Smith

(10) Patent No.: US 9,273,296 B2
(45) Date of Patent: Mar. 1, 2016

(54) MEGANUCLEASE VARIANTS CLEAVING A DNA TARGET SEQUENCE FROM A GLUTAMINE SYNTHETASE GENE AND USES THEREOF

(75) Inventor: Julianne Smith, Le Plessis Robinson (FR)

(73) Assignee: CELLECTIS, Romainville (FR)

( * ) Notice: Subject to any disclaimer, the term of this patent is extended or adjusted under 35 U.S.C. 154(b) by 916 days.

(21) Appl. No.: 13/062,795

(22) PCT Filed: Sep. 8, 2008

(86) PCT No.: PCT/IB2008/003109
§ 371 (c)(1),
(2), (4) Date: May 27, 2011

(87) PCT Pub. No.: WO2010/026443
PCT Pub. Date: Mar. 11, 2010

(65) Prior Publication Data
US 2011/0225664 A1   Sep. 15, 2011

(51) Int. Cl.
*C12N 9/22*   (2006.01)
(52) U.S. Cl.
CPC ........................................ *C12N 9/22* (2013.01)
(58) Field of Classification Search
None
See application file for complete search history.

(56) References Cited

U.S. PATENT DOCUMENTS

| 7,842,489 | B2 | 11/2010 | Arnould et al. | |
|---|---|---|---|---|
| 7,897,372 | B2 | 3/2011 | Duchateau et al. | |
| 8,206,965 | B2 | 6/2012 | Arnould et al. | |
| 8,211,685 | B2 | 7/2012 | Epinat et al. | |
| 8,426,177 | B2* | 4/2013 | Gouble | 435/183 |
| 8,476,072 | B2 | 7/2013 | Cabaniols et al. | |
| 8,530,214 | B2 | 9/2013 | Arnould et al. | |
| 2002/0198144 | A1* | 12/2002 | Wong et al. | 514/12 |
| 2006/0010513 | A1* | 1/2006 | Melville et al. | 800/278 |
| 2006/0063231 | A1* | 3/2006 | Li et al. | 435/69.1 |
| 2006/0078552 | A1 | 4/2006 | Arnould et al. | |
| 2006/0099578 | A1* | 5/2006 | Wallace et al. | 435/6 |
| 2006/0141577 | A1* | 6/2006 | Otte et al. | 435/69.1 |
| 2006/0153826 | A1 | 7/2006 | Arnould et al. | |
| 2006/0206949 | A1 | 9/2006 | Arnould et al. | |
| 2009/0042250 | A1* | 2/2009 | Collingwood et al. | 435/69.1 |
| 2009/0098134 | A1* | 4/2009 | Buelow | 424/141.1 |
| 2009/0220476 | A1 | 9/2009 | Paques | |

(Continued)

FOREIGN PATENT DOCUMENTS

| WO | 2006 097853 | 9/2006 |
|---|---|---|
| WO | 2007 093836 | 8/2007 |

OTHER PUBLICATIONS

International Search Report Issued Mar. 24, 2009 in PCT/IB08/003109 filed Sep. 8, 2008.

(Continued)

*Primary Examiner* — Manjunath Rao
*Assistant Examiner* — William W Moore
(74) *Attorney, Agent, or Firm* — Oblon, McClelland, Maier & Neustadt, L.L.P.

(57) ABSTRACT

An I-CreI variant, wherein one of the two I-CreI monomers has at least two substitutions, one in each of the two functional subdomains of the LAGLIDADG core domain situated respectively from positions 28 to 40 and 44 to 77 of I-CreI, said variant being able to cleave a DNA target sequence from the glutamine synthetase gene. Use of said variant and derived products for improving expression system for the production of recombinant protein.

31 Claims, 27 Drawing Sheets

Figure 1:
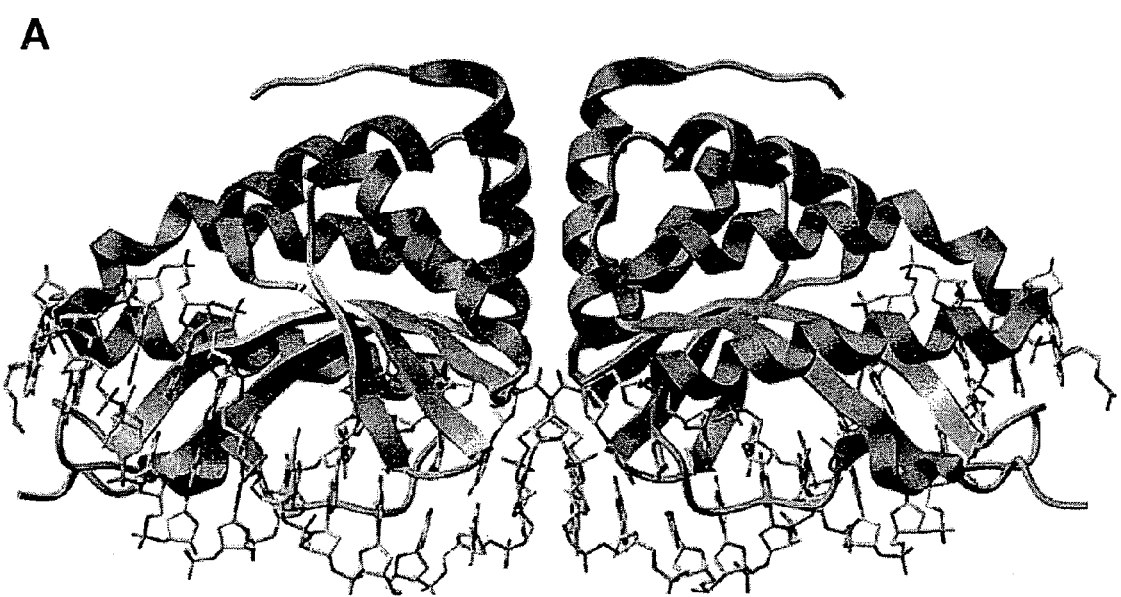

```
                    -12 -11 -10 -9 -8 -7 -6 -5 -4 -3 -2 -1  1  2  3  4  5  6  7  8  9 10 11 12

C1221      (T) CAAAACGTCGTACGACGTTTTG (A) (SEQ ID NO: 2)
10GCC_P    (T) CGCCACGTCGTACGACGTGGCG (A) (SEQ ID NO: 176)
10GGA_P    (T) CGGAACGTCGTACGACGTTCCG (A) (SEQ ID NO: 177)
5AGG_P     (T) CAAAACAGGGTACCCTGTTTTG (A) (SEQ ID NO: 178)
5TTC_P     (T) CAAAACTTCGTACGAAGTTTTG (A) (SEQ ID NO: 179)
GSCHO1         TGCCCCAGGGTGAGAAAGTCCA     (SEQ ID NO: 30)
GSCHO1.2       TGCCCCAGGGTACGAAAGTCCA     (SEQ ID NO: 180)
GSCHO1.3       TGCCCCAGGGTACCCTGGGGCA     (SEQ ID NO: 181)
GSCHO1.4       TGGACTTTCGTACGAAAGTCCA     (SEQ ID NO: 182)
```

(56) References Cited

U.S. PATENT DOCUMENTS

| | | |
|---|---|---|
| 2009/0222937 A1* | 9/2009 | Arnould et al. .................. 800/13 |
| 2009/0271881 A1 | 10/2009 | Arnould et al. |
| 2010/0086533 A1 | 4/2010 | Montoya et al. |
| 2010/0146651 A1 | 6/2010 | Smith et al. |
| 2010/0151556 A1 | 6/2010 | Arnould et al. |
| 2010/0167357 A1 | 7/2010 | Fajardo Sanchez et al. |
| 2010/0203031 A1 | 8/2010 | Grizot et al. |
| 2010/0229252 A1* | 9/2010 | Perez-Michaut ................ 800/13 |
| 2010/0325745 A1* | 12/2010 | Gouble ........................... 800/13 |
| 2011/0072527 A1 | 3/2011 | Duchateau et al. |
| 2011/0091441 A1* | 4/2011 | Gouble et al. .............. 424/94.61 |
| 2011/0151539 A1 | 6/2011 | Arnould et al. |
| 2011/0158974 A1 | 6/2011 | Duchateau et al. |
| 2011/0173710 A1 | 7/2011 | Grizot et al. |
| 2011/0179506 A1 | 7/2011 | Grizot |
| 2011/0179507 A1 | 7/2011 | Paques |
| 2011/0191870 A1 | 8/2011 | Paques |
| 2011/0207199 A1 | 8/2011 | Paques et al. |
| 2011/0239319 A1 | 9/2011 | Danos et al. |
| 2012/0159659 A1 | 6/2012 | Arnould et al. |
| 2012/0171191 A1 | 7/2012 | Choulika et al. |
| 2012/0244131 A1 | 9/2012 | Delacote et al. |
| 2012/0258537 A1 | 10/2012 | Duchateau et al. |
| 2012/0260356 A1 | 10/2012 | Choulika et al. |
| 2012/0272348 A1 | 10/2012 | Danos et al. |
| 2012/0288941 A1 | 11/2012 | Arnould et al. |
| 2012/0288942 A1 | 11/2012 | Arnould et al. |
| 2012/0288943 A1 | 11/2012 | Arnould et al. |
| 2012/0301456 A1 | 11/2012 | Tremblay et al. |
| 2012/0304321 A1 | 11/2012 | Arnould et al. |
| 2012/0317664 A1 | 12/2012 | Arnould et al. |
| 2012/0322689 A1 | 12/2012 | Epinat et al. |
| 2012/0331574 A1 | 12/2012 | Arnould et al. |
| 2013/0059387 A1 | 3/2013 | Smith et al. |
| 2013/0061341 A1 | 3/2013 | Arnould et al. |
| 2013/0067607 A1 | 3/2013 | Arnould et al. |
| 2013/0203840 A1 | 8/2013 | Arnould et al. |
| 2013/0209437 A1 | 8/2013 | Paques |
| 2013/0227715 A1 | 8/2013 | Danos et al. |
| 2013/0236946 A1 | 9/2013 | Gouble |

OTHER PUBLICATIONS

U.S. Appl. No. 90/012,131, filed Feb. 6, 2012, Duchateau, et al.
U.S. Appl. No. 90/011,665, filed May 10, 2011, Duchateau, et al.
U.S. Appl. No. 95/002,160, filed Sep. 7, 2012, Duchateau, et al.
U.S. Appl. No. 12/692,408, filed Jan. 22, 2010, Arnould, et al.
U.S. Appl. No. 90/011,806, filed Jul. 22, 2011, Arnould, et al.
U.S. Appl. No. 13/725,798, filed Dec. 21, 2012, Arnould, et al.
U.S. Appl. No. 12/527,790, filed Aug. 19, 2009, Arnould, et al.
U.S. Appl. No. 13/904,793, filed May 29, 2013, Gouble, et al.
U.S. Appl. No. 13/900,099, filed May 22, 2013, Cabaniols, et al.
U.S. Appl. No. 14/064,775, filed Oct. 28, 2013, Choulika, et al.

* cited by examiner

B
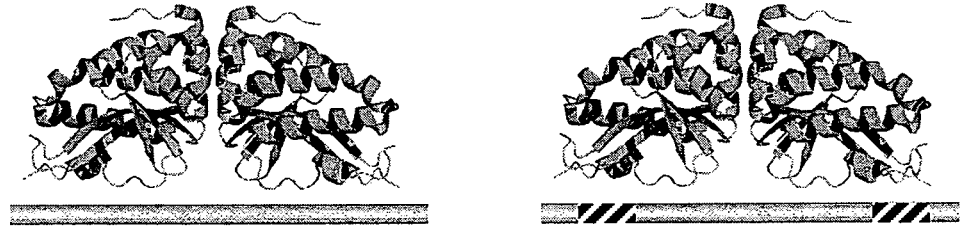
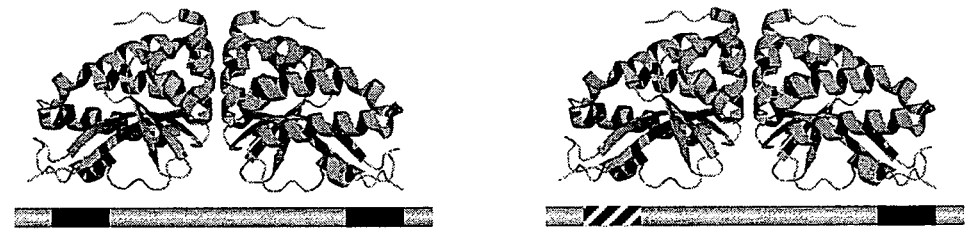
C
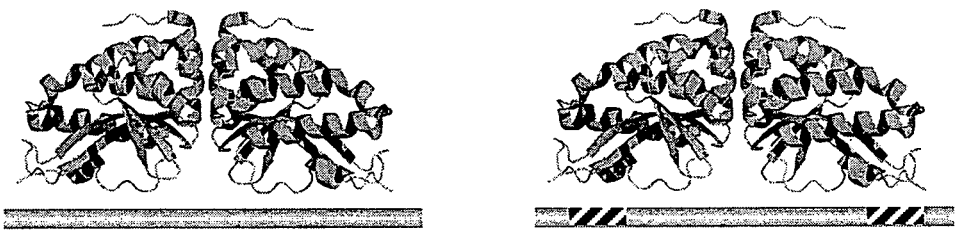
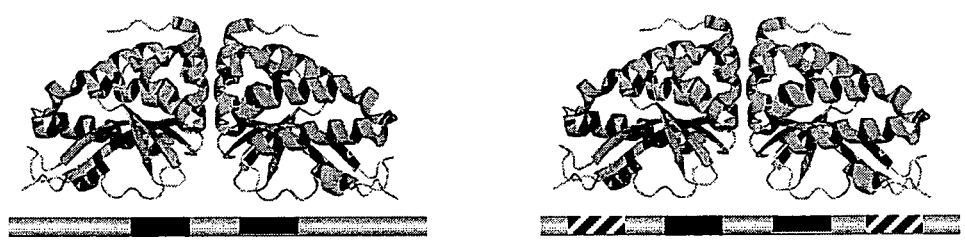
FIGURE 1 (CONTINUATION)

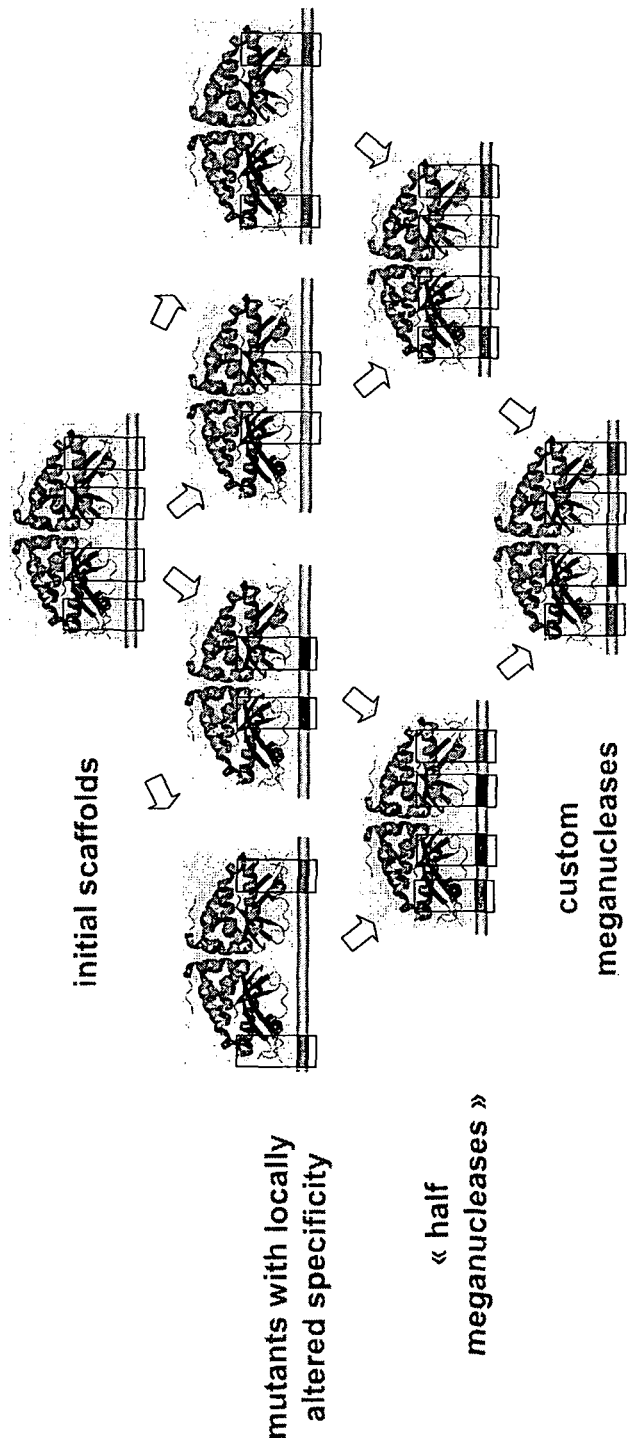
FIGURE 1 (CONTINUATION)

Figure 2:
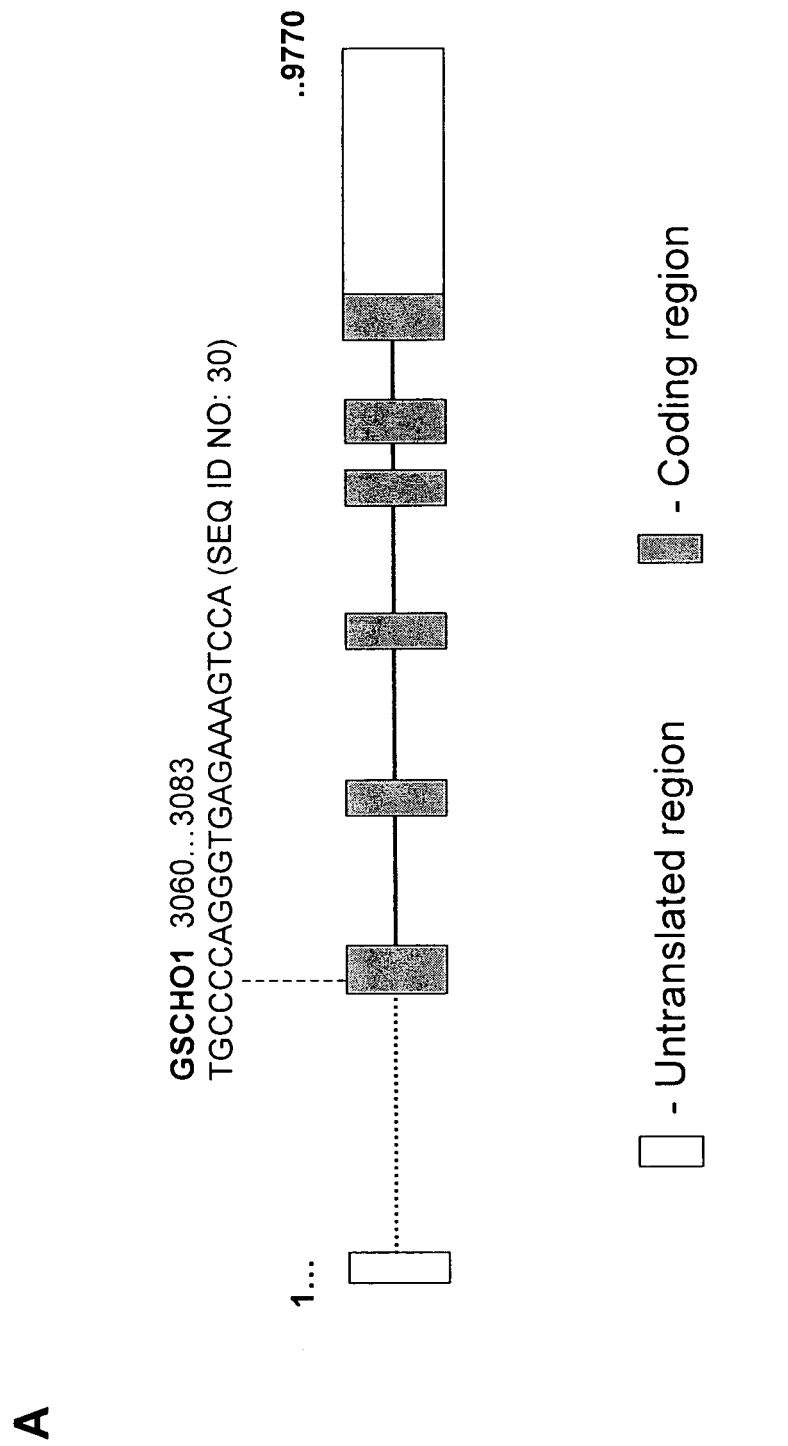

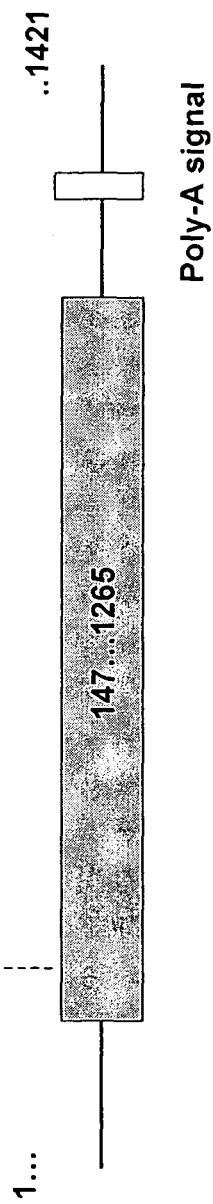
FIGURE 2 (CONTINUATION)

Figure 3:
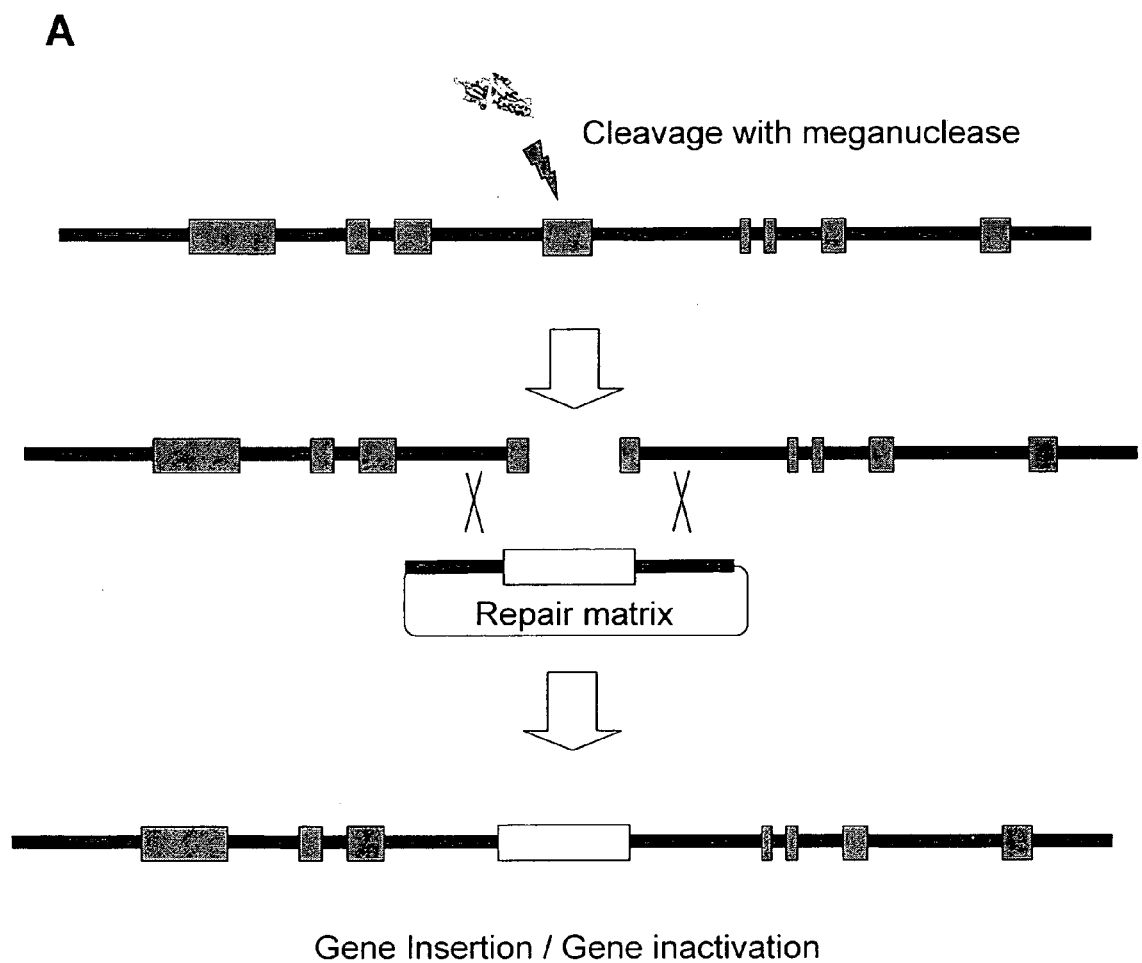

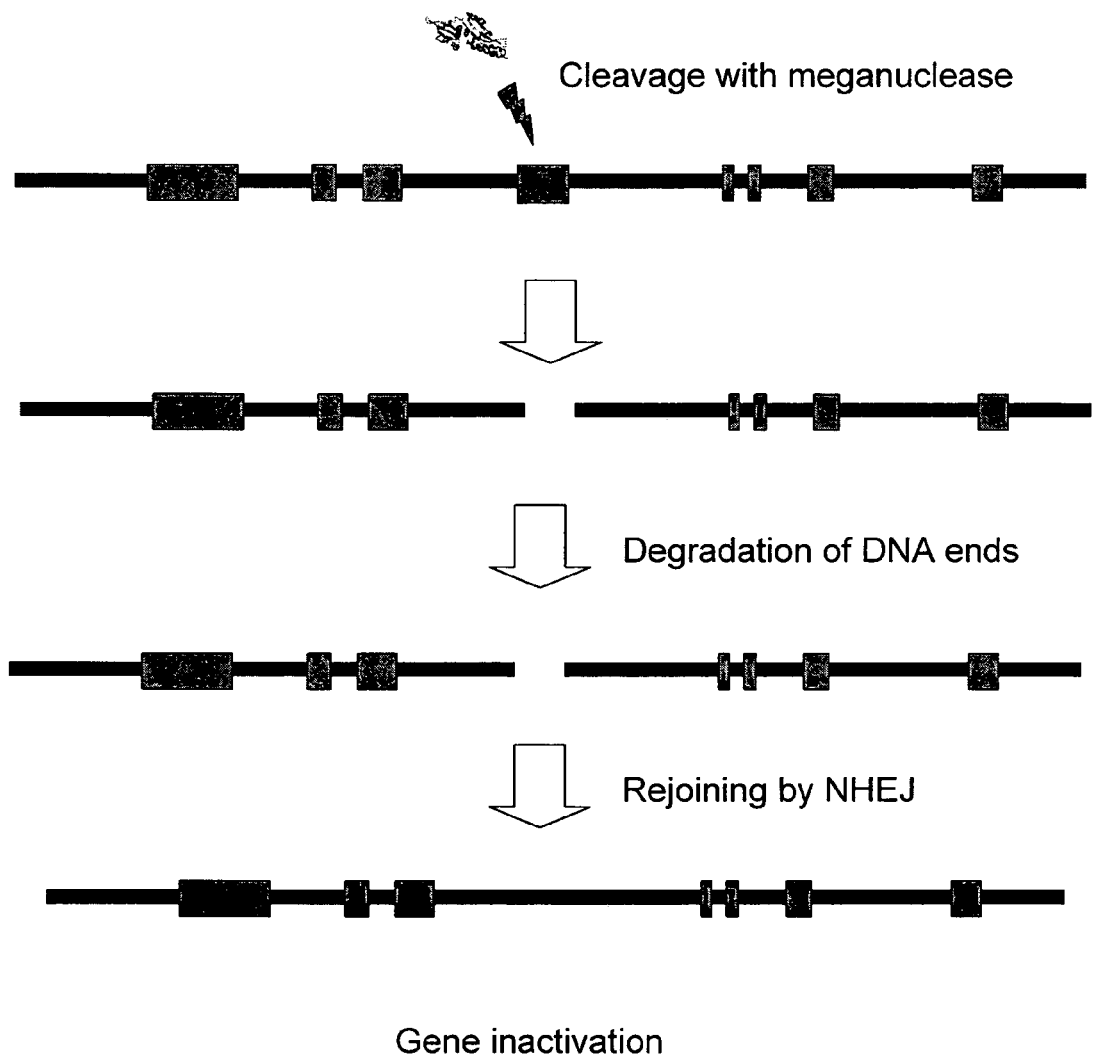
FIGURE 3 (CONTINUATION)

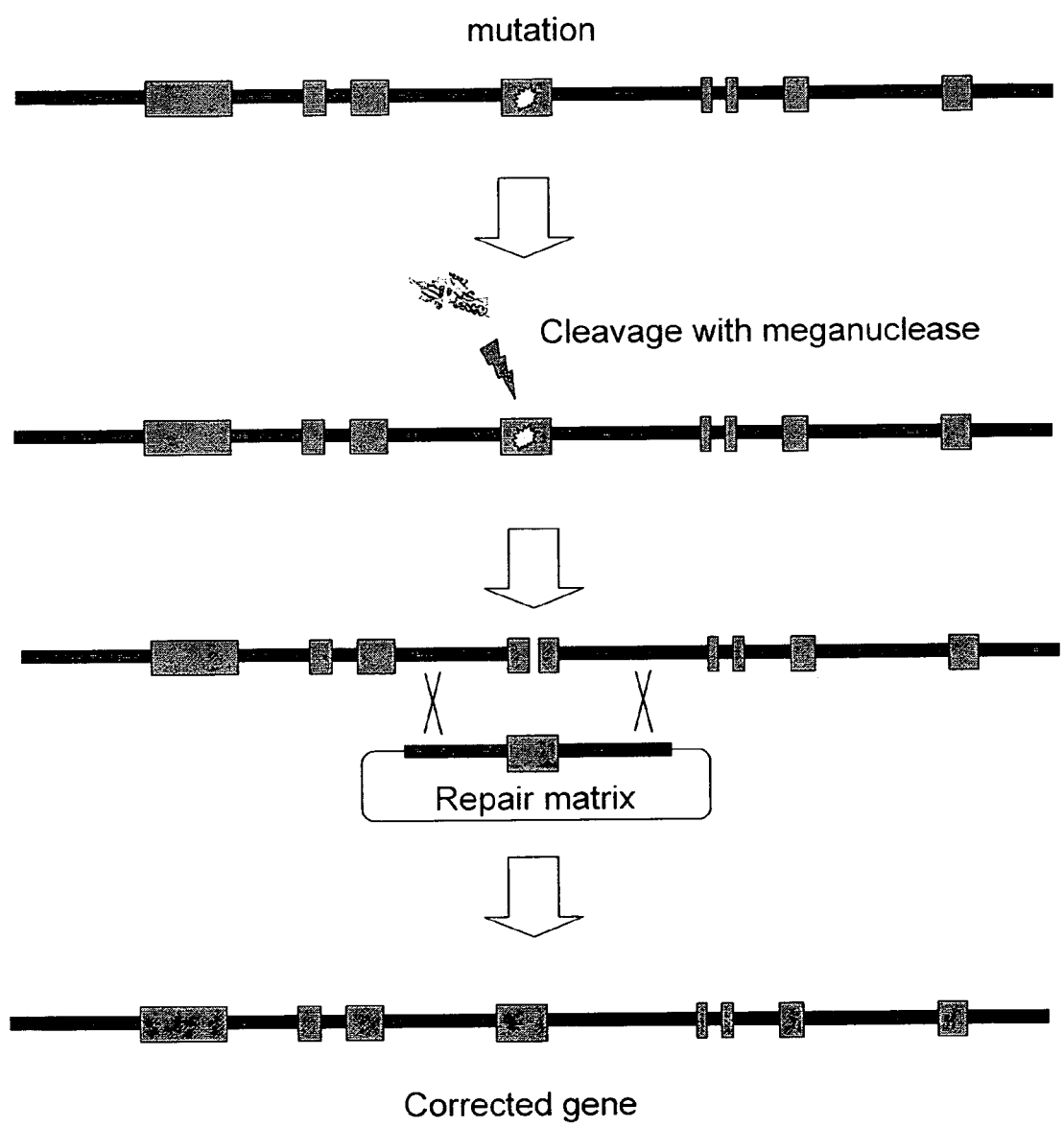
FIGURE 3 (CONTINUATION)

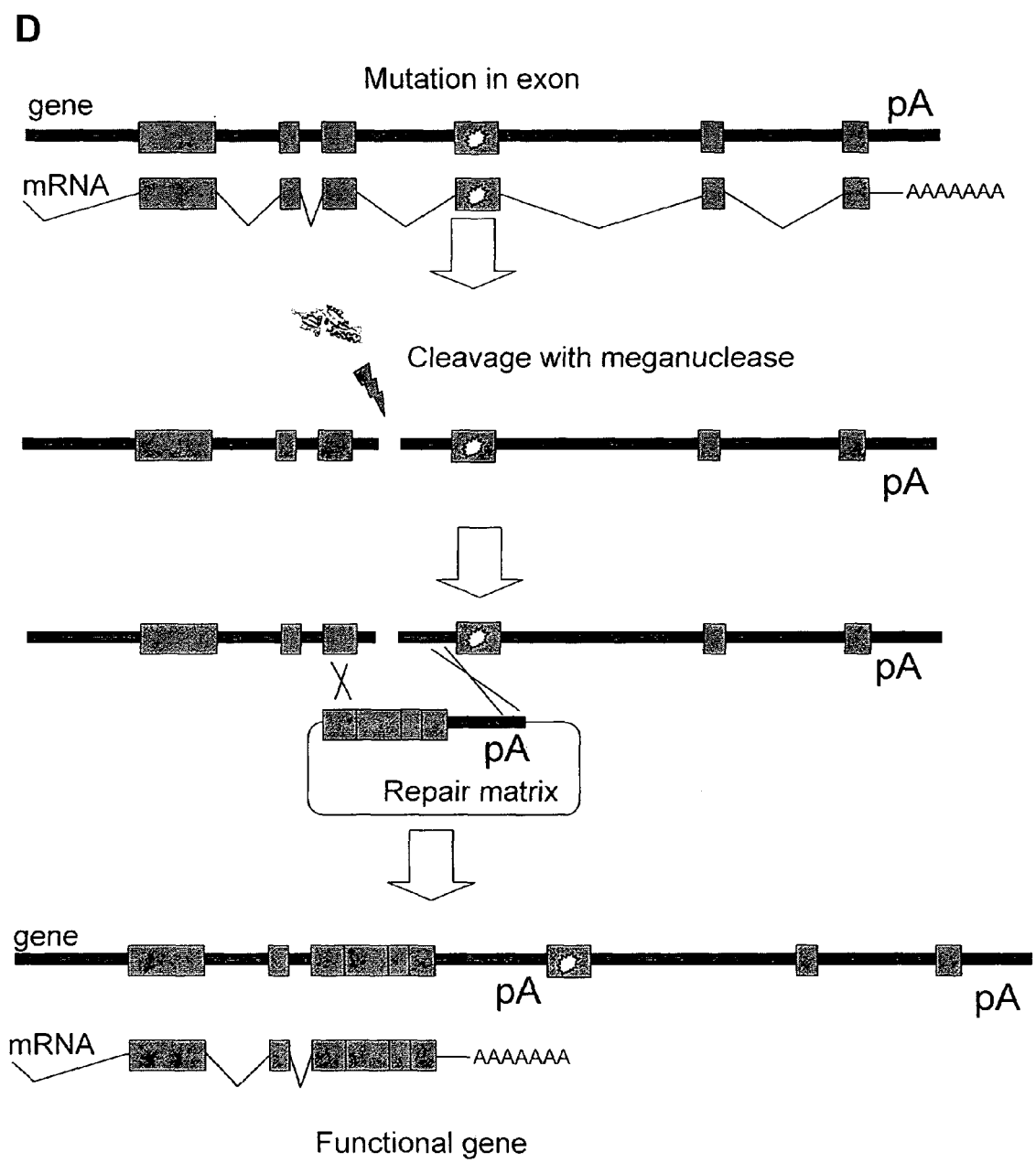
FIGURE 3 (CONTINUATION)

```
              -12 -11 -10 -9 -8 -7 -6 -5 -4 -3 -2 -1  1  2  3  4  5  6  7  8  9 10 11  12
C1221        (T) C A A A A C G T C G T A C G A C G T T T T G (A) (SEQ ID NO: 2)
10GCC_P      (T) C GCC A C G T C G T A C G A C G T GGC G (A) (SEQ ID NO: 176)
10GGA_P      (T) C GGA A C G T C G T A C G A C G T TCC G (A) (SEQ ID NO: 177)
5AGG_P       (T) C A A A A C AGG G T A C CCT G T T T T G (A) (SEQ ID NO: 178)
5TTC_P       (T) C A A A A C TTC G T A C GAA G T T T T G (A) (SEQ ID NO: 179)
GSCHO1            T GCC C C A G G G T G A GAA A G TCC A (SEQ ID NO: 30)
GSCHO1.2          T GCC C C A G G G T A C GAA A G TCC A (SEQ ID NO: 180)
GSCHO1.3          T GCC C C A G G G T A C C C T G G GGC A (SEQ ID NO: 181)
GSCHO1.4          T GGA C T TTC G T A C GAA A G TCC A (SEQ ID NO: 182)
```

FIGURE 4

Figure 10:
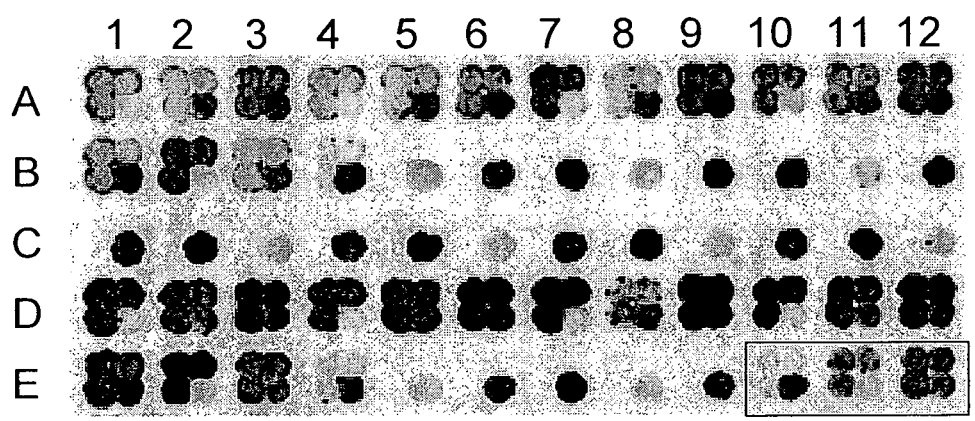

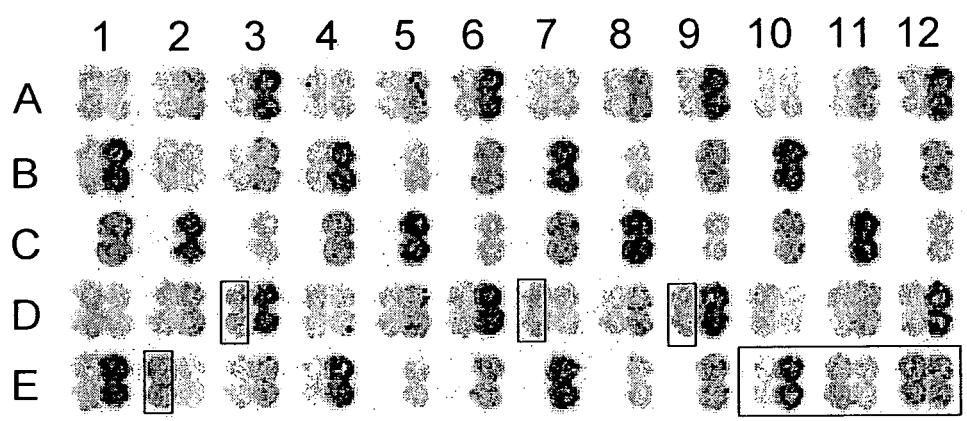
FIGURE 10 (CONTINUATION)

| N° | Exon position | Target SEQ ID NO: | Target position | Target Sequence | First I-CreI variant SEQ ID NO: | First I-CreI variant Sequence | Second I-CreI variant SEQ ID NO: | Second I-CreI variant Sequence | Minimal repair matrix Start | Minimal repair matrix End |
|---|---|---|---|---|---|---|---|---|---|---|
| 2 | 3066-3244 | 5 | 3077 | cc-atg-ac-cac-ctca-gca-ag-ttc-cc | 29 | 30T 33G 44V 68E 75N 77R 80K | 85 | 30R 32T 33N 40Q 44D 70S 75R 77T | 2988 | 3187 |
| 2 | 3066-3244 | 6 | 3162 | ca-tgt-at-atc-tgga-tcg-at-ggt-ac | 30 | 32G 33C 38A 44I 70S 75N 77R | 86 | 33R 38D 40R 44Y 68A 70S 75R | 3073 | 3272 |
| 2 | 3066-3244 | 7 | 3164 | tg-tat-at-ctg-gatc-gat-gg-tac-tg | 31 | 30R 32T 33C 40T 44K 68Y 70S 75E 77V | 87 | 30R 32T 33N 40Q 44L 70N 75N 80K | 3075 | 3274 |
| 2 | 3066-3244 | 8 | 3170 | tc-tgg-at-cga-tggt-act-gg-aga-ag | 32 | 33C 38A 44N 68T 70S 75R 77Y | 88 | 33T 38A 44M 68E 75N 77R | 3081 | 3280 |
| 2 | 3066-3244 | 9 | 3210 | cc-gga-cc-ctg-gaca-gtg-ag-ccc-aa | 33 | 33R 38N 40Q 44R 68Y 70S 75E 77V | 89 | 28E 33R 38R 40K 44N 70S 75R 77Y | 3121 | 3320 |
| 2 | 3066-3244 | 10 | 3216 | cc-tgg-ac-agt-gagc-cca-ag-tgt-gt | 34 | 32T 33C 44L 70A 75N 77V | 90 | 30Y 32T 33C 44D 68Y 70S 75S 77R | 3127 | 3326 |
| 3 | 4524-4685 | 11 | 4629 | ag-gac-cc-taa-caag-ctg-gt-gtt-at | 35 | 32H 33H 44N 68Q 70S 75S 77V | 91 | 33E 40E 44A 68Y 70S 75Y 77K | 4540 | 4739 |
| 4 | 5414-5560 | 12 | 5494 | ta-tac-cc-tca-tggg-gac-ag-atg-gg | 36 | 30R 32C 33C 40E 44K 68T 70T 75N | 92 | 32R 33D 44A 70S 75R 77L | 5405 | 5604 |
| 4 | 5414-5560 | 13 | 5514 | tg-ggc-ac-ccc-tttg-gtt-gg-cct-tc | 37 | 30R 68E 70S 75R 77R | 93 | 30S 33H 38K 44N 68Y 70S 75R 77V | 5425 | 5624 |
| 4 | 5414-5560 | 14 | 5543 | gc-ttc-cc-agg-gccc-cag-gg-taa-gt | 38 | 33T 44A 70S 75E 77V | 94 | 33P 40Q 44K 68Y 70S 75E 77V | 5454 | 5653 |
| 5 | 5929-6056 | 15 | 5912 | tc-ctg-al-gct-tctg-tag-gt-cca-ta | 39 | 30D 33R 38T 44R 70S 75N 77D | 95 | 32C 33C 38H 44R 70S 75N 77D | 5823 | 6022 |
| 5 | 5929-6056 | 16 | 6025 | cg-ggg-ac-taa-tgcc-gag-gt-cat-gc | 40 | 32H 33H 44Y 68Y 70S 75S 77T | 96 | 30T 33G 70S 75Y 77R | 5936 | 6135 |
| 5 | 5929-6056 | 17 | 6043 | tc-atg-cc-tgc-ccag-gta-ag-tat-ag | 41 | 30T 33G 44K 70S 75N 77R | 97 | 33R 38A 40Q 44N 70S 75R 77Y | 5954 | 6153 |
| 6 | 6260-6459 | 18 | 6361 | ag-caa-cc-ttt-gatc-cta-ag-ccc-at | 42 | 44K 68Y 70S 75N 77Q | 98 | 28E 33R 38R 40K 44K 68Y 70S 75Q 77N | 6272 | 6471 |
| 6 | 6260-6459 | 19 | 6430 | ca-agg-cc-cggg-agg-ag-aat-gg | 43 | 30S 33H 38K 44I 70S 75N 77R | 99 | 32D 38C 44K 68E 70S 77R | 6341 | 6540 |
| 7 | 7093-9282 | 20 | 7075 | ct-ttt-ct-gtt-tact-cta-gg-tac-at | 44 | 33T 40T 68N 70S 75Q 77R | 100 | 33R 38A 40Q 44A 68Q 70N 75N | 6986 | 7185 |
| 7 | 7093-9282 | 21 | 7135 | gt-acc-ac-atc-cgtg-cct-at-gat-cc | 45 | 33R 38D 40R 44I 70C 75N 77R | 101 | 30R 32A 33N 40E 44A 70S 75E 77R | 7046 | 7245 |
| 7 | 7093-9282 | 22 | 7144 | cc-gtg-cc-tat-gatc-cca-ag-gga-gg | 46 | 33P 38K 44N 68K 70H 75N | 102 | 28R 33A 38Y 40Q 44D 68Y 70S 75S 77R | 7055 | 7254 |
| 7 | 7093-9282 | 23 | 7168 | cc-tgg-ac-aat-gccc-gac-gt-cta-ac | 47 | 33C 38A 44I 70A 75N 77R | 103 | 32T 33C 70S 75H 77Y | 7079 | 7278 |
| 7 | 7093-9282 | 24 | 7178 | gc-ccg-ac-gtc-taac-tgg-at-tcc-at | 48 | 32T 38W 44A 70S 75R 77L | 104 | 33R 38N 40Q 44Y 68S 70S 75S 77D | 7089 | 7288 |
| 7 | 7093-9282 | 25 | 7225 | tt-ctg-ct-ggt-gtag-cca-at-cgt-ag | 49 | 30D 33R 38S 44Y 70S 77V | 105 | 32T 38W 44D 68Y 70S 75S 77R | 7136 | 7335 |
| 7 | 7093-9282 | 26 | 7260 | gc-att-cc-ccg-gact-gtt-gg-cca-gg | 50 | 30T 33G 44K 70S 77K | 106 | 28N 33S 38R 40K 44A 68Y 70S 75R | 7171 | 7370 |
| 7 | 7093-9282 | 27 | 7267 | cc-gga-ct-gtt-ggcc-agg-ag-aag-aa | 51 | 33R 38N 40Q 44S 70S 75Y 77T | 107 | 30D 33R 44K 68E 70S 77R | 7178 | 7377 |
| 7 | 7093-9282 | 28 | 7274 | gt-tgg-cc-agg-agaa-gaa-gg-gtt-ac | 52 | 33C 38A 44A 70S 75E 77R | 108 | 30R 33R 68Y 75N | 7185 | 7384 |

Figure 18

| N° | Exon position | Target | | First I-CreI variant | | Second I-CreI variant | | Minimal repair matrix | |
|---|---|---|---|---|---|---|---|---|---|
| | | Sequence | SEQ ID NO: | Sequence | SEQ ID NO: | Sequence | SEQ ID NO: | Start | End |
| 2 | 2990-3168 | ca-tgc-cc-acc-tcag-caa-gt-tcc-ca | 29 | 3002 | | | 129 | 2913 | 3112 |
| 2 | 2990-3168 | ct-gcc-cc-agg-gtga-gaa-ag-tcc-aa | 30 | 3060 | 30R33R38E44D68Y70S75Y77Q | 110 | 30R32G44R68H | 130 | 2971 | 3170 |
| | | | | | | 30R32G44K68H | 131 | | |
| | | | | | | 30R32G44K68N | 132 | | |
| | | | | | | 30R32C44R68H | 133 | | |
| 2 | 2990-3168 | tg-tat-at-ctg-ggt-gat-gg-tac-cg | 31 | 3088 | 30H 32H 33C 40T 44R 68Y 70S 75E 77V | 111 | 30R 32T 33N 40Q 44I 70C 75N 77R | 134 | 2999 | 3198 |
| 2 | 2990-3168 | cc-gta-cc-ctg-gact-gtg-ag-ccc-aa | 32 | 3134 | 33R 38A 40Q 44R 68Y 70S 75E 77R | 112 | 33H 38A 44V 68E 75N 77R 80K | 135 | 3045 | 3244 |
| 3 | 4593-4754 | cg-gaa-ac-ctg-cagg-caa-gt-atg-gg | 33 | 4742 | 30R 32G 33R 40A 44R 68Y 70S 75E 77R | 113 | 32R 33D 44I 68Y 70S 75R 77T | 136 | 4653 | 4852 |
| 4 | 6405-6551 | ag-caa-cc-agc-accc-ctg-gt-ttg-ga | 34 | 6449 | 44L 70N 75N 80K | 114 | 24V 44N 68Y 70S 75Y 77N | 137 | 6360 | 6559 |
| 4 | 6405-6551 | ct-ctt-at-ggg-aaca-gac-gg-cca-cc | 35 | 6489 | 30D 33R 44Y 70S 77V | 115 | 30H 32H 33C 38A 44D 70S 75R 77Q | 138 | 6400 | 6599 |
| 4 | 6405-6551 | gc-ttc-cc-tgg-accc-caa-gg-tac-gt | 36 | 6534 | 33T 44D 68Y 70S 75S 77R | 116 | 33R 38A 40Q 44R 68N 70S 75Q | 139 | 6445 | 6644 |
| 5 | 7076-7203 | cg-ggg-ac-aaa-tgcg-gag-gt-tat-gc | 37 | 7172 | 32H 33H 68H 70S 75N 77R | 117 | 33G 40Q 68Y 70S 75R 77V | 140 | 7083 | 7282 |
| 5 | 7076-7203 | gc-ctg-cc-cag-gtaa-atg-gt-gcc-ca | 38 | 7194 | 30D 33R 38T 44A 68Y 70S 75Y 77K | 118 | 30R 32T 44R 68S 70S 75S 77T | 141 | 7105 | 7304 |
| 6 | 7342-7541 | gt-caa-ct-ttt-tctc-tct-ag-tgg-ga | 39 | 7323 | 33C 40Q 70S 75N 77R | 119 | 32D 38Y 44T 68Y 70S 75R 77V | 142 | 7234 | 7433 |
| 6 | 7342-7541 | ta-gga-cc-ctg-tgag-ggg-at-ccg-aa | 40 | 7355 | 30R 44R 68Y 70S 75E 77Q | 120 | 38R 40K 44K 68S 70S 75N | 143 | 7266 | 7465 |
| 6 | 7342-7541 | tt-tgg-at-agc-ccgt-ttt-at-ctt-gc | 41 | 7391 | 33C 38A 44N 68Y 70S 75R 77V | 121 | 32T 68H 70S 75N 77R | 144 | 7302 | 7501 |
| 6 | 7342-7541 | gt-ttt-at-ctt-gcat-cgg-gt-gtg-cg | 42 | 7403 | 33S 38R 40D 70S 75N | 122 | 44K 68E 70S 77R | 145 | 7314 | 7513 |
| 6 | 7342-7541 | tt-tat-ct-tgc-atcg-ggt-gt-gcg-aa | 43 | 7405 | 32T 33C 44E 68C 70S 75N | 123 | 32N 33G 44K 68Y 70S 75N | 146 | 7316 | 7515 |
| 6 | 7342-7541 | ca-agg-cc-atg-cggg-agg-aq-aat-gg | 19 | 7512 | 30S 33H 38K 44I 70S 75N 77R | 75 | 32D 38C 44K 68E 70S 77R | 99 | 7423 | 7622 |
| 7 | 7920-9770 | tc-gcg-cc-tac-gatc-cca-ag-ggg-gg | 44 | 7971 | 30T 33H 36R 44N 70S 75R 77Y | 124 | 32T 38W 44D 68Y 70S 75S 77R | 147 | 7882 | 8081 |
| 7 | 7920-9770 | cc-tgg-ac-aac-gccc-ggc-gt-ctg-ac | 45 | 7995 | 30S 33S 38H 44A 68Y 70S 75R 77V | 125 | 30D 33R 38G 68N 70S 75R 77V | 148 | 7906 | 8105 |
| 7 | 7920-9770 | gc-att-cc-ccg-gact-gtc-gg-cca-gg | 46 | 8087 | 30D 33R 44K 68E 70S 77R | 126 | 28N 38R 40K 44A 75N | 149 | 7998 | 8197 |
| 7 | 7920-9770 | cc-gga-ct-gtc-ggcc-agg-ac-aag-aa | 47 | 8094 | 33R 38N 40Q 44A 70S 75R 77L | 127 | 30W 33C 44K 68A 70S 77K | 150 | 8005 | 8204 |
| 7 | 7920-9770 | gt-cgg-cc-agg-agaa-gaa-gg-gct-ac | 48 | 8101 | 30G 38K 44T 70S 75E 77R | 128 | 38G 40Q 44K 68Y 70S 75N 77Q | 151 | 8012 | 8211 |

Figure 19

| Exon N° | Target | | | First I-CreI variant | | Second I-CreI variant | |
|---|---|---|---|---|---|---|---|
| | Sequence | SEQ ID NO: | position | Sequence | SEQ ID NO: | Sequence | SEQ ID NO: |
| 2 | ca-tgg-cc-acc-tcag-caa-gt-tcc-ca | 29 | 146 | 32C 33C 38H 44K 68Y 70S 75N | 109 | 30R 44T 68Y 70S 75R 77T | 129 |
| | | | | | | 30R32G44R68H | 130 |
| | ct-gcc-cc-agg-gtga-gaa-ag-tcc-aa | 30 | 204 | 30R33R38E44D68Y70S75Y77Q | 110 | 30R32G44K68H | 131 |
| | | | | | | 30R32G44K68N | 132 |
| 2 | | | | | | 30R32C44R68H | 133 |
| 2 | tg-tat-at-ctg-ggtt-gat-gg-tac-tg | 49 | 232 | 32H 33C 40A 44R 68Y 70S 75E 77R | 152 | 30R 32T 33N 40Q 44I 70S 75N 77R | 164 |
| 2 | cc-gca-cc-ctg-gact-gtg-ag-ccc-ga | 50 | 278 | 33R 38D 40R 44K 68Y 70S 75E 77V | 153 | 33G 40G 44T 68Y 70S 75Y 77R | 165 |
| 3 | ct-cag-cc-ctg-ttgc-cat-gt-ttc-gg | 51 | 381 | 33N 40R 44K 68Y 70S 75E 77V | 154 | 30R 32D 44N 68Y 70S 75R 77Q | 166 |
| 3 | cg-gga-cc-cct-tcgg-cag-ag-atc-cc | 52 | 402 | 30R 44K 68E 70S 77R | 155 | 32H 33H 44R 68Y 70S 75E 77Y | 167 |
| 4 | ag-caa-cc-agc-accc-ctg-gt-ttg-ga | 34 | 519 | 44L 70N 75N 80K | 114 | 24V 44N 68Y 70S 75Y 77N | 137 |
| 4 | tg-ggc-ac-cct-tttg-gtt-gg-cct-tc | 53 | 575 | 30R 44K 68S 70S 75N 77V | 156 | 30S 32T 33S 38R 44A 68Y 70S 75H | 168 |
| 5 | ca-aag-cc-tat-ggca-ggg-at-atc-gt | 54 | 650 | 30S 33C 40A 44N 68K 70H 75N | 157 | 32G 33H 68E 70S 75R 77R | 169 |
| 5 | ca-gga-ac-aaa-tgct-gag-gt-cat-gc | 55 | 718 | 30R 68H 70S 75N 77R | 158 | 30T 33G 68Y 70S 75R 77V | 170 |
| 6 | tt-cat-ct-tgc-atcg-agt-at-gtg-aa | 56 | 813 | 32R 33D 44E 68C 70S 75N | 159 | 33N 38Y 40R 70D 75N 77R | 171 |
| 6 | ca-agg-cc-atg-cggg-agg-ag-aat-gg | 19 | 920 | 30S 33H 38K 44I 70S 75N 77R | 75 | 32D 38C 44K 68E 70S 77R | 99 |
| 7 | tc-gag-cc-tac-gatc-cca-ag-ggg-gg | 57 | 1001 | 33H 40T 44N 70S 75R 77Y | 160 | 30R 38E 44D 68Y 70S 75S 77R | 172 |
| 7 | cc-tgg-ac-aat-gccc-gtg-gt-ctg-ac | 58 | 1025 | 33C 38H 44V 68E 75N 77R 80K | 161 | 28S 38R 40K 44N 70S 75R 77Y | 173 |
| 7 | tt-ctg-ct-ggt-gtcg-cca-at-cgc-ag | 59 | 1082 | 30D 33R 38T 44Y 70S 77V | 162 | 30K 33S 44D 68Y 70S 75S 77R | 174 |
| 7 | gc-att-cc-ccg-gact-gtc-gg-cca-gg | 46 | 1117 | 30D 33R 44K 68E 70S 77R | 126 | 28N 38R 40K 44A 75N | 149 |
| 7 | cc-gga-ct-gtc-ggcc-agg-ag-aag-aa | 47 | 1124 | 33R 38N 40Q 44A 70S 75R 77L | 127 | 30W 33C 44K 68A 70S 77K | 150 |
| 7 | gt-cgg-cc-agg-agaa-gaa-ag-gtt-ac | 60 | 1131 | 30G 38K 44A 70S 75E 77R | 163 | 33R 40R 44A 70G 75N | 175 |

Figure 20

SEQUENCE LISTING

<160> NUMBER OF SEQ ID NOS: 272

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 24
<212> TYPE: DNA
<213> ORGANISM: artificial sequence

```
<220> FEATURE:
<223> OTHER INFORMATION: C1221 DNA target

<400> SEQUENCE: 2
tcaaaacgtc gtacgacgtt ttga                                              24

<210> SEQ ID NO 3
<211> LENGTH: 9770
<212> TYPE: DNA
<213> ORGANISM: Mus musculus

<400> SEQUENCE: 3
cagagcggag aatgggagta gagcagagtg tctgaacagc acgctcaccc atctcctctc        60
cgcctcgctc tcctgacctg ttcacccatc catcatccgg ccggccaccg ctctggtaag       120
cgcacggagg gtccaggaat gtacggccgc ccgggctgtg gggtcgcact ctacttccca       180
gctccagtca gctgctgtac ggagcgggat gcagcgctcg tgcctcccgc gtgtttgcag       240
cgtgcggccc gggccggctc tgcttggtgt tcctaggacg cgctgtgagc caagctccgg       300
gaagggcggg gttgcgggtt gttttgatct gttctatact tgcggccgga ggcgccgccc       360
cgggaggcag gcgccgttgg ctggggttca cgctgagatg ggggcttttcc ggtggtccca      420
gcgggagagg gttcttgcct taggtgggcg caggcgcctt gatcctctct tcctggcggc       480
gcatttgggg ggcgtcgtca cgctgtgggt ggtctggttg aggatggtgg tcctaagcgt       540
tgatggcacc actccccagc tcccaacgcc gtgtcctagg cctttaccat atgaccgaac       600
aatggagagc cggagccccg gagtggccgg cgggctccgc agtggagagg ccgcgccaag       660
cggaggcagc agcggcgcgc tgtgcctccc gcggtcgccc cactctcgcc acccggcctc       720
taccctcgcc ggggtatggc cccctgggag aggccttgag atctacgcgg gcccgagggt       780
cgcggcaccg actttccgga catttttagtg ggaaggctgc tttcaaagtg gattgcccca      840
actcctccgg gggcgggaag cggggatcct ccccccagccg caaatactca agaaaccaa       900
ccattgaaga cgtagaagat ggagattctc ggtcctcaga gtcccttct aatactttag         960
gcttcgttgc ctactctgtg aactccgggg agaagtcgag ggttaagatt aaatcgcacc      1020
cgtcttattc cagcacctcc ccctccgaac ggtctgggtc ccccactcca tcgccctcgc      1080
ccaaaaagct ccgttgctta gaccagcgag aaatcgagaa cgaggagagg catgaacact      1140
gctctaaaaa gaggaggtct agagagtaca accccagtgc atttgattct cattggctgg      1200
ggtgagtaaa agtcagggcg aaggaccccg ggtgcatctg gcaacccgca gaaactactc      1260
agaattttaa gaacccattc cactttgcac tacaggaca ccagttggtg ctatctatgt       1320
acactaggct gctggcaccc agctggtctc agggaaccag ggccagagga ggaactcagg      1380
ttcccctaac agttcattaa tgctggatgt gtgtgtgtgg ggggcggggg gcacggcaga      1440
ggaggaaagc tgatgagtgg tgtaaattga agccatctag aattacaatc cgggcctcta      1500
agtggtgtag gcagaggctt tggttctgca tcgacttga cagcagaggc tcatctgttc       1560
cccgggggaa gggtgaggct tttggaggga gaggcagttg ttttcacttg gcaaacatg       1620
gacggttgcc catagaaact ttgccactgt acttcagaaa gttgcccaag tcattggagg      1680
agaacaatat gttccctctc cagctatccg gggagattag ggagggaggg gggcatttcc      1740
tcttgtgttt tgaggctggt ttttttgtagc ctcacattca tcgaagatct tgccccgact      1800
cctgtggctt gtaaacttag aagtgggatt tttctacgta ccagaaaata ttatccggtg      1860
ggatcgtcaa atactgttaa ttttcacatt gaaatctgtc tctggagtaa ggcttttcac      1920
```

```
cacagtaatg aagtcagcag ttgaggcctg gtgtggaggg ggcatacctt taatcccagc   1980
tctcaggagg cagagactgg tagatcctct gattttgagg aaagcttggt gtaaataatg   2040
agtaagtaat tactaggaca gagagagggc ttgttgagat ttctctgtct caaaaaaaaa   2100
aaaaaaaaac caaaaaacca gtcagcagtg tgctccttgg agtatggctt tacttttttac  2160 caccttagtg gtggcagata atacaggtcc tttctttctc ccaggaatat gttagccttt   2220
aaagtcttac agctagccct agtatttcat tgtgtaatct aaagatggtg gtggcataca   2280
cctttaattc tagcgttcag gatgctgaga ggggcagatc taatttgatt ctgaggctag   2340
cctggtcggc ataagttcca gggctccaca atgagacttt gtctcaaata agtagatagt   2400
ctaaatgtag gtatgtaggg attacaatgg gttgtgtgtc ccttaaggtt gttccaagag   2460
ctgagcggtg gtggcacatg cctttattta atcccagcac ttgggaggca gaggcaggtg   2520
gatttctgag ttcaaggcca gcctggtcta caaagtgagc tccaggacaa ccagggccat   2580
tcagagaaac cctgtctcca aaaaaaaaaa aaaaggctgt tccaaagagt ggaagacaaa   2640
gcaagactca acagtcaatt agtcaagtct ttctgtggca ataaggtagt tctgttggta   2700
gaataagata ttctgttaat gaacgtcttg atatttgttc tctcctgcta acatttctca   2760
agtttaacgg ttattaaaat cccttaacta gtcccccctga gggggcatgg tccttgtcta  2820
atataaaact ttaaacccct tgaaagcaga gtgaataatg caccctttgtg tgtgtccagt  2880 cccagaggag cgagatcacc acgcacgcca gcctgattcc cttgccgtcc cctacagtgg   2940 atcccttga attcgatatt aataaaatgc gatttctgtc tctctccaga acaccttcca    3000
ccatggccac ctcagcaagt tcccacttga acaaaggcat caagcaaatg tacatgtccc   3060
tgccccaggg tgagaaagtc caagccatgt atatctgggt tgatggtacc ggagaaggac   3120
tgcgctgcaa gacccgtacc ctggactgtg agcccaagtg tgtggaaggt gagtgccggg   3180
gcggagtgtg cgcacgcctg ggagtgtacg cacagcctcg gatccacctt ccttctgttt   3240
ggtttgcaag gcttttcaga ccttagtcag tcacccgtaa gtaagctgct gcatagtctg   3300
gaggcgcagc aacaatggaa gcctttcttt agatggactc tggcgtgtgc tggtacattg   3360
aagaaaaata ctgggtcacg tttgtggggg atggaggct gctgtgtgct aacctggcca    3420
accccaggaa cctagtttga gaggactggt gtaactggaa tatgctatct agtttataga   3480
acagtcggtc tcaacccttc ctaatgcttc caccatttaa taaggctagt gttgtggcaa   3540
ccaccaacca taaaatggtt tttgccgcta ctttataatt gtatatactt ctaagtttat   3600
tttagttgta gcctgtgttt ctcagcatag accaagtaag ccatagctgc tcaggagagg   3660
ggtggccccc tcaccatcta cctggcttag gatgggttac tcttccaagg atgtttctgt   3720
ttgagtgaac gagtgaccag ataacagagc atggattgta tacttggtac ttggcagagt   3780
gtgggtaggt tcttcagtct ctgctttctg agaactcaga ggtaactgga gagtcaaacc   3840
cgaccactaa gacagtaggg aaaagaccaa gcaagcggtg gggaagcaac tgtttatata   3900
caagcataac ttgaagtaca acagttggac ctgtggggaa tgggagaagg gagatgatga   3960
tggcctagag gaggaggtgg ggttttttg tttgttttgg gttttgtcct gtgtgtgtct    4020
gacacactgg aagtgatacc agagtacaca ggagacttgc acagagagga ctggtttttct  4080 gctcaggtgg ctcttgggat gcagtgctct ggggactctc aggtcaggag aaactgggat   4140
aggtgacagc gataggtgac gtcaggttat ccctgatgta gatgcagtca catgcacctc   4200
actcctcata aagacaaagt ggtggtgagc aacgaaagga tgagtaagag gctgaccgtc   4260
ttcttagcgt gtgcactaaa aacttttaaa actgtatgta tatgggtgtg tatgtgcgcg   4320
```

```
cgcgcacgcg cgctccatgt gctcagtgcc agcagaaatc aaagagtgag gaccgcagga    4380
actgaagtta cagacagttg tgggctttca tgtgattgag agctcttgtt gctctcaccg    4440
atctgggttc agttaacaac acccacatag tggctcacaa ccatctgtaa ctctcaattc    4500
cgggagatcc aaccctcctc gtctggcttc ttcctgcagg ctcaaataac acgtttaaag    4560
ttaatttaat tttctatctt tgtcttgccc agagttacct gagtggaact ttgatggctc    4620
tagtaccttt cagtctgaag gctccaacag cgacatgtac ctccatcctg ttgccatgtt    4680
tcgagacccc ttccgcaaag accccaacaa gctggtgcta tgtgaagttt caagtataa    4740
ccggaaacct gcaggcaagt atgggatggg tgtggctggc tgtaaatcct gaaactctag    4800
ggaggtgaca ttctcaatga attgagaagc cgctctctaa gaacgtaggg atggcagggt    4860
ggctattcta ccctgaactt tcctgttggg aacagtgtgc tcaatccttt cttccatggt    4920
tcctttattt gtttgtatag tgttggctct tctgtctgtt tgctgacggg caacctctac    4980
ctgctgatct aaaagcctgt gtttaaaagt tctgtagttt ttgaatttaa atactagatc    5040
taccactgtt ctacctgctt ttttttcttc tgaattgtgt gtgctgtatg tggagagcat    5100
gcgtcggaga gcatgccttg ctgggtgcgt ggacgtcaac gggcagcgtt ggagttggtt    5160
gtctcctgcc tgtttatgtg agctctggag gtggaactca ggttgccagg ctcgagtggc    5220
aacacctta cccactgagc cgtctcagta gtcttctctg ataagagccc atcccgaagt    5280
cattggaaga tcacatgaat gaccgtgtgc cacaatcact gggagtact gcacgttaac    5340
tatcggttac tattttatgc cagacagctt gttgagtctg aatactcaca agtatgagca    5400
tcgagacttc gggatgtgca tttaccctgc ctgcacatgc gtggagttta gtttgcactg    5460
tgctatccat ctccgttttc agatagcttt gaacctgggg aagtctcact tctgtgaaat    5520
atcttctagc aatgccagta aggcttggtg gccctgggcc ttcagtgctt ctgtttcaaa    5580
aggcagtagc attattggta aaggtgtgc tctgtgcctg tcctgtcacc tgggtgtgcc    5640
acctaacacc ctctcttggg gtttcatttt cttatttgtg aaaatgaagg tttttttggt    5700
ttgttttttt ttgtttttt ttttccaaga cagagtttct ctgtgtagcc ctggctgtcc    5760
tggaactcac tctgtagacc aggctggcct tgaactcaga aatctgcctg cctctgcctc    5820
ccaagtgctg ggatcaaagg tgtgcgccac catgccctgc caaaatgaag gttgttaata    5880
ccttagactc agatggttat ttttttcta gcttgggaat tgttttcagc tatactcata    5940
tataattata tgtctgtatg tctgtctacc tatctacttt tgtaccagtc ataactgtaa    6000
aacttagcac ttaaactcac ctggcatgtg aacctaatgg acaaattatt ctcaataaca    6060
gatctggcct tcagtgtctg agacactagg gaatacatct gacaactaga agcagttgtc    6120
ctgtgaatct gagaatgagt gcctggcgtg tggtgttggg atggtggcca gcatgcagat    6180
agggtgacca cttgctcgga ttccattccc atgatgctgc gtggctgact taattataa    6240
aaaagtctat tagccatttc ctgcaaatgg acaattatca cttcttccat tttccttggt    6300
gataaaacat ggtggttagg cctgggtcag tctctcctgt gaccagcact ggagctgtgt    6360
gagagggctc tagtcctgat ggcatgttga ttctttattt ctagagacca acttgaggca    6420
catctgtaaa cggataatgg acatggtgag caaccagcac ccctggtttg gaatggagca    6480
ggaatatact cttatgggaa cagacggcca cccatttggt tggccttcca atggcttccc    6540
tggaccccaa ggtacgtccc actgggtaaa gggtgaaact tcctccccta agttgttact    6600
gtccaggaaa tccccttccc cagagatagg tgcaatcctg aaatgagaaa atggagacca    6660
```

```
gcagcagaat cttaacagta gaccgacctt gcatccctca catccagagg tggttagaat    6720
ttaaagtgac agagagtggt gagatggctc agtggttacc caccaggcct gacaacctga    6780
atctcctcct gggacccatt tggtagaagg caagaaatga ctccctcaag ttagcctctg    6840
accatactgt aaatatgcaa gtacacacaa aactaatgaa aagccactca aaaaaagcaa    6900
gcagggcctc taccgaggcc gaggcaaaga aggaatgacc taaattctcc cgcctgcagc    6960
tgaaggcagg actagtgact caggaaagca ggtttaggcc ctcctagttt tgggctttgg    7020
ggtttcctgg attccctgac tgactcttcc ctgctgtgtc ttgaacctcc ttcaggcccg    7080
tattactgcg gtgtgggagc agacaaggcc tacggcaggg acatcgtgga ggctcactac    7140
cgggcctgct tgtatgctgg agtcaagatt acggggacaa atgcggaggt tatgcctgcc    7200
caggtaaatg gtgcccatct ttttcctcct ctctgaagac ctgggtaggt aggcacatgg    7260
ggacttcggg ctagcagggg tggatcacaa agtggggcaa tcacagaggg tggatcttaa    7320
aggtcaactt tttctctcta gtgggaattc cagataggac cctgtgaggg gatccgaatg    7380
ggagatcatc tttggatagc ccgttttatc ttgcatcggg tgtgcgaaga ctttggggtg    7440
atagcaacct ttgaccccaa gcccattcca gggaactgga atggtgcagg ctgccatacc    7500
aacttcagca ccaaggccat gcgggaggag aatggtctga gtaagtacc ttcctttgga    7560 gccgtctgta ttctcatggg gtagaagggc tttgggtact cacaaggctg tacgtacatg    7620
cctagctctg catatttgtt ctaagcctgt cagtttgtgc ctgttggaga ggcgataggg    7680
taaatacttt aggaatagaa ttgacagaaa agcattcgaa ctaagtaaaa atacaagcaa    7740
atgggaaact taattcttac tggtgggaag aggcgagtga ttgggggtct ttccatccag    7800
tggataattt gcactgcatg ttaaagactg gcctgaggga gacagtgcct tctttcttct    7860
gggattcatg cccgctccca tccttgtcga tggaccctca tcttcactgt ttccactagg    7920
tgcattgagg aggccattga caaactgagc aagaggcacc agtaccacat tcgcgcctac    7980
gatcccaagg ggggcctgga caacgcccgg cgtctgactg gattccacga aacctccaac    8040
atcaacgact tttctgccgg tgttgccaac cgcggtgcca gtatccgcat tccccggact    8100
gtcggccagg agaagaaggg ctactttgaa gaccgtcggc cttctgccaa ttgtgacccc    8160
tatgcggtga cagaagccat cgtccgcacg tgtctcctca acgaaacagg cgacgaaccc    8220
ttccaataca agaactaagt ggactagact tccagtgatc cctctcccag ctcttccctt    8280
tcccagttgt ccccactgta actcaaaagg atggaatacc aaggtctttt tattcctcgt    8340
gcccagttaa tcttgctttt gttggtcaga atagagggt caggttctta atctctacac    8400
accaaccctt tctttcctat ctagctttct agtagggagc gggaggggg aggggaaggg    8460 taacccactg cttcatctca tcgggtatgc atgtccggta ggcatagctg tcacaaagcg    8520
ggtgtactta tggtgaaaga ggacattttt tttttcttca ggatagttga aagggcaggc    8580
ccaacggctg agattgacat ttccactgtt ggtagagagc tgttattct aaaggggaaa    8640 ccagctttct gttccaaatg gaagttaggt gaggagttga aggttggttt cttgcgctgt    8700
gcttccttgg cttggggag ggggcatccg tccccctctg tgtgaacaca gctcaccgcg    8760
tcacctgatg gatggcccta ctgtgaagga agaaaaaagt tggcatttct tggtcctccg    8820
ttcataacac aaagcagagt agtattttta tatttaaatg ttaaaaacaa aaagttata    8880 tatatatgga tgtgtggatg tatgtctttc taattgagag aaccatccta ttcactgggt    8940 gccaagttg agtgatgagg ggcttggctt agaagtgagg ctcccttgag gtaggggtga    9000
ggatgcagta ccgggaaagt tggttatctt ggggtctcag cttcattact gcttagggtt    9060
```

```
tccctgccca ctctgcagga gcagatgttg dacaggtagc cagtgggatg ccactgcttg    9120
ccaccacctg tccccaggct taggtttagg ggatgcgtat acttactcca cacacgagtt    9180
agaagtatga gttggctggt caacttgaac actgttactg atgggtgggt gggtgggggt    9240
ttactggggt tattttttg gtgggattag catgtcacta aagcgggcct tttgatatat    9300 taagttttt aaaagcaaaa caagtttaga ttttaatcag atttgtaggg tttctaactt    9360
tacagaattg cctgtttgtt tcaatgtctc cctccacttg gctcttaggg gaattaagga    9420
caggcctaga gttaaaacac ttgtctccta gtgtcacctc tgccagcaga ctgttacttt    9480
ccttctgaaa aagccaatag tctttttttt tttcttttat agtaaacaca cccccacctc    9540
catcccagcc tgttgcccct cagttttctg gttgtttgtg tcggcagcgg gccaactgtg    9600
gtttctctct tgccatgatg acttctaatt gccatgtata gtatgttcgg ttagataact    9660
cactgtaaac agactgtaac tgccaggcag cgcttataaa tcaacctaac atttataaga    9720
tttcctctga cttgtttctt tgtggttccc aaaaaaaaaa aaaaaacctc                9770
```

<210> SEQ ID NO 4
<211> LENGTH: 167
<212> TYPE: PRT
<213> ORGANISM: artificial sequence
<220> FEATURE:
<223> OTHER INFORMATION: ICreI N75 scaffold protein

<400> SEQUENCE: 4

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Tyr Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Arg Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 5
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 5

```
ccatgaccac ctcagcaagt tccc                                             24
```

```
<210> SEQ ID NO 6
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 6
catgtatatc tggatcgatg gtac                                    24

<210> SEQ ID NO 7
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 7
tgtatatctg gatcgatggt actg                                    24

<210> SEQ ID NO 8
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 8
tctggatcga tggtactgga gaag                                    24

<210> SEQ ID NO 9
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 9
ccggaccctg gacagtgagc ccaa                                    24

<210> SEQ ID NO 10
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 10
cctggacagt gagcccaagt gtgt                                    24

<210> SEQ ID NO 11
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 11
aggaccctaa caagctggtg ttat                                    24

<210> SEQ ID NO 12
<211> LENGTH: 24
<212> TYPE: DNA
<213> ORGANISM: artificial sequence
<220> FEATURE:
```

<223> OTHER INFORMATION: human Glutamine Synthetase gene target

<400> SEQUENCE: 12
tataccctca tggggacaga tggg                                          24

<210> SEQ ID NO 13
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 13
tgggcacccc tttggttggc cttc                                          24

<210> SEQ ID NO 14
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 14
gcttcccagg gccccagggt aagt                                          24

<210> SEQ ID NO 15
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 15
tcctgatgct tctgtaggtc cata                                          24

<210> SEQ ID NO 16
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 16
cggggactaa tgccgaggtc atgc                                          24

<210> SEQ ID NO 17
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 17
tcatgcctgc ccaggtaagt atag                                          24

<210> SEQ ID NO 18
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 18
agcaaccttt gatcctaagc ccat                                          24

```
<210> SEQ ID NO 19
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 19
caaggccatg cgggaggaga atgg                                          24

<210> SEQ ID NO 20
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 20
cttttctgtt tactctaggt acat                                          24

<210> SEQ ID NO 21
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 21
gtaccacatc cgtgcctatg atcc                                          24

<210> SEQ ID NO 22
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 22
ccgtgcctat gatcccaagg gagg                                          24

<210> SEQ ID NO 23
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 23
cctggacaat gcccgacgtc taac                                          24

<210> SEQ ID NO 24
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 24
gcccgacgtc taactggatt ccat                                          24

<210> SEQ ID NO 25
<211> LENGTH: 24
<212> TYPE: DNA
<213> ORGANISM: artificial sequence
<220> FEATURE:
<223> OTHER INFORMATION: human Glutamine Synthetase gene target
```

```
<400> SEQUENCE: 25
ttctgctggt gtagccaatc gtag                                          24

<210> SEQ ID NO 26
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 26
gcattccccg gactgttggc cagg                                          24

<210> SEQ ID NO 27
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 27
ccggactgtt ggccaggaga agaa                                          24

<210> SEQ ID NO 28
<211> LENGTH: 24
<212> TYPE: DNA
<213> ORGANISM: artificial sequence
<220> FEATURE:
<223> OTHER INFORMATION: human Glutamine Synthetase gene target

<400> SEQUENCE: 28
gttggccagg agaagaaggg ttac                                          24

<210> SEQ ID NO 29
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 29
catggccacc tcagcaagtt ccca                                          24

<210> SEQ ID NO 30
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 30
ctgccccagg gtgagaaagt ccaa                                          24

<210> SEQ ID NO 31
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 31
tgtatatctg ggttgatggt accg                                          24

<210> SEQ ID NO 32
<211> LENGTH: 24
```

```
<212> TYPE: DNA
<213> ORGANISM: artificial sequence
<220> FEATURE:
<223> OTHER INFORMATION: mouse Glutamine Synthetase gene target

<400> SEQUENCE: 32
ccgtaccctg gactgtgagc ccaa                                              24

<210> SEQ ID NO 33
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 33
cggaaacctg caggcaagta tggg                                              24

<210> SEQ ID NO 34
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 34
agcaaccagc acccctggtt tgga                                              24

<210> SEQ ID NO 35
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 35
ctcttatggg aacagacggc cacc                                              24

<210> SEQ ID NO 36
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 36
gcttccctgg accccaaggt acgt                                              24

<210> SEQ ID NO 37
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 37
cggggacaaa tgcggaggtt atgc                                              24

<210> SEQ ID NO 38
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 38
```

```
gcctgcccag gtaaatggtg ccca                                              24

<210> SEQ ID NO 39
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 39
gtcaactttt tctctctagt ggga                                              24

<210> SEQ ID NO 40
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 40
taggaccctg tgagggatc cgaa                                               24

<210> SEQ ID NO 41
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 41
tttggatagc ccgtttatc ttgc                                               24

<210> SEQ ID NO 42
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 42
gttttatctt gcatcgggtg tgcg                                              24

<210> SEQ ID NO 43
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 43
tttatcttgc atcgggtgtg cgaa                                              24

<210> SEQ ID NO 44
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 44
tcgcgcctac gatcccaagg gggg                                              24

<210> SEQ ID NO 45
<211> LENGTH: 24
<212> TYPE: DNA
<213> ORGANISM: artificial sequence
```

```
<220> FEATURE:
<223> OTHER INFORMATION: mouse Glutamine Synthetase gene target

<400> SEQUENCE: 45
cctggacaac gcccggcgtc tgac                                         24

<210> SEQ ID NO 46
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 46
gcattccccg gactgtcggc cagg                                         24

<210> SEQ ID NO 47
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 47
ccggactgtc ggccaggaga agaa                                         24

<210> SEQ ID NO 48
<211> LENGTH: 24
<212> TYPE: DNA
<213> ORGANISM: artificial sequence
<220> FEATURE:
<223> OTHER INFORMATION: mouse Glutamine Synthetase gene target

<400> SEQUENCE: 48
gtcggccagg agaagaaggg ctac                                         24

<210> SEQ ID NO 49
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 49
tgtatatctg ggttgatggt actg                                         24

<210> SEQ ID NO 50
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 50
ccgcaccctg gactgtgagc ccaa                                         24

<210> SEQ ID NO 51
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 51
```
ctcagccctg ttgccatgtt tcgg                                          24

<210> SEQ ID NO 52
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 52
cgggacccct tccgcagaga tccc                                          24

<210> SEQ ID NO 53
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 53
tgggcaccct tttggttggc cttc                                          24

<210> SEQ ID NO 54
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 54
caaagcctat ggcagggata tcgt                                          24

<210> SEQ ID NO 55
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 55
caggaacaaa tgctgaggtc atgc                                          24

<210> SEQ ID NO 56
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 56
ttcatcttgc atcgagtatg tgaa                                          24

<210> SEQ ID NO 57
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 57

```
tcgagcctac gatcccaagg gggg                                              24
```

<210> SEQ ID NO 58
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 58

```
cctggacaat gcccgtggtc tgac                                              24
```

<210> SEQ ID NO 59
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 59

```
ttctgctggt gtcgccaatc gcag                                              24
```

<210> SEQ ID NO 60
<211> LENGTH: 24
<212> TYPE: DNA
<213> ORGANISM: artificial sequence
<220> FEATURE:
<223> OTHER INFORMATION: Chinese Hamster Glutamine Synthetase gene
      target

<400> SEQUENCE: 60

```
gtcggccagg agaagaaagg ttac                                              24
```

<210> SEQ ID NO 61
<211> LENGTH: 163
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 61

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser Gly Phe Lys His Gln Leu Ser Leu Thr Phe Val Thr Gln Lys Thr
        35                  40                  45

Gln Arg Arg Trp Phe Leu Asp Lys Leu Val Asp Glu Ile Gly Val Gly
    50                  55                  60

Tyr Val Glu Arg Gly Ser Val Ser Asn Tyr Arg Ser Lys Ile Lys Pro
65                  70                  75                  80

Leu His Asn Phe Leu Thr Gln Leu Gln Pro Phe Leu Lys Leu Lys Gln
                85                  90                  95

Lys Gln Ala Asn Leu Val Leu Lys Ile Ile Glu Gln Leu Pro Ser Ala
            100                 105                 110

Lys Glu Ser Pro Asp Lys Phe Leu Glu Val Cys Thr Trp Val Asp Gln
        115                 120                 125

Ile Ala Ala Leu Asn Asp Ser Lys Thr Arg Lys Thr Thr Ser Glu Thr
    130                 135                 140
```

Val Arg Ala Val Leu Asp Ser Leu Ser Glu Lys Lys Ser Ser Pro
145                 150                 155                 160

Ala Ala Asp

<210> SEQ ID NO 62
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 62

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Gly Cys Lys Phe Lys His Ala Leu Ser Leu Thr Phe Ile Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ser Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 63
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 63

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Thr Cys Lys Phe Lys His Gln Leu Thr Leu Thr Phe Lys Val Thr Gln
            35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Glu Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln

```
                100                 105                 110
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 64
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 64

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Thr Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 65
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 65

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asn Leu Gln Leu Thr Phe Arg Val Thr Gln
        35                  40                  45

Lys Thr Gln Arg Arg Trp Phe Leu Asp Lys Leu Val Asp Glu Ile Gly
```

```
                50                  55                  60
Val Gly Tyr Val Tyr Asp Ser Gly Ser Val Ser Glu Tyr Val Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 66
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 66

```
Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
                 20                  25                  30

Thr Cys Lys Phe Lys His Gln Leu Ser Leu Thr Phe Leu Val Thr Gln
                 35                  40                  45

Lys Thr Gln Arg Arg Trp Phe Leu Asp Lys Leu Val Asp Glu Ile Gly
 50                  55                  60

Val Gly Tyr Val Arg Asp Ala Gly Ser Val Ser Asn Tyr Val Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 67
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 67

Met Ala Asn Thr Lys Tyr Asn Lys Glu Phe Leu Leu Tyr Leu Ala Gly

```
            1               5                  10                 15
         Phe Val Asp Gly Asp Gly Ser Ile Ile Ala Gln Ile Lys Pro Asn Gln
                       20                 25                 30

His His Lys Phe Lys His Gln Leu Ser Leu Thr Phe Asn Val Thr Gln
                       35                 40                 45

Lys Thr Gln Arg Arg Trp Phe Leu Asp Lys Leu Val Asp Glu Ile Gly
                       50                 55                 60

Val Gly Tyr Val Gln Asp Ser Gly Ser Val Ser Tyr Val Leu Ser
          65                 70                 75                 80

Glu Ile Lys Pro Leu His Asn Phe Leu Thr Gln Leu Gln Pro Phe Leu
                       85                 90                 95

Lys Leu Lys Gln Lys Gln Ala Asn Leu Val Leu Lys Ile Ile Glu Gln
                      100                105                110

Leu Pro Ser Ala Lys Glu Ser Pro Asp Lys Phe Leu Glu Val Cys Thr
                      115                120                125

Trp Val Asp Gln Ile Ala Ala Leu Asn Asp Ser Lys Thr Arg Lys Thr
                      130                135                140

Thr Ser Glu Thr Val Arg Ala Val Leu Asp Ser Leu Ser Glu Lys Lys
         145                150                155                160

Lys Ser Ser Pro Ala Ala Asp
                      165

<210> SEQ ID NO 68
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 68

Met Ala Asn Thr Lys Tyr Asn Lys Glu Phe Leu Leu Tyr Leu Ala Gly
          1               5                  10                 15

Phe Val Asp Gly Asp Gly Ser Ile Ile Ala Gln Ile Lys Pro Arg Gln
                       20                 25                 30

Cys Cys Lys Phe Lys His Gln Leu Glu Leu Thr Phe Lys Val Thr Gln
                       35                 40                 45

Lys Thr Gln Arg Arg Trp Phe Leu Asp Lys Leu Val Asp Glu Ile Gly
                       50                 55                 60

Val Gly Tyr Val Thr Asp Thr Gly Ser Val Ser Asn Tyr Ile Leu Ser
          65                 70                 75                 80

Glu Ile Lys Pro Leu His Asn Phe Leu Thr Gln Leu Gln Pro Phe Leu
                       85                 90                 95

Lys Leu Lys Gln Lys Gln Ala Asn Leu Val Leu Lys Ile Ile Glu Gln
                      100                105                110

Leu Pro Ser Ala Lys Glu Ser Pro Asp Lys Phe Leu Glu Val Cys Thr
                      115                120                125

Trp Val Asp Gln Ile Ala Ala Leu Asn Asp Ser Lys Thr Arg Lys Thr
                      130                135                140

Thr Ser Glu Thr Val Arg Ala Val Leu Asp Ser Leu Ser Glu Lys Lys
         145                150                155                160

Lys Ser Ser Pro Ala Ala Asp
                      165

<210> SEQ ID NO 69
<211> LENGTH: 167
```

```
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 69

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Tyr Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Glu Asp Ser Gly Ser Val Ser Arg Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 70
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 70

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Thr Lys Phe Lys His Gln Leu Ser Leu Thr Phe Ala Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140
```

```
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 71
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 71

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
                20                  25                  30

Ser Arg Lys Phe Lys His Thr Leu Ser Leu Thr Phe Arg Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Asn Tyr Asp Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 72
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 72

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

His His Lys Phe Lys His Gln Leu Ser Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Ser Tyr Thr Leu Ser
65                  70                  75                  80

Glu Ile Lys Pro Leu His Asn Phe Leu Thr Gln Leu Gln Pro Phe Leu
                85                  90                  95
```

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 73
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 73

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser Gly Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 74
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 74

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Lys Val Thr Gln
        35                  40                  45
```

```
Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 75
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 75

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Ser Gln
                20                  25                  30

Ser His Lys Phe Lys His Lys Leu Ser Leu Thr Phe Ile Val Thr Gln
            35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 76
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 76

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Gln Leu Thr Leu Thr Phe Gln Val Thr Gln
            35                  40                  45

Lys Thr Gln Arg Arg Trp Phe Leu Asp Lys Leu Val Asp Glu Ile Gly
50                  55                  60

Val Gly Tyr Val Asn Asp Ser Gly Ser Val Ser Gln Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 77
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 77

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asp Leu Arg Leu Thr Phe Ile Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Cys Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 78

```
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 78

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Pro Lys Phe Lys His Lys Leu Ser Leu Thr Phe Asn Val Thr Gln
            35                  40                  45

Lys Thr Gln Arg Arg Trp Phe Leu Asp Lys Leu Val Asp Glu Ile Gly
        50                  55                  60

Val Gly Tyr Val Lys Asp His Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 79
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 79

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His Ala Leu Ser Leu Thr Phe Ile Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ala Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140
```

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 80
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 80

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Thr Tyr Lys Phe Lys His Trp Leu Ser Leu Thr Phe Ala Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Arg Tyr Leu Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 81
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 81

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
                20                  25                  30

Ser Arg Lys Phe Lys His Ser Leu Ser Leu Thr Phe Tyr Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asp Tyr Val Leu Ser
65                  70                  75                  80

Glu Ile Lys Pro Leu His Asn Phe Leu Thr Gln Leu Gln Pro Phe Leu
                85                  90                  95

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 82
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 82

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser Gly Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Asp Tyr Lys Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 83
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 83

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asn Leu Gln Leu Thr Phe Ser Val Thr Gln
        35                  40                  45
```

Lys Thr Gln Arg Arg Trp Phe Leu Asp Lys Leu Val Asp Glu Ile Gly
            50                  55                  60

Val Gly Tyr Val Arg Asp Ser Gly Ser Val Ser Tyr Tyr Thr Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 84
<211> LENGTH: 167
<212> TYPE: PRT
<213> ORGANISM: artificial sequence
<220> FEATURE:
<223> OTHER INFORMATION: First I-CreI variant cleaving human Glutamine
      Synthetase gene target

<400> SEQUENCE: 84

Met Ala Asn Thr Lys Tyr Asn Lys Glu Phe Leu Leu Tyr Leu Ala Gly
 1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Ala Val Thr Gln
                35                  40                  45

Lys Thr Gln Arg Arg Trp Phe Leu Asp Lys Leu Val Asp Glu Ile Gly
            50                  55                  60

Val Gly Tyr Val Arg Asp Ser Gly Ser Val Ser Glu Tyr Arg Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 85
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 85

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Thr Asn Lys Phe Lys His Gln Leu Gln Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Thr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 86
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 86

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asp Leu Arg Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Ser Gly Ser Val Ser Arg Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 87
<211> LENGTH: 167
<212> TYPE: PRT
<213> ORGANISM: artificial sequence
<220> FEATURE:
<223> OTHER INFORMATION: Second I-CreI variant cleaving human Glutamine Synthetase gene target

<400> SEQUENCE: 87

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Thr Asn Lys Phe Lys His Gln Leu Gln Leu Thr Phe Leu Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 88
<211> LENGTH: 167
<212> TYPE: PRT
<213> ORGANISM: artificial sequence
<220> FEATURE:
<223> OTHER INFORMATION: Second I-CreI variant cleaving human Glutamine Synthetase gene target

<400> SEQUENCE: 88

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Ala Leu Ser Leu Thr Phe Met Val Thr Gln
        35                  40                  45

Lys Thr Gln Arg Arg Trp Phe Leu Asp Lys Leu Val Asp Glu Ile Gly
    50                  55                  60

Val Gly Tyr Val Glu Asp Arg Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr

```
                130              135                140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 89
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 89

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
                20                  25                  30

Ser Arg Lys Phe Lys His Arg Leu Lys Leu Thr Phe Asn Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 90
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 90

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Tyr Gln
                20                  25                  30

Thr Cys Lys Phe Lys His Gln Leu Ser Leu Thr Phe Asp Val Thr Gln
            35                  40                  45

Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Ser Tyr Arg Leu Ser
65                  70                  75                  80

Glu Ile Lys Pro Leu His Asn Phe Leu Thr Gln Leu Gln Pro Phe Leu
```

```
                    85                  90                  95
Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 91
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 91

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Glu Lys Phe Lys His Gln Leu Glu Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Lys Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 92
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 92

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Arg Asp Lys Phe Lys His Gln Leu Ser Leu Thr Phe Ala Val Thr Gln
```

```
                35                  40                  45
Lys Thr Gln Arg Arg Trp Phe Leu Asp Lys Leu Val Asp Glu Ile Gly
        50                  55                  60

Val Gly Tyr Val Arg Asp Ser Gly Ser Val Ser Arg Tyr Leu Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 93
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 93

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Ser Gln
            20                  25                  30

Ser His Lys Phe Lys His Lys Leu Ser Leu Thr Phe Asn Val Thr Gln
            35                  40                  45

Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 94
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 94

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Pro Lys Phe Lys His Gln Leu Gln Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Glu Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 95
<211> LENGTH: 167
<212> TYPE: PRT
<213> ORGANISM: artificial sequence
<220> FEATURE:
<223> OTHER INFORMATION: Second I-CreI variant cleaving human Glutamine Synthetase gene target

<400> SEQUENCE: 95

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Cys Cys Lys Phe Lys His His Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Asp Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

-continued

<210> SEQ ID NO 96
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 96

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser Gly Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Tyr Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 97
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 97

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

```
Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 98
<211> LENGTH: 167
<212> TYPE: PRT
<213> ORGANISM: artificial sequence
<220> FEATURE:
<223> OTHER INFORMATION: Second I-CreI variant cleaving human Glutamine Synthetase gene target

<400> SEQUENCE: 98

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Glu Pro Asn Gln
            20                  25                  30

Ser Arg Lys Phe Lys His Arg Leu Lys Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Gln Tyr Asn Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 99
<211> LENGTH: 167
<212> TYPE: PRT
<213> ORGANISM: artificial sequence
<220> FEATURE:
<223> OTHER INFORMATION: Second I-CreI variant cleaving human Glutamine Synthetase gene target

<400> SEQUENCE: 99

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asp Tyr Lys Phe Lys His Cys Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Glu Asp Ser Gly Ser Val Ser Asn Tyr Arg Leu Ser
65                  70                  75                  80
```

```
Glu Ile Lys Pro Leu His Asn Phe Leu Thr Gln Leu Gln Pro Phe Leu
             85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135             140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 100
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 100

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Ala Val Thr Gln
            35                  40                  45

Lys Thr Gln Arg Arg Trp Phe Leu Asp Lys Leu Val Asp Glu Ile Gly
 50                 55                  60

Val Gly Tyr Val Gln Asp Asn Gly Ser Val Ser Asn Tyr Ile Leu Ser
 65                 70                  75                  80

Glu Ile Lys Pro Leu His Asn Phe Leu Thr Gln Leu Gln Pro Phe Leu
             85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135             140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 101
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 101

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30
```

```
Ala Asn Lys Phe Lys His Gln Leu Glu Leu Thr Phe Ala Val Thr Gln
            35                  40                  45

Lys Thr Gln Arg Arg Trp Phe Leu Asp Lys Leu Val Asp Glu Ile Gly
 50                  55                  60

Val Gly Tyr Val Arg Asp Ser Gly Ser Val Ser Glu Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 102
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 102

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Arg Pro Asn Gln
                 20                  25                  30

Ser Ala Lys Phe Lys His Tyr Leu Gln Leu Thr Phe Asp Val Thr Gln
            35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Ser Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 103
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target
```

<400> SEQUENCE: 103

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Thr Cys Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser His Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 104
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 104

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Arg Lys Phe Lys His Asn Leu Gln Leu Thr Phe Tyr Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Ser Gly Ser Val Ser Ser Tyr Asp Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 105
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 105

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Tyr Lys Phe Lys His Trp Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Ser Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 106
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 106

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Asn Pro Asn Gln
            20                  25                  30

Ser Ser Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 107
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 107

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Arg Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Glu Asp Ser Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 108
<211> LENGTH: 167
<212> TYPE: PRT
<213> ORGANISM: artificial sequence
<220> FEATURE:
<223> OTHER INFORMATION: Second I-CreI variant cleaving human Glutamine
      Synthetase gene target

<400> SEQUENCE: 108

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Arg Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
              100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 109
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 109

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Cys Cys Lys Phe Lys His His Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
              100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 110
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 110

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Tyr Tyr Gln Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 111
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 111

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro His Gln
                 20                  25                  30

His Cys Lys Phe Lys His Gln Leu Thr Leu Thr Phe Arg Val Thr Gln
                 35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Glu Tyr Val Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 112
<211> LENGTH: 167
<212> TYPE: PRT
<213> ORGANISM: artificial sequence
<220> FEATURE:
<223> OTHER INFORMATION: First I-CreI variant cleaving mouse Glutamine -continued Synthetase gene target

<400> SEQUENCE: 112

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 113
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 113

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Arg Lys Phe Lys His Gln Leu Ala Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp

<210> SEQ ID NO 114
<211> LENGTH: 167
<212> TYPE: PRT
<213> ORGANISM: artificial sequence
<220> FEATURE:
<223> OTHER INFORMATION: First I-CreI variant cleaving mouse Glutamine
       Synthetase gene target

<400> SEQUENCE: 114

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gln Leu Ser Leu Thr Phe Leu Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Asn Gly Ser Val Ser Asn Tyr Ile Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 115
<211> LENGTH: 167
<212> TYPE: PRT
<213> ORGANISM: artificial sequence
<220> FEATURE:
<223> OTHER INFORMATION: First I-CreI variant cleaving mouse Glutamine
       Synthetase gene target

<400> SEQUENCE: 115

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Arg Lys Phe Lys His Gln Leu Ser Leu Thr Phe Tyr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asp Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr

```
                 115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 116
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 116

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Thr Lys Phe Lys His Gln Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Ser Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 117
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 117

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

His His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Ser Gly Ser Val Ser Asn Tyr Arg Leu Ser
```

```
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 118
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 118

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Arg Lys Phe Lys His Thr Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Lys Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 119
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 119

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
```

```
                    20                  25                  30
Ser Cys Lys Phe Lys His Gln Leu Gln Leu Thr Phe Gln Val Thr Gln
                35                  40                  45

Lys Thr Gln Arg Arg Trp Phe Leu Asp Lys Leu Val Asp Glu Ile Gly
         50                  55                  60

Val Gly Tyr Val Arg Asp Ser Gly Ser Val Ser Asn Tyr Arg Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 120
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 120

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Arg Gln
                20                  25                  30

Ser Tyr Lys Phe Lys His Gln Leu Ser Leu Thr Phe Arg Val Thr Gln
                35                  40                  45

Lys Thr Gln Arg Arg Trp Phe Leu Asp Lys Leu Val Asp Glu Ile Gly
         50                  55                  60

Val Gly Tyr Val Tyr Asp Ser Gly Ser Val Ser Glu Tyr Gln Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 121
<211> LENGTH: 167
<212> TYPE: PRT
<213> ORGANISM: artificial sequence
<220> FEATURE:
```

<223> OTHER INFORMATION: First I-CreI variant cleaving mouse Glutamine
     Synthetase gene target

<400> SEQUENCE: 121

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Cys Lys Phe Lys His Ala Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 122
<211> LENGTH: 167
<212> TYPE: PRT
<213> ORGANISM: artificial sequence
<220> FEATURE:
<223> OTHER INFORMATION: First I-CreI variant cleaving mouse Glutamine
     Synthetase gene target

<400> SEQUENCE: 122

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Ser Lys Phe Lys His Arg Leu Asp Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160
```

Lys Ser Ser Pro Ala Ala Asp
            165

<210> SEQ ID NO 123
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 123

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Cys Lys Phe Lys His Gln Leu Ser Leu Thr Phe Glu Val Thr Gln
        35                  40                  45

Lys Thr Gln Arg Arg Trp Phe Leu Asp Lys Leu Val Asp Glu Ile Gly
    50                  55                  60

Val Gly Tyr Val Cys Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 124
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 124

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser His Lys Phe Lys His Arg Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

```
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 125
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 125

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Ser Gln
            20                  25                  30

Ser Ser Lys Phe Lys His His Leu Ser Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 126
<211> LENGTH: 167
<212> TYPE: PRT
<213> ORGANISM: artificial sequence
<220> FEATURE:
<223> OTHER INFORMATION: First I-CreI variant cleaving mouse Glutamine
      Synthetase gene target

<400> SEQUENCE: 126

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Arg Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60
```

```
Val Gly Tyr Val Glu Asp Ser Gly Ser Val Ser Asp Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 127
<211> LENGTH: 167
<212> TYPE: PRT
<213> ORGANISM: artificial sequence
<220> FEATURE:
<223> OTHER INFORMATION: First I-CreI variant cleaving mouse Glutamine Synthetase gene target

<400> SEQUENCE: 127

```
Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Asn Gln
                 20                  25                  30

Ser Arg Lys Phe Lys His Asn Leu Gln Leu Thr Phe Ala Val Thr Gln
             35                  40                  45

Lys Thr Gln Arg Arg Trp Phe Leu Asp Lys Leu Val Asp Glu Ile Gly
         50                  55                  60

Val Gly Tyr Val Arg Asp Ser Gly Ser Val Ser Arg Tyr Leu Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 128
<211> LENGTH: 167
<212> TYPE: PRT
<213> ORGANISM: artificial sequence
<220> FEATURE:
<223> OTHER INFORMATION: First I-CreI variant cleaving mouse Glutamine Synthetase gene target

<400> SEQUENCE: 128

```
Met Ala Asn Thr Lys Tyr Asn Lys Glu Phe Leu Leu Tyr Leu Ala Gly
  1               5                  10                  15
```

```
Phe Val Asp Gly Asp Gly Ser Ile Ile Ala Gln Ile Lys Pro Gly Gln
            20                  25                  30

Ser Tyr Lys Phe Lys His Lys Leu Ser Leu Thr Phe Thr Val Thr Gln
            35                  40                  45

Lys Thr Gln Arg Arg Trp Phe Leu Asp Lys Leu Val Asp Glu Ile Gly
 50                  55                  60

Val Gly Tyr Val Arg Asp Ser Gly Ser Val Ser Glu Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 129
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 129

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Arg Gln
            20                  25                  30

Ser Tyr Lys Phe Lys His Gln Leu Ser Leu Thr Phe Thr Val Thr Gln
            35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Arg Tyr Thr Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 130
<211> LENGTH: 167
<212> TYPE: PRT
<213> ORGANISM: artificial sequence
```

```
<220> FEATURE:
<223> OTHER INFORMATION: Second I-CreI variant cleaving mouse Glutamine
      Synthetase gene target

<400> SEQUENCE: 130

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 131
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 131

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160
```

Lys Ser Ser Pro Ala Ala Asp
            165

<210> SEQ ID NO 132
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 132

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Lys Val Thr Gln
            35                  40                  45

Lys Thr Gln Arg Arg Trp Phe Leu Asp Lys Leu Val Asp Glu Ile Gly
    50                  55                  60

Val Gly Tyr Val Asn Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 133
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 133

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Cys Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
    50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 134
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 134

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Thr Asn Lys Phe Lys His Gln Leu Gln Leu Thr Phe Ile Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Cys Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 135
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 135

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser His Lys Phe Lys His Ala Leu Ser Leu Thr Phe Val Val Thr Gln
        35                  40                  45

Lys Thr Gln Arg Arg Trp Phe Leu Asp Lys Leu Val Asp Glu Ile Gly
    50                  55                  60

Val Gly Tyr Val Glu Asp Arg Gly Ser Val Ser Asn Tyr Arg Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 136
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 136

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Arg Asp Lys Phe Lys His Gln Leu Ser Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Thr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 137
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 137

Met Ala Asn Thr Lys Tyr Asn Lys Glu Phe Leu Leu Tyr Leu Ala Gly
1               5                   10                  15

```
Phe Val Asp Gly Asp Gly Ser Ile Val Ala Gln Ile Lys Pro Asn Gln
            20                  25                  30

Ser Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Asn Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 138
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 138

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
            20                  25                  30

His Cys Lys Phe Lys His Ala Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 139
<211> LENGTH: 167
<212> TYPE: PRT
```

<213> ORGANISM: artificial sequence
<220> FEATURE:
<223> OTHER INFORMATION: Second I-CreI variant cleaving mouse Glutamine
      Synthetase gene target

<400> SEQUENCE: 139

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Ala Leu Gln Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Ser Gly Ser Val Ser Gln Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 140
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 140

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Gly Lys Phe Lys His Gln Leu Gln Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys

```
145                 150                 155                 160
Lys Ser Ser Pro Ala Ala Asp
                165

<210> SEQ ID NO 141
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 141

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Thr Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Ser Asp Ser Gly Ser Val Ser Asn Tyr Thr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 142
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 142

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Asp Tyr Lys Phe Lys His Tyr Leu Ser Leu Thr Phe Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
```

```
              100                 105                 110
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 143
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 143

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Arg Leu Lys Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Ser Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 144
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 144

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Thr Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
```

```
            50                  55                  60
Val Gly Tyr Val His Asp Ser Gly Ser Val Ser Asn Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 145
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 145

```
Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
                 20                  25                  30

Ser Tyr Lys Phe Lys His Gln Leu Ser Leu Thr Phe Lys Val Thr Gln
             35                  40                  45

Lys Thr Gln Arg Arg Trp Phe Leu Asp Lys Leu Val Asp Glu Ile Gly
         50                  55                  60

Val Gly Tyr Val Glu Asp Ser Gly Ser Val Ser Asp Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 146
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 146

Met Ala Asn Thr Lys Tyr Asn Lys Glu Phe Leu Leu Tyr Leu Ala Gly

```
            1               5                  10                 15
         Phe Val Asp Gly Asp Gly Ser Ile Ile Ala Gln Ile Lys Pro Asn Gln
                         20                 25                 30

Asn Gly Lys Phe Lys His Gln Leu Ser Leu Thr Phe Lys Val Thr Gln
                         35                 40                 45

Lys Thr Gln Arg Arg Trp Phe Leu Asp Lys Leu Val Asp Glu Ile Gly
                         50                 55                 60

Val Gly Tyr Val Tyr Asp Ser Gly Ser Val Ser Asn Tyr Ile Leu Ser
         65                         70                 75                 80

Glu Ile Lys Pro Leu His Asn Phe Leu Thr Gln Leu Gln Pro Phe Leu
                         85                 90                 95

Lys Leu Lys Gln Lys Gln Ala Asn Leu Val Leu Lys Ile Ile Glu Gln
                         100                105                110

Leu Pro Ser Ala Lys Glu Ser Pro Asp Lys Phe Leu Glu Val Cys Thr
                         115                120                125

Trp Val Asp Gln Ile Ala Ala Leu Asn Asp Ser Lys Thr Arg Lys Thr
                         130                135                140

Thr Ser Glu Thr Val Arg Ala Val Leu Asp Ser Leu Ser Glu Lys Lys
         145                        150                155                160

Lys Ser Ser Pro Ala Ala Asp
                         165

<210> SEQ ID NO 147
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 147

Met Ala Asn Thr Lys Tyr Asn Lys Glu Phe Leu Leu Tyr Leu Ala Gly
         1               5                  10                 15

Phe Val Asp Gly Asp Gly Ser Ile Ile Ala Gln Ile Lys Pro Asn Gln
                         20                 25                 30

Thr Tyr Lys Phe Lys His Trp Leu Ser Leu Thr Phe Asp Val Thr Gln
                         35                 40                 45

Lys Thr Gln Arg Arg Trp Phe Leu Asp Lys Leu Val Asp Glu Ile Gly
                         50                 55                 60

Val Gly Tyr Val Tyr Asp Ser Gly Ser Val Ser Asp Tyr Arg Leu Ser
         65                         70                 75                 80

Glu Ile Lys Pro Leu His Asn Phe Leu Thr Gln Leu Gln Pro Phe Leu
                         85                 90                 95

Lys Leu Lys Gln Lys Gln Ala Asn Leu Val Leu Lys Ile Ile Glu Gln
                         100                105                110

Leu Pro Ser Ala Lys Glu Ser Pro Asp Lys Phe Leu Glu Val Cys Thr
                         115                120                125

Trp Val Asp Gln Ile Ala Ala Leu Asn Asp Ser Lys Thr Arg Lys Thr
                         130                135                140

Thr Ser Glu Thr Val Arg Ala Val Leu Asp Ser Leu Ser Glu Lys Lys
         145                        150                155                160

Lys Ser Ser Pro Ala Ala Asp
                         165

<210> SEQ ID NO 148
<211> LENGTH: 167
```

<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 148

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
            20                  25                  30

Ser Arg Lys Phe Lys His Gly Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Asn Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 149
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 149

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Asn Pro Asn Gln
            20                  25                  30

Ser Tyr Lys Phe Lys His Arg Leu Lys Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Arg Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 150
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 150

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Trp Gln
            20                  25                  30

Ser Cys Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Ser Gly Ser Val Ser Asn Tyr Lys Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 151
<211> LENGTH: 167
<212> TYPE: PRT
<213> ORGANISM: artificial sequence
<220> FEATURE:
<223> OTHER INFORMATION: Second I-CreI variant cleaving mouse Glutamine
      Synthetase gene target

<400> SEQUENCE: 151

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Tyr Lys Phe Lys His Gly Leu Gln Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Gln Leu Ser
65                  70                  75                  80

Glu Ile Lys Pro Leu His Asn Phe Leu Thr Gln Leu Gln Pro Phe Leu
                85                  90                  95

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 152
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 152

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

His Cys Lys Phe Lys His Gln Leu Ala Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Glu Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 153
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 153

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Asp Leu Arg Leu Thr Phe Lys Val Thr Gln
        35                  40                  45
```

```
Lys Thr Gln Arg Arg Trp Phe Leu Asp Lys Leu Val Asp Glu Ile Gly
     50                  55                  60

Val Gly Tyr Val Tyr Asp Ser Gly Ser Val Ser Glu Tyr Val Leu Ser
 65              70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
             100                 105                 110

Leu Pro Ser Ala Lys Glu Ser Pro Asp Lys Phe Leu Glu Val Cys Thr
             115                 120                 125

Trp Val Asp Gln Ile Ala Ala Leu Asn Asp Ser Lys Thr Arg Lys Thr
     130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 154
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 154

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Asn Gln
             20                  25                  30

Ser Asn Lys Phe Lys His Gln Leu Arg Leu Thr Phe Lys Val Thr Gln
         35                  40                  45

Lys Thr Gln Arg Arg Trp Phe Leu Asp Lys Leu Val Asp Glu Ile Gly
     50                  55                  60

Val Gly Tyr Val Tyr Asp Ser Gly Ser Val Ser Glu Tyr Val Leu Ser
 65              70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
             100                 105                 110

Leu Pro Ser Ala Lys Glu Ser Pro Asp Lys Phe Leu Glu Val Cys Thr
             115                 120                 125

Trp Val Asp Gln Ile Ala Ala Leu Asn Asp Ser Lys Thr Arg Lys Thr
     130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 155
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 155
```

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Tyr Lys Phe Lys His Gln Leu Ser Leu Thr Phe Lys Val Thr Gln
            35                  40                  45

Lys Thr Gln Arg Arg Trp Phe Leu Asp Lys Leu Val Asp Glu Ile Gly
        50                  55                  60

Val Gly Tyr Val Glu Asp Ser Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 156
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 156

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Tyr Lys Phe Lys His Gln Leu Ser Leu Thr Phe Lys Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Ser Gly Ser Val Ser Asn Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 157

```
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 157

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Ser Gln
            20                  25                  30

Ser Cys Lys Phe Lys His Gln Leu Ala Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Lys Asp His Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 158
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 158

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Ser Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140
```

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 159
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 159

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Arg Asp Lys Phe Lys His Gln Leu Ser Leu Thr Phe Glu Val Thr Gln
            35                  40                  45

Lys Thr Gln Arg Arg Trp Phe Leu Asp Lys Leu Val Asp Glu Ile Gly
50                  55                  60

Val Gly Tyr Val Cys Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 160
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 160

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser His Lys Phe Lys His Gln Leu Thr Leu Thr Phe Asn Val Thr Gln
            35                  40                  45

Lys Thr Gln Arg Arg Trp Phe Leu Asp Lys Leu Val Asp Glu Ile Gly
50                  55                  60

Val Gly Tyr Val Arg Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 161
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 161

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Ser Cys Lys Phe Lys His His Leu Ser Leu Thr Phe Val Val Thr Gln
            35                  40                  45

Lys Thr Gln Arg Arg Trp Phe Leu Asp Lys Leu Val Asp Glu Ile Gly
    50                  55                  60

Val Gly Tyr Val Glu Asp Arg Gly Ser Val Ser Asn Tyr Arg Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 162
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 162

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asp Gln
                20                  25                  30

Ser Arg Lys Phe Lys His Thr Leu Ser Leu Thr Phe Tyr Val Thr Gln
            35                  40                  45
```

```
Lys Thr Gln Arg Arg Trp Phe Leu Asp Lys Leu Val Asp Glu Ile Gly
            50                  55                  60

Val Gly Tyr Val Arg Asp Ser Gly Ser Val Ser Asp Tyr Val Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
               100                 105                 110

Leu Pro Ser Ala Lys Glu Ser Pro Asp Lys Phe Leu Glu Val Cys Thr
               115                 120                 125

Trp Val Asp Gln Ile Ala Ala Leu Asn Asp Ser Lys Thr Arg Lys Thr
           130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 163
<211> LENGTH: 167
<212> TYPE: PRT
<213> ORGANISM: artificial sequence
<220> FEATURE:
<223> OTHER INFORMATION: First I-CreI variant cleaving Chinese Hamster
      Glutamine Synthetase gene target

<400> SEQUENCE: 163

```
Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Gly Gln
                 20                  25                  30

Ser Tyr Lys Phe Lys His Lys Leu Ser Leu Thr Phe Ala Val Thr Gln
             35                  40                  45

Lys Thr Gln Arg Arg Trp Phe Leu Asp Lys Leu Val Asp Glu Ile Gly
         50                  55                  60

Val Gly Tyr Val Arg Asp Ser Gly Ser Val Ser Glu Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 164
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 164

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Thr Asn Lys Phe Lys His Gln Leu Gln Leu Thr Phe Ile Val Thr Gln
            35                  40                  45

Lys Thr Gln Arg Arg Trp Phe Leu Asp Lys Leu Val Asp Glu Ile Gly
        50                  55                  60

Val Gly Tyr Val Arg Asp Ser Gly Ser Val Ser Asn Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 165
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 165

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Gly Lys Phe Lys His Gln Leu Gly Leu Thr Phe Thr Val Thr Gln
            35                  40                  45

Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Tyr Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

```
<210> SEQ ID NO 166
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 166

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Asp Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 167
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 167

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

His His Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Glu Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
```

```
                130               135                140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 168
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 168

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Ser Gln
                20                  25                  30

Thr Ser Lys Phe Lys His Arg Leu Ser Leu Thr Phe Ala Val Thr Gln
            35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser His Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 169
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 169

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
                20                  25                  30

Gly His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
    50                  55                  60

Val Gly Tyr Val Glu Asp Ser Gly Ser Val Ser Arg Tyr Arg Leu Ser
65                  70                  75                  80

Glu Ile Lys Pro Leu His Asn Phe Leu Thr Gln Leu Gln Pro Phe Leu
```

```
                    85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 170
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 170

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Thr Gln
            20                  25                  30

Ser Gly Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 171
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 171

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Asn Lys Phe Lys His Tyr Leu Arg Leu Thr Phe Gln Val Thr Gln
```

```
                 35                  40                  45
Lys Thr Gln Arg Arg Trp Phe Leu Asp Lys Leu Val Asp Glu Ile Gly
 50                  55                  60

Val Gly Tyr Val Arg Asp Asp Gly Ser Val Ser Asn Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 172
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 172

Met Ala Asn Thr Lys Tyr Asn Lys Glu Phe Leu Leu Tyr Leu Ala Gly
  1                   5                  10                  15

Phe Val Asp Gly Asp Gly Ser Ile Ile Ala Gln Ile Lys Pro Arg Gln
                 20                  25                  30

Ser Tyr Lys Phe Lys His Glu Leu Ser Leu Thr Phe Asp Val Thr Gln
                 35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Ser Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 173
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target
```

<400> SEQUENCE: 173

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Ser Pro Asn Gln
            20                  25                  30

Ser Tyr Lys Phe Lys His Arg Leu Lys Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Tyr Leu Ser
65              70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 174
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 174

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Lys Gln
            20                  25                  30

Ser Ser Lys Phe Lys His Gln Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Ser Tyr Arg Leu Ser
65              70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 175
<211> LENGTH: 167
<212> TYPE: PRT
<213> ORGANISM: artificial sequence
<220> FEATURE:
<223> OTHER INFORMATION: Second I-CreI variant cleaving Chinese Hamster
      Glutamine Synthetase gene target

<400> SEQUENCE: 175

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser Arg Lys Phe Lys His Gln Leu Arg Leu Thr Phe Ala Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Gly Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 176
<211> LENGTH: 24
<212> TYPE: DNA
<213> ORGANISM: artificial sequence
<220> FEATURE:
<223> OTHER INFORMATION: 10GCC_P target

<400> SEQUENCE: 176
tcgccacgtc gtacgacgtg gcga                                          24

<210> SEQ ID NO 177
<211> LENGTH: 24
<212> TYPE: DNA
<213> ORGANISM: artificial sequence
<220> FEATURE:
<223> OTHER INFORMATION: 10GGA_P target

<400> SEQUENCE: 177
tcggaacgtc gtacgacgtt ccga                                          24

<210> SEQ ID NO 178
<211> LENGTH: 24
<212> TYPE: DNA
<213> ORGANISM: artificial sequence
<220> FEATURE:
<223> OTHER INFORMATION: 5AGG_P target

<400> SEQUENCE: 178
tcaaaacagg gtaccctgtt ttga                                          24

<210> SEQ ID NO 179
<211> LENGTH: 24
<212> TYPE: DNA
<213> ORGANISM: artificial sequence
<220> FEATURE:
<223> OTHER INFORMATION: 5TTC_P target

<400> SEQUENCE: 179
tcaaaacttc gtacgaagtt ttga                                          24

<210> SEQ ID NO 180
<211> LENGTH: 22
<212> TYPE: DNA
<213> ORGANISM: artificial sequence
<220> FEATURE:
<223> OTHER INFORMATION: GSCHO1.2 target

<400> SEQUENCE: 180
tgccccaggg tacgaaagtc ca                                            22

<210> SEQ ID NO 181
<211> LENGTH: 22
<212> TYPE: DNA
<213> ORGANISM: artificial sequence
<220> FEATURE:
<223> OTHER INFORMATION: GSCHO1.3 target

<400> SEQUENCE: 181
tgccccaggg taccctgggg ca                                            22

<210> SEQ ID NO 182
<211> LENGTH: 22
<212> TYPE: DNA
<213> ORGANISM: artificial sequence
<220> FEATURE:
<223> OTHER INFORMATION: GSCHO1.4 target

<400> SEQUENCE: 182
tggactttcg tacgaaagtc ca                                            22

<210> SEQ ID NO 183
<211> LENGTH: 51
<212> TYPE: DNA
<213> ORGANISM: artificial sequence
<220> FEATURE:
<223> OTHER INFORMATION: GSCHO1.3 oligonucleotide

<400> SEQUENCE: 183
tggcatacaa gtttctgccc cagggtaccc tggggcagca atcgtctgtc a             51

<210> SEQ ID NO 184
<211> LENGTH: 167
<212> TYPE: PRT
<213> ORGANISM: artificial sequence
<220> FEATURE:
<223> OTHER INFORMATION: GSCHO1.3 variant of Table VI

<400> SEQUENCE: 184

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Thr Val Thr Gln
        35                  40                  45

```
Lys Thr Gln Arg Arg Trp Phe Leu Asp Lys Leu Val Asp Glu Ile Gly
         50                  55                  60

Val Gly Tyr Val Tyr Asp Ser Gly Ser Val Ser Asn Tyr Ile Leu Ser
 65              70                  75                      80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
             100                 105                 110

Leu Pro Ser Ala Lys Glu Ser Pro Asp Lys Phe Leu Glu Val Cys Thr
             115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 185
<211> LENGTH: 51
<212> TYPE: DNA
<213> ORGANISM: artificial sequence
<220> FEATURE:
<223> OTHER INFORMATION: GSCHO1.4 oligonucleotide

<400> SEQUENCE: 185
tggcatacaa gtttttggac tttcgtacga aagtccaaca atcgtctgtc a        51

<210> SEQ ID NO 186
<211> LENGTH: 26
<212> TYPE: DNA
<213> ORGANISM: artificial sequence
<220> FEATURE:
<223> OTHER INFORMATION: Gal10F primer

<400> SEQUENCE: 186
gcaactttag tgctgacaca tacagg                                     26

<210> SEQ ID NO 187
<211> LENGTH: 24
<212> TYPE: DNA
<213> ORGANISM: artificial sequence
<220> FEATURE:
<223> OTHER INFORMATION: Gal10R primer

<400> SEQUENCE: 187
acaaccttga ttggagactt gacc                                       24

<210> SEQ ID NO 188
<211> LENGTH: 15
<212> TYPE: DNA
<213> ORGANISM: artificial sequence
<220> FEATURE:
<223> OTHER INFORMATION: assF primer
<220> FEATURE:
<221> NAME/KEY: misc_feature
<222> LOCATION: (4)..(6)
<223> OTHER INFORMATION: n is a, c, g, or t

<400> SEQUENCE: 188
ctannnttga cctttt                                                15

<210> SEQ ID NO 189

```
<211> LENGTH: 15
<212> TYPE: DNA
<213> ORGANISM: artificial sequence
<220> FEATURE:
<223> OTHER INFORMATION: assR primer
<220> FEATURE:
<221> NAME/KEY: misc_feature
<222> LOCATION: (10)..(12)
<223> OTHER INFORMATION: n is a, c, g, or t

<400> SEQUENCE: 189
aaaggtcaan nntag                                                     15

<210> SEQ ID NO 190
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 190

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 191
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 191

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ser His Lys Phe Lys His Asn Leu Ser Leu Thr Phe Lys Val Thr Lys
        35                  40                  45

Lys Thr Gln Arg Arg Trp Phe Leu Asp Lys Leu Val Asp Glu Ile Gly
    50                  55                  60
```

```
Val Gly Tyr Val Asn Asp Ser Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 192
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 192

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Lys Val Thr Gln
        35                  40                  45

Lys Thr Gln Arg Arg Trp Phe Leu Asp Lys Leu Ala Asp Glu Ile Gly
    50                  55                  60

Val Gly Tyr Val Asn Asp Ala Gly Ser Val Ser Asn Tyr Ile Leu Ser
 65                 70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 193
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 193

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30
```

```
Ser Thr Lys Phe Lys His Arg Leu Ser Leu Thr Phe Lys Val Thr Gln
        35                  40                  45

Lys Thr Gln Arg Arg Trp Phe Leu Asp Lys Leu Val Asp Glu Ile Gly
 50                  55                  60

Val Gly Tyr Val Asn Asp Ser Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 194
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 194

```
Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Arg Gln
                 20                  25                  30

Gly Tyr Lys Phe Lys His Gln Leu Ser Leu Thr Phe Lys Met Thr Gln
                 35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Asn Tyr Val Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 195
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 195

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 196
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 196

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Asn Gln
            20                  25                  30

Ala His Lys Phe Lys His Gln Leu Ser Leu Thr Phe Lys Val Thr Gln
        35                  40                  45

Lys Thr Gln Arg Arg Trp Phe Leu Asp Lys Leu Val Asp Glu Ile Gly
    50                  55                  60

Val Gly Tyr Val Pro Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

```
<210> SEQ ID NO 197
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 197

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro His Gln
                20                  25                  30

Arg His Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 198
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 198

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Asp Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Thr Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
    130                 135                 140
```

```
Thr Ser Glu Thr Val Arg Ala Val Leu Asp Ser Leu Ser Glu Lys Lys
145                 150                 155                 160

Lys Ser Ser Pro Ala Ala Asp
            165
```

<210> SEQ ID NO 199
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 199

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Asp Tyr Lys Phe Lys His Gln Leu Ser Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Arg Asp Ser Gly Ser Val Ser Arg Tyr Ile Leu Ser
65                  70                  75                  80

Lys Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165
```

<210> SEQ ID NO 200
<211> LENGTH: 167
<212> TYPE: PRT
<213> ORGANISM: artificial sequence
<220> FEATURE:
<223> OTHER INFORMATION: GSCHO1.4 variant of Table VIII

<400> SEQUENCE: 200

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110
```

```
Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 201
<211> LENGTH: 51
<212> TYPE: DNA
<213> ORGANISM: artificial sequence
<220> FEATURE:
<223> OTHER INFORMATION: GSCHO1.2 oligonucleotide

<400> SEQUENCE: 201
tggcatacaa gtttctgccc cagggtacga aagtccaaca atcgtctgtc a        51

<210> SEQ ID NO 202
<211> LENGTH: 51
<212> TYPE: DNA
<213> ORGANISM: artificial sequence
<220> FEATURE:
<223> OTHER INFORMATION: GSCHO1 oligonucleotide

<400> SEQUENCE: 202
tggcatacaa gtttctgccc cagggtgaga aagtccaaca atcgtctgtc a        51

<210> SEQ ID NO 203
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 203

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 204
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 204

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val Thr Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 205
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 205

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Val Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
```

```
              130                 135                 140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 206
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 206

Met Ala Asn Thr Lys Tyr Asn Lys Glu Phe Leu Leu Tyr Leu Ala Gly
1               5                  10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Lys Val Thr Gln
            35                  40                  45

Lys Thr Gln Arg Arg Trp Phe Leu Asp Lys Leu Val Asp Glu Ile Gly
50                  55                  60

Val Gly Tyr Val Ala Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 207
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 207

Met Ala Asn Thr Lys Tyr Asn Lys Glu Phe Leu Leu Tyr Leu Ala Gly
1               5                  10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Asn Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Arg Tyr Ile Leu Ser
65                  70                  75                  80

Glu Ile Lys Pro Leu His Asn Phe Leu Thr Gln Leu Gln Pro Phe Leu
                85                  90                  95
```

```
Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 208
<211> LENGTH: 167
<212> TYPE: PRT
<213> ORGANISM: artificial sequence
<220> FEATURE:
<223> OTHER INFORMATION: GSCHO1.4 variant of Table X

<400> SEQUENCE: 208

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Lys Gln
            20                  25                  30

Ser Ala Lys Phe Lys His Gln Leu Ser Leu Thr Phe Asn Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Arg Tyr Tyr Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 209
<211> LENGTH: 59
<212> TYPE: DNA
<213> ORGANISM: artificial sequence
<220> FEATURE:
<223> OTHER INFORMATION: preATGCreFor primer

<400> SEQUENCE: 209
gcataaatta ctatacttct atagacacgc aaacacaaat acacagcggc cttgccacc      59

<210> SEQ ID NO 210
<211> LENGTH: 48
<212> TYPE: DNA
<213> ORGANISM: artificial sequence
<220> FEATURE:
<223> OTHER INFORMATION: ICreIpostRev primer

<400> SEQUENCE: 210
```
ggctcgagga gctcgtctag aggatcgctc gagttatcag tcggccgc    48

<210> SEQ ID NO 211
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 211

Met Ala Asn Thr Lys Tyr Asn Glu Glu Phe Leu Leu Tyr Leu Ala Gly
1               5                   10                  15

Phe Val Asp Ala Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Ala Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 212
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 212

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly His Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

```
Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 213
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 213

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Leu Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 214
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 214

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Leu Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
```

```
                85                  90                  95
Lys Leu Lys Gln Lys Gln Ala Asn Leu Val Leu Lys Ile Ile Glu Gln
            100                 105                 110
Leu Pro Ser Ala Lys Glu Ser Pro Asp Lys Phe Leu Glu Val Cys Thr
            115                 120                 125
Trp Val Asp Gln Ile Ala Ala Leu Asn Asp Ser Lys Thr Arg Lys Thr
130                 135                 140
Thr Ser Glu Thr Val Arg Ala Val Leu Asp Ser Leu Ser Glu Lys Lys
145                 150                 155                 160
Lys Ser Ser Pro Ala Ala Asp
            165

<210> SEQ ID NO 215
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 215

Met Ala Asn Thr Lys Tyr Asn Lys Glu Phe Leu Leu Tyr Leu Ala Gly
1               5                   10                  15
Phe Val Asp Ser Asp Gly Ser Ile Ile Ala Gln Ile Lys Pro Arg Gln
            20                  25                  30
Ser Arg Lys Phe Lys His Glu Leu Ser Leu Thr Phe Asp Val Thr Gln
        35                  40                  45
Lys Thr Gln Arg Arg Trp Phe Leu Asp Glu Leu Val Asp Glu Ile Gly
    50                  55                  60
Val Gly Tyr Val Tyr Asp Ser Gly Ser Val Ser Tyr Tyr Gln Leu Ser
65                  70                  75                  80
Glu Ile Lys Pro Leu His Asn Phe Leu Thr Gln Leu Gln Pro Phe Leu
                85                  90                  95
Lys Leu Lys Gln Lys Gln Ala Asn Leu Val Leu Lys Ile Ile Glu Gln
            100                 105                 110
Leu Pro Ser Ala Lys Glu Thr Pro Asp Lys Phe Leu Glu Val Cys Thr
            115                 120                 125
Trp Val Asp Gln Val Ala Ala Leu Asn Asp Ser Lys Thr Arg Lys Thr
130                 135                 140
Thr Ser Glu Thr Val Arg Ala Val Leu Asp Ser Leu Ser Glu Lys Lys
145                 150                 155                 160
Lys Ser Ser Pro Ala Ala Asp
            165

<210> SEQ ID NO 216
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 216

Met Ala Asn Thr Lys Tyr Asn Lys Glu Phe Leu Leu Tyr Leu Ala Gly
1               5                   10                  15
Phe Val Asp Gly Asp Gly Ser Ile Val Ala Gln Ile Lys Pro Arg Gln
            20                  25                  30
Ser Arg Lys Phe Lys His Glu Leu Ser Leu Thr Phe Thr Val Thr Gln
        35                  40                  45
```

```
Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Asn Tyr Thr Leu Ser
 65                  70                  75                  80

Lys Ile Lys Pro Leu His Asn Phe Leu Thr Gln Leu Gln Pro Phe Leu
                 85                  90                  95

Lys Leu Lys Gln Lys Gln Ala Asn Leu Val Leu Arg Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 217
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 217

```
Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Arg Gln
                 20                  25                  30

Ser Arg Lys Phe Lys His Glu Leu Ser Leu Thr Phe Thr Val Thr Gln
            35                  40                  45

Lys Thr Arg Arg Arg Trp Phe Leu Asp Lys Leu Val Asp Glu Ile Gly
        50                  55                  60

Val Gly Tyr Val Tyr Asp Ser Gly Ser Val Ser Asn Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 218
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 218

```
Met Ala Asn Thr Lys Tyr Asn Lys Glu Phe Leu Leu Tyr Leu Ala Gly
 1               5                  10                  15
```

```
Phe Val Asp Gly Asp Gly Ser Ile Ile Ala Gln Ile Lys Pro Arg Gln
            20                  25                  30

Ser Arg Lys Phe Lys His Glu Val Ser Leu Thr Phe Asp Val Thr Gln
            35                  40                  45

Lys Thr Gln Arg Arg Trp Phe Leu Asp Lys Leu Val Asp Glu Ile Gly
            50                  55                  60

Val Gly Tyr Val Tyr Asp Ser Gly Ser Val Ser Tyr Tyr Gln Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 219
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 219

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
            35                  40                  45

Lys Thr Gln Arg Arg Trp Phe Leu Asp Lys Leu Val Asp Glu Ile Gly
            50                  55                  60

Val Gly Tyr Val Tyr Asp Ser Gly Ser Val Ser Tyr Tyr Gln Leu Ser
 65                  70                  75                  80

Glu Ile Lys Pro Leu His Asn Phe Leu Thr Gln Leu Gln Pro Phe Leu
                85                  90                  95

Arg Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Ala Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 220
<211> LENGTH: 167
<212> TYPE: PRT
<213> ORGANISM: artificial sequence
```

<220> FEATURE:
<223> OTHER INFORMATION: Optimized GSCHO1.3 variant of Table XII

<400> SEQUENCE: 220

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Leu Thr Gln
        35                  40                  45

Lys Thr Arg Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 221
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 221

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Arg Ile Ile Glu Gln
            100                 105                 110

Leu Pro Ser Ala Lys Glu Ser Pro Asp Lys Phe Leu Glu Val Cys Thr
        115                 120                 125

Trp Ala Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp

```
                165

<210> SEQ ID NO 222
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 222

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Arg Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 223
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 223

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125
```

```
Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Pro Ser Pro Ala Ala Asp
                165

<210> SEQ ID NO 224
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 224

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Arg Lys Phe Lys His Glu Leu Ser Leu Thr Phe Asp Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Glu Lys Phe Leu Glu Val Cys Thr
        115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 225
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 225

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Arg Lys Phe Lys His Glu Leu Ser Leu Thr Phe Asp Val Thr Gln
            35                  40                  45

Lys Thr Gln Arg Arg Trp Phe Leu Asp Lys Leu Val Asp Glu Ile Gly
50                  55                  60

Val Gly Tyr Val Tyr Asp Ser Gly Ser Val Ser Tyr Tyr Gln Leu Ser
65                  70                  75                  80

Glu Ile Lys Pro Leu His Asn Leu Leu Thr Gln Leu Gln Pro Phe Leu
                85                  90                  95
```

```
Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Arg Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 226
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 226

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Ala Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 227
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 227

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Asp Val Thr Gln
        35                  40                  45

Lys Thr Gln Arg Arg Trp Phe Leu Asp Lys Leu Val Asp Glu Ile Gly
```

-continued

```
                 50                  55                  60
Ala Gly Tyr Val Tyr Asp Ser Gly Ser Val Ser Tyr Gln Leu Ser
 65                  70                  75                  80

Glu Ile Lys Pro Leu His Asn Ile Leu Thr Gln Leu Gln Pro Phe Leu
                 85                  90                  95

Lys Leu Lys Gln Lys Gln Ala Asn Leu Ala Leu Lys Ile Ile Glu Gln
                100                 105                 110

Leu Pro Ser Ala Lys Val Ser Pro Asp Lys Phe Leu Glu Val Cys Thr
                115                 120                 125

Trp Val Asp Gln Ile Ala Ala Leu Asn Asn Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 228
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 228

Met Ala Asn Thr Lys Tyr Asn Lys Glu Phe Leu Leu Tyr Leu Ala Gly
 1               5                  10                  15

Phe Val Asp Gly Asp Gly Ser Ile Val Ala Gln Ile Lys Pro Arg Gln
                20                  25                  30

Ser Tyr Lys Phe Lys His Glu Leu Ser Leu Thr Phe Asp Val Thr Gln
                35                  40                  45

Lys Thr Gln Arg Arg Trp Phe Leu Asp Lys Leu Val Asp Glu Ile Gly
 50                  55                  60

Val Gly Tyr Val Tyr Asp Ser Gly Ser Val Ser Tyr Gln Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Val Cys Thr
                115                 120                 125

Trp Val Asp Gln Ile Ala Ala Leu Asn Asp Ser Lys Thr Arg Lys Thr
                130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 229
<211> LENGTH: 167
<212> TYPE: PRT
<213> ORGANISM: artificial sequence
<220> FEATURE:
<223> OTHER INFORMATION: Optimized GSCHO1.3 variant of Table XII

<400> SEQUENCE: 229

Met Ala Asn Thr Lys Tyr Asn Lys Glu Phe Leu Leu Tyr Leu Ala Gly
 1               5                  10                  15
```

Phe Val Asp Gly Asp Gly Ser Ile Ile Ala Gln Ile Lys Pro Arg Gln
            20                  25                  30

Ser Arg Lys Phe Lys His Glu Leu Ser Leu Thr Phe Thr Val Thr Gln
        35                  40                  45

Lys Thr Gln Arg Arg Trp Phe Leu Asp Lys Leu Val Asp Glu Ile Gly
    50                  55                  60

Val Gly Tyr Val Tyr Asp Ser Gly Ser Val Ser Asn Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 230
<211> LENGTH: 33
<212> TYPE: DNA
<213> ORGANISM: artificial sequence
<220> FEATURE:
<223> OTHER INFORMATION: G19SF primer

<400> SEQUENCE: 230
gccggctttg tggactctga cggtagcatc atc                              33

<210> SEQ ID NO 231
<211> LENGTH: 33
<212> TYPE: DNA
<213> ORGANISM: artificial sequence
<220> FEATURE:
<223> OTHER INFORMATION: G19SR primer

<400> SEQUENCE: 231
gatgatgcta ccgtcagagt ccacaaagcc ggc                              33

<210> SEQ ID NO 232
<211> LENGTH: 33
<212> TYPE: DNA
<213> ORGANISM: artificial sequence
<220> FEATURE:
<223> OTHER INFORMATION: F54LF primer

<400> SEQUENCE: 232
acccagcgcc gttggctgct ggacaaacta gtg                              33

<210> SEQ ID NO 233
<211> LENGTH: 33
<212> TYPE: DNA
<213> ORGANISM: artificial sequence
<220> FEATURE:
<223> OTHER INFORMATION: F54LR primer

<400> SEQUENCE: 233
cactagtttg tccagcagcc aacggcgctg ggt                              33

<210> SEQ ID NO 234
<211> LENGTH: 33
<212> TYPE: DNA
<213> ORGANISM: artificial sequence
<220> FEATURE:
<223> OTHER INFORMATION: E80KF primer

<400> SEQUENCE: 234
ttaagcaaaa tcaagccgct gcacaacttc ctg         33

<210> SEQ ID NO 235
<211> LENGTH: 33
<212> TYPE: DNA
<213> ORGANISM: artificial sequence
<220> FEATURE:
<223> OTHER INFORMATION: E80KR primer

<400> SEQUENCE: 235
caggaagttg tgcagcggct tgattttgct taa         33

<210> SEQ ID NO 236
<211> LENGTH: 33
<212> TYPE: DNA
<213> ORGANISM: artificial sequence
<220> FEATURE:
<223> OTHER INFORMATION: F87LF primer

<400> SEQUENCE: 236
aagccgctgc acaacctgct gactcaactg cag         33

<210> SEQ ID NO 237
<211> LENGTH: 33
<212> TYPE: DNA
<213> ORGANISM: artificial sequence
<220> FEATURE:
<223> OTHER INFORMATION: F87LR primer

<400> SEQUENCE: 237
ctgcagttga gtcagcaggt tgtgcagcgg ctt         33

<210> SEQ ID NO 238
<211> LENGTH: 33
<212> TYPE: DNA
<213> ORGANISM: artificial sequence
<220> FEATURE:
<223> OTHER INFORMATION: V105AF primer

<400> SEQUENCE: 238
aaacaggcaa acctggctct gaaaattatc gaa         33

<210> SEQ ID NO 239
<211> LENGTH: 33
<212> TYPE: DNA
<213> ORGANISM: artificial sequence
<220> FEATURE:
<223> OTHER INFORMATION: V105AR primer

<400> SEQUENCE: 239
ttcgataatt ttcagagcca ggtttgcctg ttt         33

<210> SEQ ID NO 240
<211> LENGTH: 33
<212> TYPE: DNA
<213> ORGANISM: artificial sequence
<220> FEATURE:
<223> OTHER INFORMATION: I132VF primer

<400> SEQUENCE: 240
acctgggtgg atcaggttgc agctctgaac gat    33

<210> SEQ ID NO 241
<211> LENGTH: 33
<212> TYPE: DNA
<213> ORGANISM: artificial sequence
<220> FEATURE:
<223> OTHER INFORMATION: I132VR primer

<400> SEQUENCE: 241
atcgttcaga gctgcaacct gatccaccca ggt    33

<210> SEQ ID NO 242
<211> LENGTH: 167
<212> TYPE: PRT
<213> ORGANISM: artificial sequence
<220> FEATURE:
<223> OTHER INFORMATION: optimized GSCHO1.3 variant Table XII

<400> SEQUENCE: 242

Met Ala Asn Thr Lys Tyr Asn Lys Glu Phe Leu Leu Tyr Leu Ala Gly
1               5                   10                  15

Phe Val Asp Ser Asp Gly Ser Ile Ile Ala Gln Ile Lys Pro Arg Gln
                20                  25                  30

Ser Arg Lys Phe Lys His Glu Leu Ser Leu Thr Phe Asp Val Thr Gln
            35                  40                  45

Lys Thr Gln Arg Arg Trp Phe Leu Asp Lys Leu Val Asp Glu Ile Gly
        50                  55                  60

Val Gly Tyr Val Tyr Asp Ser Gly Ser Val Ser Tyr Tyr Gln Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 243
<211> LENGTH: 167
<212> TYPE: PRT
<213> ORGANISM: artificial sequence
<220> FEATURE:
<223> OTHER INFORMATION: optimized GSCHO1.3 variant Table XII

<400> SEQUENCE: 243

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser Arg Lys Phe Lys His Glu Leu Ser Leu Thr Phe Asp Val Thr Gln
            35                  40                  45

Lys Thr Gln Arg Arg Trp Phe Leu Asp Lys Leu Val Asp Glu Ile Gly

```
              50                  55                  60
Val Gly Tyr Val Tyr Asp Ser Gly Ser Val Ser Tyr Tyr Gln Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 244
<211> LENGTH: 167
<212> TYPE: PRT
<213> ORGANISM: artificial sequence
<220> FEATURE:
<223> OTHER INFORMATION: optimized GSCHO1.3 variant Table XII

<400> SEQUENCE: 244

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Arg Gln
                 20                  25                  30

Ser Arg Lys Phe Lys His Glu Leu Ser Leu Thr Phe Asp Val Thr Gln
             35                  40                  45

Lys Thr Gln Arg Arg Trp Phe Leu Asp Lys Leu Val Asp Glu Ile Gly
         50                  55                  60

Val Gly Tyr Val Tyr Asp Ser Gly Ser Val Ser Tyr Tyr Gln Leu Ser
 65                  70                  75                  80

Lys Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 245
<211> LENGTH: 167
<212> TYPE: PRT
<213> ORGANISM: artificial seqeunce
<220> FEATURE:
<223> OTHER INFORMATION: optimized GSCHO1.4 variant Table XIII

<400> SEQUENCE: 245

Met Ala Asn Ala Lys Tyr Asn Lys Glu Phe Leu Leu Tyr Leu Ala Gly
  1               5                  10                  15
```

Phe Val Asp Gly Asp Gly Ser Ile Ile Ala Gln Ile Lys Pro Arg Gln
        20                  25                  30

Ser Arg Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 246
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 246

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Leu Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 247
<211> LENGTH: 167
<212> TYPE: PRT
<213> ORGANISM: artificial sequence
<220> FEATURE:

<223> OTHER INFORMATION: optimized GSCHO1.4 variant Table XIII

<400> SEQUENCE: 247

Met Ala Asn Thr Lys Tyr Asn Lys Glu Phe Leu Leu Tyr Leu Ala Gly
1               5                   10                  15

Phe Val Asp Ser Asp Gly Ser Ile Ile Ala Gln Ile Lys Pro Arg Gln
            20                  25                  30

Asp Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Thr Ser Pro Ala Ala Asp
                165

<210> SEQ ID NO 248
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 248

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Gly Tyr Lys Phe Lys His Gln Leu Ser Leu Thr Phe Arg Val Thr Gln
        35                  40                  45

Lys Thr Gln Arg Arg Trp Phe Leu Asp Lys Leu Val Asp Glu Ile Gly
    50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Val Ala Ala Leu Asn Asp Ser Lys Thr Arg Lys Thr
    130                 135                 140

Thr Ser Glu Thr Val Arg Ala Val Leu Asp Gly Leu Ser Glu Lys Lys
145                 150                 155                 160

Lys Ser Ser Pro Ala Ala Asp
                165

<210> SEQ ID NO 249
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 249

```
Met Ala Ser Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165
```

<210> SEQ ID NO 250
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 250

```
Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Arg Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
```

```
                130             135             140
Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 251
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 251

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 252
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 252

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95
```

```
Lys Leu Lys Gln Lys Gln Ala Asn Leu Val Leu Lys Ile Ile Glu Gln
                100                 105                 110

Leu Pro Ser Ala Lys Glu Ser Pro Asp Lys Phe Leu Glu Ile Cys Thr
            115                 120                 125

Trp Val Asp Gln Val Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Arg Ser Ser Pro Ala Ala Asp
                165

<210> SEQ ID NO 253
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 253

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
                100                 105                 110

Leu Pro Phe Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
        130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 254
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 254

Met Ala Asn Thr Lys Tyr Asn Lys Glu Phe Leu Leu His Leu Ala Gly
1               5                   10                  15

Phe Val Asp Gly Asp Gly Ser Ile Ile Ala Gln Ile Lys Pro Arg Gln
            20                  25                  30

Ala His Lys Phe Lys His Gln Leu Ser Leu Thr Phe Gln Met Thr Gln
        35                  40                  45

Lys Thr Gln Arg Arg Trp Phe Leu Asp Lys Leu Val Asp Glu Ile Gly
    50                  55                  60
```

```
Val Gly Tyr Val Ser Asp Arg Gly Ser Val Ser Asp Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 255
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 255

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Arg Gln
                 20                  25                  30

Ser His Lys Phe Lys His Gln Leu Ser Leu Thr Phe Gln Val Thr Gln
             35                  40                  45

Lys Thr Gln Arg Arg Trp Phe Leu Asp Lys Leu Val Tyr Glu Ile Gly
 50                  55                  60

Val Gly Tyr Val Ala Asp Arg Gly Ser Val Ser Asp Tyr Arg Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 256
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 256

Met Ala Asn Thr Lys Tyr Asn Lys Glu Phe Leu Leu Tyr Leu Ala Gly
  1               5                  10                  15

Phe Val Asp Gly Asp Gly Ser Ile Ile Ala Gln Ile Lys Pro Arg Gln
```

```
                    20                  25                  30

Ser His Lys Phe Lys His Gln Leu Ser Leu Thr Phe Gln Val Thr Gln
            35                  40                  45

Lys Thr Arg Arg Arg Trp Phe Leu Asp Lys Leu Val Asp Glu Ile Gly
        50                  55                  60

Val Gly Tyr Val Ala Asp Arg Gly Ser Val Ser Asp Tyr Arg Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 257
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 257

Met Ala Asn Thr Lys Tyr Asn Lys Glu Phe Leu Leu Tyr Leu Ala Gly
 1               5                  10                  15

Phe Val Asp Gly Asp Gly Ser Ile Ile Ala Gln Ile Lys Pro Arg Gln
                20                  25                  30

Ser His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Ala Asp Arg Gly Ser Val Ser Asp Tyr Arg Leu Ser
 65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Val Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asn Ser Leu Ser Glu Lys Lys
145                 150                 155                 160

Lys Ser Ser Pro Ala Ala Asp
                165

<210> SEQ ID NO 258
<211> LENGTH: 167
<212> TYPE: PRT
<213> ORGANISM: artificial sequence
<220> FEATURE:
<223> OTHER INFORMATION: optimized GSCHO1.4 variant Table XIII
```

<400> SEQUENCE: 258

Met Ala Asn Thr Lys Tyr Lys Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Pro Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 259
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 259

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Leu Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

```
<210> SEQ ID NO 260
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 260

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Gly His Lys Phe Lys His Gln Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Ser Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Tyr Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 261
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 261

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Ser His Lys Phe Lys His His Leu Ser Leu Thr Phe Gln Val Thr Gln
            35                  40                  45

Lys Thr Gln Arg Arg Trp Phe Leu Asp Lys Leu Val Asp Glu Ile Gly
        50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140
```

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 262
<211> LENGTH: 167
<212> TYPE: PRT
<213> ORGANISM: artificial sequence
<220> FEATURE:
<223> OTHER INFORMATION: optimized GSCHO1.4 variant Table XIII

<400> SEQUENCE: 262

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Thr Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
    130                 135                 140

Thr Ser Glu Thr Val Arg Ala Val Leu Asp Ser Leu Ser Glu Lys Lys
145                 150                 155                 160

Lys Ser Ser Pro Ala Ala Asp
            165

<210> SEQ ID NO 263
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 263

Met Ala Asn Thr Lys Tyr Asn Lys Glu Phe Leu Leu Tyr Leu Ala Gly
1               5                   10                  15

Phe Val Asp Ser Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
    50                  55                  60

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln

```
              100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 264
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 264

Met Ala Asn Thr Lys Tyr Asn Lys Glu Phe Leu Leu Tyr Leu Ala Gly
1               5                  10                  15

Phe Val Asp Ser Asp Gly Ser Ile Ile Ala Gln Ile Lys Pro Arg Gln
            20                  25                  30

Gly Tyr Lys Phe Lys His Gln Leu Ser Leu Thr Phe Lys Met Thr Gln
        35                  40                  45

Lys Thr Gln Arg Arg Trp Phe Leu Asp Lys Leu Val Asp Glu Ile Gly
50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 265
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 265

Met Ala Asn Thr Lys Tyr Asn Lys Glu Phe Leu Leu Tyr Leu Ala Gly
1               5                  10                  15

Phe Val Asp Gly Asp Gly Ser Ile Ile Ala Gln Ile Lys Pro Arg Gln
            20                  25                  30

Ser His Lys Phe Lys His Gln Leu Ser Leu Thr Phe Gln Val Thr Gln
        35                  40                  45

Lys Thr Gln Arg Arg Trp Phe Leu Asp Lys Leu Val Asp Glu Ile Gly
50                  55                  60
```

Val Gly Tyr Val Ala Asp Arg Gly Ser Val Ser Asp Tyr Arg Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 266
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 266

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Arg Val Thr Gln
            35                  40                  45

Lys Thr Gln Arg Arg Trp Phe Leu Asp Lys Leu Val Asp Glu Ile Gly
        50                  55                  60

Val Gly Tyr Val His Asp Arg Gly Ser Val Ser Asp Tyr Ile Leu Ser
65                  70                  75                  80

Glu Ile Lys Pro Leu His Asn Phe Leu Thr Gln Leu Gln Pro Phe Leu
                85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
            115                 120                 125

Trp Val Asp Gln Val Ala Ala Leu Asn Asp Ser Lys Thr Arg Lys Thr
            130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 267
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 267

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
                20                  25                  30

Gly Tyr Lys Phe Lys His Gln Leu Ser Leu Thr Phe Arg Val Thr Gln
            35                  40                  45

Lys Thr Gln Arg Arg Trp Leu Leu Asp Lys Leu Val Asp Glu Ile Gly
     50                  55                  60

Val Gly Tyr Val His Asp Arg Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 268
<211> LENGTH: 167
<212> TYPE: PRT
<213> ORGANISM: artificial sequence
<220> FEATURE:
<223> OTHER INFORMATION: optimized GSCHO1.4 variant Table XIV

<400> SEQUENCE: 268

Met Ala Asn Thr Lys Tyr Asn Lys Glu Phe Leu Leu Tyr Leu Ala Gly
1               5                   10                  15

Phe Val Asp Gly Asp Gly Ser Ile Ile Ala Gln Ile Lys Pro Arg Gln
            20                  25                  30

Ser Thr Lys Phe Lys His Arg Leu Ser Leu Thr Phe Lys Val Thr Gln
        35                  40                  45

Lys Thr Gln Arg Arg Trp Leu Leu Asp Lys Leu Val Asp Glu Ile Gly
     50                  55                  60

Val Gly Tyr Val His Asp Arg Gly Ser Val Ser Asp Tyr Ile Leu Ser
 65                  70                  75                  80

Glu Ile Lys Pro Leu His Asn Phe Leu Thr Gln Leu Gln Pro Phe Leu
                 85                  90                  95

Lys Leu Lys Gln Lys Gln Ala Asn Leu Val Leu Lys Ile Ile Glu Gln
            100                 105                 110

Leu Pro Ser Ala Lys Glu Ser Pro Asp Lys Phe Leu Glu Val Cys Thr
        115                 120                 125

Trp Val Asp Gln Ile Ala Ala Leu Asn Asp Ser Lys Thr Arg Lys Thr
130                 135                 140

Thr Ser Glu Thr Val Arg Ala Val Leu Asp Ser Leu Ser Glu Lys Lys
145                 150                 155                 160

Lys Ser Ser Pro Ala Ala Asp
                165

<210> SEQ ID NO 269
<211> LENGTH: 77
<212> TYPE: DNA
<213> ORGANISM: artificial sequence
<220> FEATURE:
<223> OTHER INFORMATION: attB1-ICreIFor primer

```
<400> SEQUENCE: 269 gggggacaagt tgtacaaaa aagcaggctt cgaaggagat agaaccatgg ccaataccaa    60
atataacaaa gagttcc                                                  77

<210> SEQ ID NO 270
<211> LENGTH: 64
<212> TYPE: DNA
<213> ORGANISM: artificial sequence
<220> FEATURE:
<223> OTHER INFORMATION: attB2-ICreIRev primer

<400> SEQUENCE: 270
ggggaccact ttgtacaaga aagctgggtt tagtcggccg ccggggagga tttcttcttc    60
tcgc                                                                64

<210> SEQ ID NO 271
<211> LENGTH: 167
<212> TYPE: PRT
<213> ORGANISM: artificial sequence
<220> FEATURE:
<223> OTHER INFORMATION: optimized GSCHO1.3 variant of Table XV

<400> SEQUENCE: 271
```

| | | | | | | | | | | | | | | | |
|---|---|---|---|---|---|---|---|---|---|---|---|---|---|---|---|
| Met | Ala | Asn | Thr | Lys | Tyr | Asn | Lys | Glu | Phe | Leu | Leu | Tyr | Leu | Ala | Gly |
| 1 | | | | 5 | | | | | 10 | | | | | 15 | |
| Phe | Val | Asp | Ala | Asp | Gly | Ser | Ile | Ile | Ala | Gln | Ile | Lys | Pro | Arg | Gln |
| | | | 20 | | | | | 25 | | | | | 30 | | |
| Ser | Arg | Lys | Phe | Lys | His | Glu | Leu | Ser | Leu | Thr | Phe | Asp | Val | Thr | Gln |
| | | 35 | | | | | 40 | | | | | 45 | | | |
| Lys | Thr | Gln | Arg | Arg | Trp | Phe | Leu | Asp | Lys | Leu | Val | Asp | Glu | Ile | Gly |
| 50 | | | | | 55 | | | | | 60 | | | | | |
| Val | Gly | Tyr | Val | Tyr | Asp | Ser | Gly | Ser | Val | Ser | Tyr | Tyr | Gln | Leu | Ser |
| 65 | | | | 70 | | | | | 75 | | | | | 80 | |
| Glu | Ile | Lys | Pro | Leu | His | Asn | Phe | Leu | Thr | Gln | Leu | Gln | Pro | Phe | Leu |
| | | | | 85 | | | | | 90 | | | | | 95 | |
| Lys | Leu | Lys | Gln | Lys | Gln | Ala | Asn | Leu | Val | Leu | Lys | Ile | Ile | Glu | Gln |
| | | | 100 | | | | | 105 | | | | | 110 | | |
| Leu | Pro | Ser | Ala | Lys | Glu | Ser | Pro | Ala | Lys | Phe | Leu | Glu | Val | Cys | Thr |
| | | 115 | | | | | 120 | | | | | 125 | | | |
| Trp | Val | Asp | Gln | Ile | Ala | Ala | Leu | Asn | Asp | Ser | Lys | Thr | Arg | Lys | Thr |
| 130 | | | | | 135 | | | | | 140 | | | | | |
| Thr | Ser | Glu | Thr | Val | Arg | Ala | Val | Leu | Asp | Ser | Leu | Ser | Glu | Lys | Lys |
| 145 | | | | 150 | | | | | 155 | | | | | 160 | |
| Lys | Ser | Ser | Pro | Ala | Ala | Asp | | | | | | | | | |
| | | | 165 | | | | | | | | | | | | |

```
<210> SEQ ID NO 272
<211> LENGTH: 9282
<212> TYPE: DNA
<213> ORGANISM: Homo sapiens

<400> SEQUENCE: 272
ggtgcggggc tgctggcggc tctgcagagt cgagagtggg agaagagcgg agcgtgtgag    60
cagtactgcg gcctcctctc ctctcctaac ctcgctctcg cggcctagct ttacccgccc   120
gcctgctcgg cgaccaggta agccccggga cggcccggtg tcacgcaagc gaggcgcgcc   180
gccctgctac cccgcgagg cgcgccgccc agcctctttt tcggctgcc tgccctcca    240
```

```
gtcccagccc tacgctgcgg cctctccggc ccatgcctga gatccggcat gagtgctcct    300
cccgcgtgct tccgccgctg gtggcttgga cccgtcgggg ctggcgctgg tggggcgcgc    360
ccttggccag gctctgggaa gggcggggtg agttgttttg atcttctttt cactacttgc    420
ggccgaagcg ccgcccctgg aggccgttgg gccggcctgc gccctgggc tcgcagtggt    480
ttgtttgcgc tgtggatgga gtggcggtgc ggtccctgt ggagcgcaaa caaggcgctt    540
ggttggcgcg ggcgcctggc tgccttcctc gtggtgggc cttcggagca atcgtcctgg    600
ttctggcgat ggttgagacg cctcgattgc ggcgtgtaac ggtgagcgtt gtttgggcgg    660
ccggctcccg cctcggggtc ccgggggcct ccaatgtga ccgaacaatg gagagcccgg    720
gcctcggcgc agtcagtgga gaagccggtc cgggcggagg cagcagcagc gcgcagtccc    780
tacggcctgc gccccaccc tccccggac ccccaaccc ctcggcggca gggtatggcc    840
acctccgtga ggccctgaga ttcggacggg ggcccgaggg gcagggcgcc cactttaggg    900
acatttcagt gggaaggggc tgctctcaaa gtggataatt ataactccct cgggggcggg    960
aagcggggat cctcccccag ccgcaagtcc acgaagaaaa caacgaatga aaattatgaa   1020
gacaacgaga agtcagactc ctccgggtcg cgctccagct gcttcggctt cgtcgcctac   1080
tctgtgaact ccggggagag atctcgagtc aagattaaga ccttaaccca ccaacctgcc   1140
tgttcggaca cccccggc cggccgctgt ctgtccccctt ctccatcgcc ctctcccaga   1200
aagctccggt gcttggacca gctagagtct gagaaagagg agaggcgcga acgccactcc   1260
aaaaagagaa gggttaaaga gggcaaccct aacgatacgc ttgactttct gtggctgggg   1320
tgagtgaggg ggcagggagg acgaccccgg agttggtggg agctgcagaa actgctgaaa   1380
acttcagaat ccatttcccc cacgtaaact tggcaccgca gcagcagcag ttgatagagt   1440
ggcactaggc tgctggcatg caactcggct cacggaaaag agcaagagat ccgaaactga   1500
ggcttaggac aaagtgtgca tgatattggt ggtgtaacat gttggagagg acagccgaga   1560
aattgggttg taggttttt tttttgttt tccgacagag tctctatctg ttacccaggt   1620
tggagtgcag tggtgcaatc tcccggctca ctgcaacctc tgcctctggg gttcaggcga   1680
ttctcctgtg tcagcctccc gagtagctgg gattacaggc gtgcacaacc acgcccggct   1740
aattttgta ttttagtag agacgggagt ttcatcgtgt tggccaggct ggtctcgaac   1800
tttgtacctc aggtgatctg cccgcttcgg tgggttgtag cttttagcgg gagctaaagg   1860
gttctgggat ggaggtggga agtaggattt ggccggctga gtcttctaga ggcaatattg   1920
gggtgttggt cttccccaag gggaagggtg gtgaggctga gggagaagca gttatgtttt   1980
cagctgggca aacatggacg gttgcccgta gaaactttgc cactgtactt cagaacgttg   2040
ccctagtcgt tggaggagaa caatgtgttc cctttctagc caccctggtc cacgagggga   2100
ggagggagag agagaatgtt tcctcttcgg ctgttgtggc ttgagagttt ctcttctttc   2160
ggaggttttg tggtagtggc tggcagttat tagtatgcct catggctttt aaatttccag   2220
atcttttga tttagaagtg gaaatttcct aattacttga caagtcttgt agaattccat   2280
aatgttgtga ttcttgccca ctatcttaag tgagactttg catgagacct atggaaatta   2340
tggcagcatt cccttagaa tctggcttga atcagctttt gtgtaggaaa ctgctagcct   2400
tctaaaaaa tatattgtaa ccttgtttca tcctcaaatc taaatgtgta atgagttttc   2460
ttttggtggg gaggggcggt gggtttgagt taagaccaca gctaggatga aagacaaaga   2520
gaaaacaaa ctgtggaagc caagcctgtt ctgtggctgg atttttactta tattggaaga   2580
agttctatgt tttgtaaatt tgtgtattgg ttttgatttg tttcctctga tagtttagta   2640
```

```
tttggatagt ttagtgttaa cctcagctac actgaaggaa tagaccttag tcctcacaag    2700
tataagttct agcttggaag cctgggttct gcagtagctg tggaacttaa gcctgtgagc    2760
tcagggatgc agaggcattg agttactacc aagggcctga tcttttcttt agcaggcatc    2820
tgtgttaatt gtttcaaaag gtggtgatca gttttacagc ctattataaa ggagattttt    2880
gcctactata aaactaatcc ccctgaaaga gtgagtaaac ataacttttt gtgtgttgac    2940
ttccacaagg gaaggagttg gcacttacac tctgactttt gattcagtcg tccttcttga    3000 gccattttg caggggatca gtttggagtg ggcgttaaca atgttattct ttttttcttc    3060
tccagaacac cttccaccat gaccacctca gcaagttccc acttaaataa aggcatcaag    3120
caggtgtaca tgtccctgcc tcagggtgag aaagtccagg ccatgtatat ctggatcgat    3180
ggtactggag aaggactgcg ctgcaagacc cggaccctgg acagtgagcc caagtgtgtg    3240
gaaggtgaga cagcaatgtg gagtggagca catgctgggt gggatctgca gaggggtggg    3300
cagcagcctt tgactcagcc tctgattagg gcctctttct tctgtttgta aaggttttct    3360
aaggcagggc ttttcagact ttattcagtc aacattaagc tcctacactg cctcaaagca    3420
gagcgacgat ggaacccttt atttcaatgg aattgtgcac gtaggccagt gtattgaaga    3480
aaaactaagt ctggtttatg gagagttggc atggggctta gaggttgccg acctggacat    3540
ccccacttag ctggctctaa ggcaccctca gaaaaccact gctctaacct gagaatgcca    3600
tctagtttac aaactcttag aaaactgtgt ttaatactca tatcactggc ttctagatgt    3660
gaagcaaatg ctctacaatg gtttttaaat aggactaatt tttagttgat gccacttttg    3720
gaaattctta aactaattgc gtatccctct aggagctaca gttagattat agttgtgacc    3780 ttcattttc agtctagaac aagccatagt cttccctctt ctggaaaggg gccgaggaa    3840 agtatcatat cctacctagt ttagggtagt ttacttttcc ttttttgagta agtgaatgat    3900 cataatacaa agcctatatt gtgtacttgc tatgtggcag atgatagtgc acagacactg    3960
aagatacaaa gtgagagtct cgtctctgcc ttcagagaac tcagtcagct agagagacca    4020
agcagccttc aaaacagtgg gaaaggtgga taggtgataa gggagcatcc tagagtaagt    4080
catcctgcta gtcgtctgtt ccctcatcta taaaataagg acataacttg ccagaataca    4140
ctgggggcat aagaaggatg caacacatta cctaatggaa gaatcagaat ccttcactat    4200
ctcaatattt taagtgattg ataggatggt agtgataaca gaatgcttca gcttgtctcc    4260
tggaagacat ttgggaaggg agtatctgat atatttcttt taaggaattg gtacaatggt    4320
cttacttgga actcaaatag gaagggctat aagatcaggt acaggtgcca gggtatacat    4380
attaatgatg gcatttatac cttaatgaat tcctggaaaa gagatattta gagatgggaa    4440
ggtgagtgaa gggctggctg tatttgcatt gcttggaaag ctcctgtatg ttttaaatgt    4500
aattttccct ctttttgccc cagagttgcc tgagtggaat ttcgatggct ctagtacttt    4560
acagtctgag ggttccaaca gtgacatgta tctcgtgcct gctgccatgt ttcgggaccc    4620
cttccgtaag gaccctaaca agctggtgtt atgtgaagtt ttcaagtaca atcgaaggcc    4680
tgcaggtgtg ttatagcaca gctatggata cccctcctca atctgtgaat gctgtgaagg    4740
ggagggagaa gacattctga aatcagcatt gggaagacta ggcaatttca gcactatttt    4800
aagaatctga gtgattcttt tccctgaact tctgctttga ggaagagata atatggccca    4860
tctttctatg gtcttctctg ttggttgcat aaaaatagcat tggatttgtc cagatctgtt    4920
tgccggtctt ggagtcccca gtaacagcct tcctgcctgg aatgtaggcc aggacaaatg    4980
```

```
taaaccaatg acaaatgtt tctcaaaaat tatagaatgg ctccaagtgc ctgagaaatg    5040
aagaataaat ctgacaacca gaagcagctg tcttgtgaat agagggttaa gtgcctggca    5100
tttggtgctt gggaggtggc cagaatgcag ataaggtgaa agttgccctg ttctaaatcc    5160
actcccatgt gacttggttg taactgagtt tagttaaaac tgaagtcttt cagagtcttc    5220
ctacagatgt acaattaaca gcttctctca tttttctgac tcggtgatcc caagaaggcc    5280
tatactgggt cagttcatac catagtgcac acctcagttg tatagaatcc aaggactatt    5340
ctcccatcag catcggtatt cagcatctat gtctttagat ccctgatggc gtattattga    5400
ctctttttc tagagaccaa tttgaggcac acctgtaaac ggataatgga catggtgagc    5460
aaccagcacc cctggtttgg catggagcag gagtataccc tcatgggac agatgggcac    5520
cccctttggtt ggccttccaa cggcttccca gggcccagg gtaagtctcc ttgggttaga    5580
ggtgaaattc ccagaagtgt ctaactgtgc aggaatgccc cttcccaggg atgggaatga    5640
ctttcagaat caagaagcaa aataatacag taaaggcgaa acagccctca catcaccaaa    5700
gtccaaaaat ggatatgaat atataaagta aggttttagg gggaacgttt ggccccactg    5760
aagctgtggt gaagaggaac tcccctattg ccctcccct gccccgcacc tgcagatgaa    5820
ggcaaggata gtgattcaag agggcaaggc ttaagggcct tctgatctct gactttggga    5880
ttctctggat ttcttgactc ttagtgtttt gtcctgatgc ttctgtaggt ccatattact    5940
gtggtgtggg agcagacaga gcctatggca gggacatcgt ggaggcccat taccgggcct    6000
gcttgtatgc tggagtcaag attgcgggga ctaatgccga ggtcatgcct gcccaggtaa    6060
gtatagctcc aatccatcaa tgaagaaggg taggtaggtg tacataggac ttttgctagt    6120
aagggctgct gatacaccac tcactaaccc aaaacctaag aacgggttgg agtacaggtg    6180
agaagagaac aggtttagga gattctgagt tggagtgagc agttagcttt gtttttaatgg    6240
ccaagcttct cgtttctagt gggaatttca gattggacct tgtgaaggaa tcagcatggg    6300
agatcatctc tgggtggccc gtttcatctt gcatcgtgtg tgtgaagact ttggagtgat    6360
agcaaccttt gatcctaagc ccattcctgg gaactggaat ggtgcaggct gccataccaa    6420
cttcagcacc aaggccatgc gggaggagaa tggtctgaag tgagtacctt ctgctggggc    6480
catctttaat ctcctgtggc agaaaacttg ggaggagact tagcaatctc tcagcaaagt    6540
ctcctttgca ggatgacttg caaatatttg ccaaagatga gtaaacttga cttctcagtc    6600
tggacgtact ttaggtgttg acacttgcct tcacattctc tcatttttgtt cctatttgaa    6660
aaataccaaa taatacttct gattcacagt gataaatatt tgttataatt tatataatat    6720
atattagtca tatatcatta tataaatata tatcgatata tatatttgtg acatatgtca    6780
tggtgacagg gaaaagttga caaattcatg catttgaaaa tcttttagaa ctaaattagt    6840
aacaatacag gcatgtggat aagcttaatg cttatgaggg ggagaaagtt tcaaatgatt    6900
agtctttca acaaacagta actttgtact gcttgtcggg cactgttctc accactgaga    6960
cacacaggta agaagatgca gccactgccc tcatgaagta tttgttctac tggtatcata    7020
ttttggtgca cttcattctt ggctccatac ctggagacaa ggttggactg ccatcttttc    7080
tgtttactct aggtacatcg aggaggccat gagaaaacta agcaagcggc accagtacca    7140
catccgtgcc tatgatccca agggaggcct ggacaatgcc cgacgtctaa ctggattcca    7200
tgaaacctcc aacatcaacg actttttctg tggtgtagcc aatcgtagcg ccagcatacg    7260
cattccccgg actgttggcc aggagaagaa gggttacttt gaagatcgtc gcccctctgc    7320
caactgcgac ccctttttcgg tgacagaagc cctcatccgc acgtgtcttc tcaatgaaac    7380
```

```
cggcgatgag cccttccagt acaaaaatta agtggactag acctccagct gttgagcccc    7440
tcctagttct tcatcccact ccaactcttc ccctctccc agttgtcccg attgtaactc    7500
aaagggtgga atatcaaggt cgttttttc attccatgtg cccagttaat cttgctttct    7560
ttgtttggct gggatagagg ggtcaagtta ttaatttctt cacacctacc ctccttttt    7620 tccctatcac tgaagctttt tagtgcatta gtggggagga gggtggggag acataaccac    7680
tgcttccatt taatgggtg cacctgtcca ataggcgtag ctatccggac agagcacgtt    7740
tgcagaaggg ggtctcttct tccaggtagc tgaaagggga agacctgacg tactctggtt    7800
aggttaggac ttgccctcgt ggtggaaact tttcttaaaa agttataacc aacttttcta    7860
ttaaaagtgg gaattaggag agaaggtagg ggttgggaat cagagagaat ggctttggtc    7920
tcttgcttgt gggactagcc tggcttggga ctaaatgccc tgctctgaac acgaagctta    7980
gtataaactg atggatatcc ctaccttgaa agaagaaaag gttcttactg cttggtcctt    8040
gatttatcac acaaagcaga atagtatttt tatatttaaa tgtaaagaca aaaaactata    8100
tgtatggttt tgtggattat gtgtgttttg ctaaaggaaa aaaccatcca ggtcacgggg    8160
caccaaattt gagacaaata gtcggattag aaataaagca tctcattttg agtagagagc    8220
aagggaagtg gttcttagat ggtgatctgg gattaggccc tcaagaccct tttgggtttc    8280
tgccctgccc accctctgga gaaggtgggc actggattag ttaacagaca acacgttact    8340
agcagtcact tgatctccgt ggctttggtt taaaagacac acttgtccac ataggtttag    8400
agataagagt tggctggtca acttgagcat gttactgaca gagggggtat tggggttatt    8460
ttctggtagg aatagcatgt cactaaagca ggcctttga tattaaattt tttaaaaagc    8520
aaaattatag aagtttagat tttaatcaaa tttgtagggt ttctaggtaa tttttacaga    8580
attgcttgtt tgcttcaact gtctcctacc tctgctcttg gaggagatgg ggacagggct    8640
ggagtcaaaa cacttgtaat tttgtatctt gatgtctttg ttaagactgc tgaagaatta    8700
ttttttttct tttataataa ggaataaacc ccacctttat tccttcattt catctaccat    8760
tttctggttc ttgtgttggc tgtggcaggc cagctgtggt tttctttgc catgacaact    8820 tctaattgcc atgtacagta tgttcaaagt caaataactc ctcattgtaa acaaactgtg    8880
taactgccca aagcagcact tataaatcag cctaacataa gatctctctg atgtgtttgt    8940
gattctttca aatccctatg tgccattata ttctttatt tcctaaaaca ggcaaaataa    9000
gctcaagttt atgtactctg agtttttaaa acactggagt gatgttgctg accagccgtt    9060
tcctgtacct ctctaagttg ggtatttggg acttaaggga ttaagttttt cacctagact    9120
tagttacaca caatcttggc atttcctagc ctagaggttt gtagcagggt acaagcccca    9180
ctcctccccc ttcctttgct cccctgagtt tggttttggc ttaccataac attgttttga    9240
ccattcctag cctaatacaa tagcctaaca taatgtaaga tt                      9282
```

MEGANUCLEASE VARIANTS CLEAVING A DNA TARGET SEQUENCE FROM A GLUTAMINE SYNTHETASE GENE AND USES THEREOF

The invention relates to a meganuclease variant cleaving a DNA target sequence from a Glutamine Synthetase (GS) gene, to a vector encoding said variant, to a cell, an animal or a plant modified by said vector and to the use of said meganuclease variant and derived products for genome engineering and for in vivo and ex vivo (gene cell therapy) genome therapy.

Glutamine Synthetase (GS), also called glutamate-ammonia ligase (GLUL), is a universal housekeeping enzyme responsible for the biosynthesis of glutamine from glutamate and ammonium, using the hydrolysis of ATP to ADP and phosphate to drive the reaction. As such, it represents an important link between the Krebs cycle and amino acid metabolism (Meister et al., 1980, Glutamine metabolism, enzymology and regulation, Academic Press, N.Y., p. 1-40 and 319-329). This enzymatic reaction is the pathway for glutamine formation in mammalian cells. In the absence of glutamine in the growth medium, the GS enzyme plays an essential role in the survival of mammalian cells in culture. Glutamine Synthetase is encoded by one of the oldest existing and functioning genes in the history of gene evolution and can be regarded as a key enzyme in the metabolism of prokaryotes and eukaryotes (Kumada et al., 2003, PNAS USA, 90: 3009-3013). Given its biological function, the GS gene is used as a positive selection marker for genome engineering (targeted and random gene manipulations).

GS is found at low levels (0.01%-0.1% of soluble protein) in most higher vertebrate cells and is found at higher levels (>1% of total protein) in certain specialized cell types such as hepatocytes, adipocytes and glial cells (Tiemeier et al., 1972, J. Biol. Chem., 247: 2272-2277; Gebhardt et al., 1983, EMBO J., 2: 567-570; Miller et al., 1978, PNAS USA, 75:1418-1422; Linser et al., 1979, PNAS USA, 76: 6476-6480). A variety of regulatory signals affect GS levels within cells, for instance glucocorticoid steroids and cAMP, and glutamine in a culture medium appears to regulate GS levels post-translationally (Milman et al., 1975, J. Biol. Chem., 250: 1393-1399; Arad et al., 1976, Cell, 8:59-101) via ADP ribosylation.

Some mammalian cell lines, such as mouse myeloma lines, do not express sufficient GS to survive without added glutamine. With these cell lines, a transfected GS gene can function as a selectable marker by permitting growth in a glutamine-free medium. Other cell lines, such as Chinese Hamster Ovary (CHO) cell lines, express sufficient GS to survive without exogenous glutamine. In these cases, a GS inhibitor, such as methionine sulphoximine (Msx), can be used to inhibit endogenous GS activity such that only transfectants with additional GS activity can survive.

Mammalian cells are attractive for protein production since such proteins are generally correctly folded, appropriately modified and completely functional, often in marked contrast to proteins expressed in bacterial cells.

A mammalian expression system, named GS System™, has been developed by Lonza Biologics using CHO-K1 cells for the production of a desired protein. CHO-K1 cells produce endogenous GS, but they can be used, to produce stable cell lines by transfecting in a GS gene and using a glutamine-free medium plus Msx (at sufficient levels to inhibit the endogenous enzyme) to provide selection pressure, along with the transfection of a gene of interest.

The GS System™ has been used to produce a wide variety of recombinant proteins, in particular therapeutic products which have been approved by regulatory authorities. Currently there are over 50 products in clinical trials and 5 products in-market that use the GS System™, such as Zenapax® (Roche) and Synagis® (MedImmune).

Nevertheless, the use of GS inhibitor in order to inhibit GS endogenous expression is not entirely satisfactory as a residual expression remains. This problem could be overcome by inactivating directly the endogenous GS gene. This inactivation could be achieved by using a site-specific endonuclease such as meganucleases which are able to create a DNA double-strand break (DSB) and cleave unique sites in living cells. This cleavage could be then repaired by Homologous Recombination (FIG. 3A) or Non Homologous End Joining (NHEJ) (FIG. 3B). Thus, an artificial meganuclease targeting the GS gene could be used to inactivate the GS gene.

Glutamine Synthetase is also ubiquitously expressed in the human organism with high concentrations in liver, brain and muscular tissues (Häussinger D et al., 1984, Glutamate Metabolism in Mammalian Tissues. Berlin: Springer Verlag, 3-15). GS plays a major role in ammonia and glutamate detoxification, interorgan nitrogen flux, pH homeostasis and cell signaling (Häussinger D, 1998, Adv Enzymol RAMB 72: 43-86). Inherited systemic deficiency of glutamine based on a defect of Glutamine Synthetase has been described (Häberle et al., 2006, J Inherit Metab Dis, 29, 352-358) in two newborns with an early fatal course of disease. Glutamine was largely absent in their serum, urine and cerebrospinal fluid. Homozygous mutations in exon 7 of the Glutamine Synthetase gene were detected in both of the patients. One patient carried an arginine324-to-cysteine substitution (R324C) and the other an arginine341-to-cysteine substitution (R341C). Glutamine Synthetase Enzymatic investigations confirmed that these mutations lead to a severely reduced Glutamine Synthetase activity.

Targeted homologous recombination should allow for the precise correction of mutations in situ (FIG. 3C). Therefore, an artificial meganuclease targeting the GS gene could be used for repairing the mutations associated with inherited systemic deficiency of glutamine.

Homologous recombination (HR), is a very conserved DNA maintenance pathway involved in the repair of DNA double-strand breaks (DSBs) and other DNA lesions (Rothstein, Methods Enzymol., 1983, 101, 202-211; Paques et al., Microbiol Mol Biol Rev, 1999, 63, 349-404; Sung et al., Nat. Rev. Mol. Cell. Biol., 2006, 7, 739-750) but it also underlies many biological phenomenon, such as the meiotic reassortiment of alleles in meiosis (Roeder, Genes Dev., 1997, 11, 2600-2621), mating type interconversion in yeast (Haber, Annu. Rev. Genet., 1998, 32, 561-599), and the "homing" of class I introns and inteins to novel alleles. HR usually promotes the exchange of genetic information between endogenous sequences, but in gene targeting experiments, it is used to promote exchange between an endogenous chromosomal sequence and an exogenous DNA construct. Basically, a DNA sharing homology with the targeted sequence is introduced into the cell's nucleus, and the endogenous homologous recombination machinery provides for the next steps (FIG. 3C).

Homologous gene targeting strategies have been used to knock out endogenous genes (Capecchi, M. R., Science, 1989, 244, 1288-1292, Smithies, O., Nature Medicine, 2001, 7, 1083-1086) or knock-in exogenous sequences in the chromosome. It can also be used for gene correction, and in principle, for the correction of mutations linked with monogenic diseases. However, this application is in fact difficult, due to the low efficiency of the process ($10^{-6}$ to $10^{-9}$ of transfected cells).

One of several strategies to enhance the efficiency of recombination is to deliver a DNA double-strand break in the targeted locus, using meganucleases. Meganucleases are by definition sequence-specific endonucleases recognizing large sequences (Thierry, A. and B. Dujon, Nucleic Acids Res., 1992, 20, 5625-5631). They can cleave unique sites in living cells, thereby enhancing gene targeting by 1000-fold or more in the vicinity of the cleavage site (Puchta et al., Nucleic Acids Res., 1993, 21, 5034-5040; Rouet et al., Mol. Cell. Biol., 1994, 14, 8096-8106; Choulika et al., Mol. Cell. Biol., 1995, 15, 1968-1973; Puchta et al., Proc. Natl. Acad. Sci. U.S.A., 1996, 93, 5055-5060; Sargent et al., Mol. Cell. Biol., 1997, 17, 267-277; Cohen-Tannoudji et al., Mol. Cell. Biol., 1998, 18, 1444-1448; Donoho, et al., Mol. Cell. Biol., 1998, 18, 4070-4078; Elliott et al., Mol. Cell. Biol., 1998, 18, 93-101). Such meganucleases could be used to correct mutations responsible for monogenic inherited diseases.

The most accurate way to correct a genetic defect is to use a repair matrix with a non mutated copy of the gene, resulting in a reversion of the mutation. However, the efficiency of gene correction decreases as the distance between the mutation and the DSB grows, with a five-fold decrease at a distance of 200 bp. Therefore, a given meganuclease can be used to correct only mutations in the vicinity of its DNA target (FIG. 3C).

An alternative, termed "exon knock-in" is featured in FIG. 3D. In this case, a meganuclease cleaving in the 5' part of the gene can be used to knock-in functional exonic sequences upstream of the deleterious mutation. Although this method places the transgene in its regular location, it also results in duplication of exons, whose long term impact remains to be evaluated. In addition, should naturally cis-acting elements be located in an intron downstream of the cleavage, their immediate environment would be modified and their proper function would also need to be explored. However, this method has a tremendous advantage: a single meganuclease could be used for many different mutations downstream of the meganuclease cleavage site.

However, although several hundreds of natural meganucleases, also referred to as "homing endonucleases" have been identified (Chevalier et al., 2001, Nucleic Acids Res., 29, 3757-3774), the repertoire of cleavable sequences is too limited to address the complexity of the genomes, and for example, there is no cleavable site in the GS gene. Theoretically, the making of artificial sequence specific endonucleases with chosen specificities could alleviate this limit. Therefore, the making of meganucleases with tailored specificities is under intense investigation.

Recently, fusion of Zinc-Finger Proteins (ZFPs) with the catalytic domain of the FokI, a class IIS restriction endonuclease, were used to make functional sequence-specific endonucleases (Smith et al., Nucleic Acids Res., 1999, 27, 674-681; Bibikova et al., Mol. Cell. Biol., 2001, 21, 289-297; Bibikova et al., Genetics, 2002, 161, 1169-1175; Bibikova et al., Science, 2003, 300, 764; Porteus, M. H. and D. Baltimore, Science, 2003, 300, 763-; Alwin et al., Mol. Ther., 2005, 12, 610-617; Urnov et al., Nature, 2005, 435, 646-651; Porteus, M. H., Mol. Ther., 2006, 13, 438-446).

The binding specificity of Cys2-His2 type Zinc-Finger Proteins, is easy to manipulate, probably because they represent a simple (specificity driven by essentially four residues per finger), and modular system (Pabo et al., Annu. Rev. Biochem., 2001, 70, 313-340; Jamieson et al., Nat. Rev. Drug Discov., 2003, 2, 361-368. Studies from the Pabo (Rebar, E. J. and C. O. Pabo, Science, 1994, 263, 671-673; Kim, J. S. and C. O. Pabo, Proc. Natl. Acad. Sci. USA, 1998, 95, 2812-2817), Klug (Choo, Y. and A. Klug, Proc. Natl. Acad. Sci. USA, 1994, 91, 11163-11167; Isalan M. and A. Klug, Nat. Biotechnol., 2001, 19, 656-660) and Barbas (Choo, Y. and A. Klug, Proc. Natl. Acad. Sci. USA, 1994, 91, 11163-11167; Isalan M. and A. Klug, Nat. Biotechnol., 2001, 19, 656-660) laboratories resulted in a large repertoire of novel artificial ZFPs, able to bind most G/ANNG/ANNG/ANN sequences.

Nevertheless, ZFPs might have their limitations, especially for applications requiring a very high level of specificity, such as therapeutic applications. The FokI nuclease activity in fusion acts as a dimer, but it was recently shown that it could cleave DNA when only one out of the two monomers was bound to DNA, or when the two monomers were bound to two distant DNA sequences (Catto et al., Nucleic Acids Res., 2006, 34, 1711-1720). Thus, specificity might be very degenerate, as illustrated by toxicity in mammalian cells (Porteus, M. H. and D. Baltimore, Science, 2003, 300, 763) and *Drosophila* (Bibikova et al., Genetics, 2002, 161, 1169-1175; Bibikova et al., Science, 2003, 300, 764.).

In the wild, meganucleases are essentially represented by homing endonucleases. Homing Endonucleases (HEs) are a widespread family of natural meganucleases including hundreds of proteins families (Chevalier, B. S. and B. L. Stoddard, Nucleic Acids Res., 2001, 29, 3757-3774). These proteins are encoded by mobile genetic elements which propagate by a process called "homing": the endonuclease cleaves a cognate allele from which the mobile element is absent, thereby stimulating a homologous recombination event that duplicates the mobile DNA into the recipient locus. Given their exceptional cleavage properties in terms of efficacy and specificity, they could represent ideal scaffolds to derive novel, highly specific endonucleases.

HEs belong to four major families. The LAGLIDADG family, named after a conserved peptidic motif involved in the catalytic center, is the most widespread and the best characterized group. Seven structures are now available. Whereas most proteins from this family are monomeric and display two LAGLIDADG motifs, a few have only one motif, and thus dimerize to cleave palindromic or pseudo-palindromic target sequences.

Although the LAGLIDADG peptide is the only conserved region among members of the family, these proteins share a very similar architecture (FIG. 1A). The catalytic core is flanked by two DNA-binding domains with a perfect two-fold symmetry for homodimers such as I-CreI (Chevalier, et al., Nat. Struct. Biol., 2001, 8, 312-316), I-MsoI (Chevalier et al., J. Mol. Biol., 2003, 329, 253-269) and I-CeuI (Spiegel et al., Structure, 2006, 14, 869-880) and with a pseudo symmetry for monomers such as I-SceI (Moure et al., J. Mol. Biol., 2003, 334, 685-69, I-DmoI (Silva et al., J. Mol. Biol., 1999, 286, 1123-1136) or I-AniI (Bolduc et al., Genes Dev., 2003, 17, 2875-2888). Both monomers and both domains (for monomeric proteins) contribute to the catalytic core, organized around divalent cations. Just above the catalytic core, the two LAGLIDADG peptides also play an essential role in the dimerization interface. DNA binding depends on two typical saddle-shaped αββαββα folds, sitting on the DNA major groove. Other domains can be found, for example in inteins such as PI-PfuI (Ichiyanagi et al., J. Mol. Biol., 2000, 300, 889-901) and PI-SceI (Moure et al., Nat. Struct. Biol., 2002, 9, 764-770), whose protein splicing domain is also involved in DNA binding.

The making of functional chimeric meganucleases, by fusing the N-terminal I-DmoI domain with an I-CreI monomer (Chevalier et al., Mol. Cell., 2002, 10, 895-905; Epinat et al., Nucleic Acids Res, 2003, 31, 2952-62; International PCT Applications WO 03/078619 and WO 2004/031346) have demonstrated the plasticity of LAGLIDADG proteins.

Different groups have also used a semi-rational approach to locally alter the specificity of the I-CreI (Seligman et al., Genetics, 1997, 147, 1653-1664; Sussman et al., J. Mol. Biol., 2004, 342, 31-41; International PCT Applications WO 2006/097784, WO 2006/097853, WO 2007/060495 and WO 2007/049156; Arnould et al., J. Mol. Biol., 2006, 355, 443-458; Rosen et al., Nucleic Acids Res., 2006, 34, 4791-4800; Smith et al., Nucleic Acids Res., 2006, 34, e149), I-SceI (Doyon et al., J. Am. Chem. Soc., 2006, 128, 2477-2484), PI-SceI (Gimble et al., J. Mol. Biol., 2003, 334, 993-1008) and I-MsoI (Ashworth et al., Nature, 2006, 441, 656-659).

In addition, hundreds of I-CreI derivatives with locally altered specificity were engineered by combining the semi-rational approach and High Throughput Screening:

Residues Q44, R68 and R70 or Q44, R68, D75 and I77 of I-CreI were mutagenized and a collection of variants with altered specificity at positions ±3 to 5 of the DNA target (5NNN DNA target) were identified by screening (International PCT Applications WO 2006/097784 and WO 2006/097853; Arnould et al., J. Mol. Biol., 2006, 355, 443-458; Smith et al., Nucleic Acids Res., 2006, 34, e149).

Residues K28, N30 and Q38, N30, Y33 and Q38 or K28, Y33, Q38 and S40 of I-CreI were mutagenized and a collection of variants with altered specificity at positions ±8 to 10 of the DNA target (10NNN DNA target) were identified by screening (Smith et al., Nucleic Acids Res., 2006, 34, e149; International PCT Applications WO 2007/060495 and WO 2007/049156).

Two different variants were combined and assembled in a functional heterodimeric endonuclease able to cleave a chimeric target resulting from the fusion of two different halves of each variant DNA target sequence (Arnould et al., precited; International PCT Applications WO 2006/097854 and WO 2007/034262), as illustrated on FIG. 1B.

Furthermore, residues 28 to 40 and 44 to 77 of I-CreI were shown to form two separable functional subdomains, able to bind distinct parts of a homing endonuclease half-site (Smith et al. Nucleic Acids Res., 2006, 34, e149; International PCT Applications WO 2007/049095 and WO 2007/057781).

The combination of mutations from the two subdomains of I-CreI within the same monomer allowed the design of novel chimeric molecules (homodimers) able to cleave a palindromic combined DNA target sequence comprising the nucleotides at positions ±3 to 5 and ±8 to 10 which are bound by each subdomain (Smith et al., Nucleic Acids Res., 2006, 34, e149; International PCT Applications WO 2007/049095 and WO 2007/057781).

The method for producing meganuclease variants and the assays based on cleavage-induced recombination in mammal or yeast cells, which are used for screening variants with altered specificity are described in the International PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458. These assays result in a functional LacZ reporter gene which can be monitored by standard methods.

The combination of the two former steps allows a larger combinatorial approach, involving four different subdomains. The different subdomains can be modified separately and combined to obtain an entirely redesigned meganuclease variant (heterodimer or single-chain molecule) with chosen specificity, as illustrated on FIG. 1C. In a first step, couples of novel meganucleases are combined in new molecules ("half-meganucleases") cleaving palindromic targets derived from the target one wants to cleave. Then, the combination of such "half-meganucleases" can result in a heterodimeric species cleaving the target of interest. The assembly of four sets of mutations into heterodimeric endonucleases cleaving a model target sequence or a sequence from the human RAG1, XPC and HPRT genes have been described in Smith et al. (Nucleic Acids Res., 2006, 34, e149), Arnould et al., (J. Mol. Biol., 2007, 371, 49-65), and WO2008/059382 respectively.

These variants can be used to cleave genuine chromosomal sequences and have paved the way for novel perspectives in several fields, including gene therapy.

However, even though the base-pairs ±1 and ±2 do not display any contact with the protein, it has been shown that these positions are not devoid of content information (Chevalier et al., J. Mol. Biol., 2003, 329, 253-269), especially for the base-pair ±1 and could be a source of additional substrate specificity (Argast et al., J. Mol. Biol., 1998, 280, 345-353; Jurica et al., Mol. Cell., 1998, 2, 469-476; Chevalier, B. S. and B. L. Stoddard, Nucleic Acids Res., 2001, 29, 3757-3774). In vitro selection of cleavable I-CreI targets (Argast et al., precited) randomly mutagenized, revealed the importance of these four base-pairs on protein binding and cleavage activity. It has been suggested that the network of ordered water molecules found in the active site was important for positioning the DNA target (Chevalier et al., Biochemistry, 2004, 43, 14015-14026). In addition, the extensive conformational changes that appear in this region upon I-CreI binding suggest that the four central nucleotides could contribute to the substrate specificity, possibly by sequence dependent conformational preferences (Chevalier et al., 2003, precited).

Thus, it was not clear if variants identified on 10NNN and 5NNN DNA targets as homodimers cleaving a palindromic sequence with the four central nucleotides being gtac, would allow the design of new endonucleases that would cleave targets containing changes in the four central nucleotides.

The Inventor has identified a series of DNA targets in the GS gene that could be cleaved by I-CreI variants (FIGS. 18 to 20). The combinatorial approach, as illustrated in FIG. 1D was used to entirely redesign the DNA binding domain of the I-CreI protein and thereby engineer novel meganucleases with fully engineered specificity, to cleave one DNA target (GSCHO1). The GSCHO1 target is present in both mouse (FIG. 2A) and Chinese Hamster (*Criteculus griseus*; FIG. 2B) GS genes and differs from the I-CreI C1221 22 bp palindromic site by 15 nucleotides including two (positions +1, +2) out of the four central nucleotides (FIG. 4).

In a first step, couples of novel meganucleases are combined in new molecules ("half-meganucleases") cleaving palindromic targets derived from the target one wants to cleave. Then, the combination of such "half-meganucleases" can result in a heterodimeric species cleaving the target of interest. The assembly of four sets of mutations into heterodimeric endonucleases cleaving a model target sequence or a sequence from the human RAG1 gene has been described previously in Smith et al., Nucleic Acids Res., 2006, 34, e149.

Even though the combined variants were initially identified towards nucleotides 10NNN and 5NNN respectively, and a strong impact of the four central nucleotides of the target on the activity of the engineered meganuclease was observed, functional meganucleases with a profound change in specificity were selected. Furthermore, the activity of the engineered protein could be significantly improved by random and/or site-directed mutagenesis and screening, to compare with the activity of the I-CreI protein.

These I-CreI variants which are able to cleave a genomic DNA target from the GS gene can be used for inactivating the GS locus (knock-out and knock-in) (FIGS. 3A and 3B), thus allowing GS to be used as a selectable marker for genome engineering at any locus, for example for making transgenic animals and recombinant cell lines. In addition, these I-CreI variants could be used for repairing the GS mutations associated with inherited systemic deficiency of glutamine (FIGS. 3C and 3D).

The invention relates to an I-CreI variant wherein at least one of the two I-CreI monomers has at least two substitutions, one in each of the two functional subdomains of the LAGLIDADG core domain situated respectively from positions 28 to 40 and 44 to 77 of I-CreI, and is able to cleave a DNA target sequence from the GS gene.

The cleavage activity of the variant according to the invention may be measured by any well-known, in vitro or in vivo cleavage assay, such as those described in the International PCT Application WO 2004/067736; Epinat et al., Nucleic Acids Res., 2003, 31, 2952-2962; Chames et al., Nucleic Acids Res., 2005, 33, e178; Arnould et al., J. Mol. Biol., 2006, 355, 443-458, and Arnould et al., J. Mol. Biol., 2007, 371, 49-65. For example, the cleavage activity of the variant of the invention may be measured by a direct repeat recombination assay, in yeast or mammalian cells, using a reporter vector. The reporter vector comprises two truncated, non-functional copies of a reporter gene (direct repeats) and the genomic (non-palindromic) DNA target sequence within the intervening sequence, cloned in yeast or in a mammalian expression vector. Usually, the genomic DNA target sequence comprises one different half of each (palindromic or pseudo-palindromic) parent homodimeric I-CreI meganuclease target sequence. Expression of the heterodimeric variant results in a functional endonuclease which is able to cleave the genomic DNA target sequence. This cleavage induces homologous recombination between the direct repeats, resulting in a functional reporter gene, whose expression can be monitored by an appropriate assay. The cleavage activity of the variant against the genomic DNA target may be compared to wild type I-CreI or I-SceI activity against their natural target.

Definitions

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "meganuclease", is intended an endonuclease having a double-stranded DNA target sequence of 12 to 45 bp. Said meganuclease is either a dimeric enzyme, wherein each domain is on a monomer or a monomeric enzyme comprising the two domains on a single polypeptide.

by "meganuclease domain" is intended the region which interacts with one half of the DNA target of a meganuclease and is able to associate with the other domain of the same meganuclease which interacts with the other half of the DNA target to form a functional meganuclease able to cleave said DNA target.

by "meganuclease variant" or "variant" is intended a meganuclease obtained by replacement of at least one residue in the amino acid sequence of the wild-type meganuclease (natural meganuclease) with a different amino acid.

by "functional variant" is intended a variant which is able to cleave a DNA target sequence, preferably said target is a new target which is not cleaved by the parent meganuclease. For example, such variants have amino acid variation at positions contacting the DNA target sequence or interacting directly or indirectly with said DNA target.

by "I-CreI" is intended the wild-type I-CreI having the sequence of pdb accession code 1g9y, corresponding to the sequence SEQ ID NO: 1 in the sequence listing.

by "I-CreI variant with novel specificity" is intended a variant having a pattern of cleaved targets different from that of the parent meganuclease. The terms "novel specificity", "modified specificity", "novel cleavage specificity", "novel substrate specificity" which are equivalent and used indifferently, refer to the specificity of the variant towards the nucleotides of the DNA target sequence.

by "I-CreI site" is intended a 22 to 24 bp double-stranded DNA sequence which is cleaved by I-CreI. I-CreI sites include the wild-type (natural) non-palindromic I-CreI homing site and the derived palindromic sequences such as the sequence 5'-$t_{-12}c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}t_{+10}g_{+11}a_{+12}$ (SEQ ID NO: 2), also called C1221 (FIG. 4).

by "domain" or "core domain" is intended the "LAGLIDADG homing endonuclease core domain" which is the characteristic $\alpha_1\beta_1\beta_2\alpha_2\beta_3\beta_4\alpha_3$ fold of the homing endonucleases of the LAGLIDADG family, corresponding to a sequence of about one hundred amino acid residues. Said domain comprises four beta-strands ($\beta_1\beta_2\beta_3\beta_4$) folded in an anti-parallel beta-sheet which interacts with one half of the DNA target. This domain is able to associate with another LAGLIDADG homing endonuclease core domain which interacts with the other half of the DNA target to form a functional endonuclease able to cleave said DNA target. For example, in the case of the dimeric homing endonuclease I-CreI (163 amino acids), the LAGLIDADG homing endonuclease core domain corresponds to the residues 6 to 94.

by "subdomain" is intended the region of a LAGLIDADG homing endonuclease core domain which interacts with a distinct part of a homing endonuclease DNA target half-site.

by "beta-hairpin" is intended two consecutive beta-strands of the antiparallel beta-sheet of a LAGLIDADG homing endonuclease core domain ($\beta_1\beta_2$ or, $\beta_3\beta_4$) which are connected by a loop or a turn, by "single-chain meganuclease", "single-chain chimeric meganuclease", "single-chain meganuclease derivative", "single-chain chimeric meganuclease derivative" or "single-chain derivative" is intended a meganuclease comprising two LAGLIDADG homing endonuclease domains or core domains linked by a peptidic spacer. The single-chain meganuclease is able to cleave a chimeric DNA target sequence comprising one different half of each parent meganuclease target sequence.

by "DNA target", "DNA target sequence", "target sequence", "target-site", "target", "site"; "site of interest"; "recognition site", "recognition sequence", "homing recognition site", "homing site", "cleavage site" is intended a 20 to 24 bp double-stranded palindromic, partially palindromic (pseudo-palindromic) or non-palindromic polynucleotide sequence that is recognized and cleaved by a LAGLIDADG homing endonuclease such as I-CreI, or a variant, or a single-chain chimeric meganuclease derived from I-CreI. These terms refer to a distinct DNA location, preferably a genomic location, at which a double stranded break (cleavage) is to be induced by the meganuclease. The DNA target is defined by the 5' to 3' sequence of one strand of the double-stranded polynucleotide, as indicate above for C1221. Cleavage of the DNA target occurs at the nucleotides at positions +2 and −2, respectively for the sense and the antisense strand. Unless otherwise indicated, the position at which cleavage of the DNA target by an I-Cre I meganuclease variant occurs, corresponds to the cleavage site on the sense strand of the DNA target.

by "DNA target half-site", "half cleavage site" or "half-site" is intended the portion of the DNA target which is bound by each LAGLIDADG homing endonuclease core domain.

by "chimeric DNA target" or "hybrid DNA target" is intended the fusion of different halves of two parent meganuclease target sequences. In addition at least one half of said target may comprise the combination of nucleotides which are bound by at least two separate subdomains (combined DNA target).

by "GS gene" is intended a Glutamine Synthetase or Glutamate-Ammonia Ligase (GLUL) gene, preferably the GS gene of a vertebrate, more preferably the GS gene of a mammal such as human, mouse and Chinese Hamster (*Criteculus griseus*) GS genes. GS gene sequences are available in sequence databases, such as the NCBI/GenBank database. The human GS gene sequence (9282 bp; SEQ ID NO: 272) is available under accession number NC_000001.9 (reverse complement of positions 180618292 to 180627573). The mouse GS gene sequence (9770 bp; SEQ ID NO: 3) is available under accession number NC_000067.5 (reverse complement of positions 155747075 to 155756844). Both genes have 7 exons. The mouse GS gene is illustrated by FIG. 2A (Exon 1 (positions 1 to 115), Exon 2 (positions 2990 to 3168), Exon 3 (positions 4593 to 4754), Exon 4 (positions 6405 to 6551), Exon 5 (positions 7076 to 7203), Exon 6 (positions 7342 to 7541) and Exon 7 (positions 7920 to 9770)). The human GS gene comprises: Exon 1 (positions 1 to 137), Exon 2 (positions 3066 to 3244), Exon 3 (positions 4524 to 4685), Exon 4 (positions 5414 to 5560), Exon 5 (positions 5929 to 6056), Exon 6 (positions 6260 to 6459) and Exon 7 (positions 7093 to 9282). The ORF which is from the beginning of Exon 2 (positions 3003 (mouse GS)) or 3079 (human GS)) to the beginning of Exon 7 (positions 8238 (mouse GS) or 7411 (human GS)), is flanked by long untranslated regions, respectively at the 5' and 3' end. The mouse gene is transcribed into a 2782 bp mRNA (GenBank NM_008131) containing the GS ORF from positions 129 to 1250. The Chinese Hamster (*Criteculus griseus*) GS mRNA is a 1421 bp sequence (accession number GenBank X03495) containing the GS ORF from positions 147 to 1268 (FIG. 2B).

by "DNA target sequence from the GS gene", "genomic DNA target sequence", "genomic DNA cleavage site", "genomic DNA target" or "genomic target" is intended a 20 to 24 bp sequence of a GS gene as defined above, which is recognized and cleaved by a meganuclease variant or a single-chain chimeric meganuclease derivative.

by "vector" is intended a nucleic acid molecule capable of transporting another nucleic acid to which it has been linked.

by "homologous" is intended a sequence with enough identity to another one to lead to homologous recombination between sequences, more particularly having at least 95% identity, preferably 97% identity and more preferably 99%.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

by mutation is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

The variant according to the present invention may be a homodimer or a heterodimer. Preferably, both monomers of the heterodimer are mutated at positions 28 to 40 and/or 44 to 77. More preferably, both monomers have different substitutions both at positions 28 to 40 and 44 to 77 of I-CreI.

In a preferred embodiment of said variant, said substitution(s) in the subdomain situated from positions 44 to 77 of I-CreI are at positions 44, 68, 70, 75 and/or 77.

In another preferred embodiment of said variant, said substitution(s) in the subdomain situated from positions 28 to 40 of I-CreI are at positions 28, 30, 32, 33, 38 and/or 40.

In another preferred embodiment of said variant, it comprises one or more mutations at positions of other amino acid residues that contact the DNA target sequence or interact with the DNA backbone or with the nucleotide bases, directly or via a water molecule; these residues are well-known in the art (Jurica et al., Molecular Cell., 1998, 2, 469-476; Chevalier et al., J. Mol. Biol., 2003, 329, 253-269). In particular, additional substitutions may be introduced at positions contacting the phosphate backbone, for example in the final C-terminal loop (positions 137 to 143; Prieto et al., Nucleic Acids Res., Epub 22 Apr. 2007). Preferably said residues are involved in binding and cleavage of said DNA cleavage site. More preferably, said residues are at positions 138, 139, 142 or 143 of I-CreI. Two residues may be mutated in one variant provided that each mutation is in a different pair of residues chosen from the pair of residues at positions 138 and 139 and the pair of residues at positions 142 and 143. The mutations which are introduced modify the interaction(s) of said amino acid(s) of the final C-terminal loop with the phosphate backbone of the I-CreI site. Preferably, the residue at position 138 or 139 is substituted by a hydrophobic amino acid to avoid the formation of hydrogen bonds with the phosphate backbone of the DNA cleavage site. For example, the residue at position 138 is substituted by an alanine or the residue at position 139 is substituted by a methionine. The residue at position 142 or 143 is advantageously substituted by a small amino acid, for example a glycine, to decrease the size of the side chains of these amino acid residues. More, preferably, said substitution in the final C-terminal loop modify the specificity of the variant towards the nucleotide at positions ±1 to 2, ±6 to 7 and/or ±11 to 12 of the I-CreI site.

In another preferred embodiment of said variant, it comprises one or more additional mutations that improve the binding and/or the cleavage properties of the variant towards the DNA target sequence from the GS gene.

The additional residues which are mutated may be on the entire I-CreI sequence, and in particular in the C-terminal half of I-CreI (positions 80 to 163). Both I-CreI monomers are advantageously mutated; the mutation(s) in each monomer may be identical or different. For example, the variant comprises one or more additional substitutions at positions: 2, 3, 6, 7, 12, 19, 24, 35, 39, 43, 45, 47, 50, 54, 57, 59, 60, 64, 66, 80, 87, 92, 96, 105, 107, 110, 114, 117, 118, 119, 120, 125, 129, 132, 137, 139, 153, 154, 160 and 161. Said substitutions are advantageously selected from the group consisting of: N2S, T3A, N6K, K7E, Y12H, G19S, G19A, I24V, F35L, L39V, F43L, V45L, V45M, Q47K, Q50R, F54L, K57E, V59A, D60Y, V64A, Y66H, E80K, F87L, F87I, Q92R, K96R, V105A, K107R, E110V, S114F, S114P, E117V, S118T, P119L, D120A, D120E, V125I, V129A, I132V, D137N, D137Y, K139R, D153N, S154G, K160R, S161P and S161T. More preferably, the variant comprises at least one substitution selected from the group consisting of: G19S, F54L, E80K, F87L, V105A and I132V. The variant may also comprise additional residues at the C-terminus. For example a glycine (G) and/or a proline (P) residue may be inserted at positions 164 and 165 of I-CreI, respectively.

According to a more preferred embodiment of said variant, said additional mutation further impairs the formation of a functional homodimer. More preferably, said mutation is the G19S mutation. The G19S mutation is advantageously introduced in one of the two monomers of a heterodimeric I-CreI variant, so as to obtain a meganuclease having enhanced cleavage activity and enhanced cleavage specificity. In addition, to enhance the cleavage specificity further, the other monomer may carry a distinct mutation that impairs the formation of a functional homodimer or favors the formation of the heterodimer.

In another preferred embodiment of said variant, said substitutions are replacement of the initial amino acids with amino acids selected from the group consisting of: A, D, E, G, H, K, N, P, Q, R, S, T, Y, C, V, L, M, F, I and W.

The variant of the invention may be derived from the wild-type I-CreI (SEQ ID NO: 1) or an I-CreI scaffold protein having at least 85% identity, preferably at least 90% identity, more preferably at least 95% identity with SEQ ID NO: 1, such as the scaffold called I-CreI N75 (167 amino acids; SEQ ID NO: 4) having the insertion of an alanine at position 2, and the insertion of AAD at the C-terminus (positions 164 to 166) of the I-CreI sequence.

In addition, the variants of the invention may include one or more residues inserted at the NH$_2$ terminus and/or COOH terminus of the sequence. For example, a tag (epitope or polyhistidine sequence) is introduced at the NH$_2$ terminus and/or COOH terminus; said tag is useful for the detection and/or the purification of said variant. The variant may also comprise a nuclear localization signal (NLS); said NLS is useful for the importation of said variant into the cell nucleus. The NLS may be inserted just after the first methionine of the variant or just after an N-terminal tag.

The variant according to the present invention may be a homodimer which is able to cleave a palindromic or pseudo-palindromic DNA target sequence.

Alternatively, said variant is a heterodimer, resulting from the association of a first and a second monomer having different substitutions at positions 28 to 40 and 44 to 77 of I-CreI, said heterodimer being able to cleave a non-palindromic DNA target sequence from the GS gene.

The DNA target sequences which are cleaved by the I-CreI variants are present in at least one mammalian GS gene selected from the group consisting of the human, mouse and/or Chinese Hamster (*Criteculus griseus*) GS genes. The DNA target sequences are situated in the GS ORF and these sequences cover all the GS ORF (FIGS. 18 to 20).

For example, the DNA target sequences SEQ ID NO: 5 to 28 (FIG. 18) are present in the human GS gene. The DNA target sequences SEQ ID NO: 19 and 29 to 48 are present in the mouse GS gene (FIG. 19). The DNA target sequences SEQ ID NO: 19, 29, 30, 34, 46, 47 and 49 to 60 are present in the Chinese Hamster GS gene (FIG. 20).

The DNA target sequence SEQ ID NO: 19 is present in the human, mouse and Chinese Hamster GS genes. Therefore, the I-CreI variants which cleave the DNA target sequence SEQ ID NO: 19 are able to induce a site-specific modification in the human, mouse and Chinese Hamster GS genes. The DNA target sequences SEQ ID NO: 29, 30, 34, 46 and 47 are present in both mouse and Chinese Hamster GS genes. Therefore, the I-CreI variants which cleave the DNA target sequences SEQ ID NO: 29, 30, 34, 46 and 47 are able to induce a site-specific modification in the mouse and Chinese Hamster GS genes.

In addition, the human, mouse and Chinese. Hamster DNA target sequences SEQ ID NO: 7, 31 and 49 have sequence identity at the nucleotide positions ±3 to 5 and ±8 to 10. Therefore, the I-CreI variants which cleave the DNA target sequence SEQ ID NO: 49 are able to induce a site-specific modification in the Chinese Hamster and for some of them, also in the human and/or mouse GS gene.

Examples of heterodimeric variants which cleave each DNA target are presented in FIGS. 18 to 20 and Tables I to III.

TABLE I

Sequence of heterodimeric I-CreI variants cleaving a DNA target from the human GS gene

| First I-CreI variant Sequence (SEQ ID NO: 61 to 84) | Second I-CreI variant Sequence (SEQ ID NO: 85 to 108) | Target Exon | SEQ ID NO: |
|---|---|---|---|
| 30T 33G 44V 68E 75N 77R 80K KTSGQS/VERNR + K80 | 30R 32T 33N 40Q 44D 70S 75R 77T KRTNQQ/DRSRT | 2 | 5 |
| 32G 33C 38A 44I 70S 75N 77R KNGCAS/IRSNR | 33R 38D 40R 44Y 68A 70S 75R KNSRDR/YASRI | 2 | 6 |

TABLE I-continued

Sequence of heterodimeric I-CreI variants cleaving a DNA target from the human GS gene

| First I-CreI variant Sequence (SEQ ID NO: 61 to 84) | Second I-CreI variant Sequence (SEQ ID NO: 85 to 108) | Exon | Target SEQ ID NO: |
|---|---|---|---|
| 30R 32T 33C 40T 44K 68Y 70S 75E 77V KRTCQT/KYSEV | 30R 32T 33N 40Q 44L 70N 75N 80K KRTNQQ/LRNNI + K80 | 2 | 7 |
| 33C 38A 44N 68T 70S 75R 77Y KNSCAS/NTSRY | 33T 38A 44M 68E 75N 77R KNSTAS/MERNR | 2 | 8 |
| 33R 38N 40Q 44R 68Y 70S 75E 77V KNSRNQ/RYSEV | 28E 33R 38R 40K 44N 70S 75R 77Y ENSRRK/NRSRY | 2 | 9 |
| 32T 33C 44L 70A 75N 77V KNTCQS/LRANV | 30Y 32T 33C 44D 68Y 70S 75S 77R KYTCQS/DYSSR | 2 | 10 |
| 32H 33H 44N 68Q 70S 75S 77V KNHHQS/NQSSV | 33E 40E 44A 68Y 70S 75Y 77K KNSEQE/AYSYK | 3 | 11 |
| 30R 32C 33C 40E 44K 68T 70T 75N KRCCQE/KTTNI | 32R 33D 44A 70S 75R 77L KNRDQS/ARSRL | 4 | 12 |
| 30R 68E 70S 75R 77R KRSYQS/QESRR | 30S 33H 38K 44N 68Y 70S 75R 77V KSSHKS/NYSRV | 4 | 13 |
| 33T 44A 70S 75E 77R KNSTQS/ARSER | 33P 40Q 44K 68Y 70S 75E 77V KNSPQQ/KYSEV | 4 | 14 |
| 30D 33R 38T 44R 70S 75N 77D KDSRTS/RRSND | 32C 33C 38H 44R 70S 75N 77D KNCCHS/RRSND | 5 | 15 |
| 32H 33H 44Y 68Y 70S 75S 77T KNHHQS/YYSST | 30T 33G 70S 75Y 77R KTSGQS/QRSYR | 5 | 16 |
| 30T 33G 44K 70S 75R 77R KTSGQS/KRSRR | 33R 38A 40Q 44N 70S 75R 77Y KNSRAQ/NRSRY | 5 | 17 |
| 44K 68Y 70S 75N 77Q KNSYQS/KYSNQ | 28E 33R 38R 40K 44K 68Y 70S 75Q 77N ENSRRK/KYSQN | 6 | 18 |
| <u>30S 33H 38K 44I 70S 75N 77R KSSHKS/IRSNR</u> | <u>32D 38C 44K 68E 70S 77R KNDYCS/KESDR</u> | 6 | 19 |
| 33T 40T 68N 70S 75Q 77R KNSTQT/QNSQR | 33R 38A 40Q 44A 68Q 70N 75N KNSRAQ/AQNNI | 7 | 20 |
| 33R 38D 40R 44I 70C 75N 77R KNSRDR/IRCNR | 30R 32A 33N 40E 44A 70S 75E 77R KRANQE/ARSER | 7 | 21 |
| 33P 38K 44N 68K 70H 75N KNSPKS/NKHNI | 28R 33A 38Y 40Q 44D 68Y 70S 75S 77R RNSAYQ/DYSSR | 7 | 22 |
| 33C 38A 44I 70A 75N 77R KNSCAS/IRANR | 32T 33C 70S 75H 77Y KNTCQS/QRSHY | 7 | 23 |
| 32T 38W 44A 70S 75R 77L KNTYWS/ARSRL | 33R 38N 40Q 44Y 68S 70S 75S 77D KNSRNQ/YSSSD | 7 | 24 |
| 30D 33R 38S 44Y 70S 77V KDSRSS/YRSDV | 32T 38W 44D 68Y 70S 75S 77R KNTYWS/DYSSR | 7 | 25 |
| 30T 33G 44K 70S 77K KTSGQS/KRSDK | 28N 33S 38R 40K 44A 68Y 70S 75R NNSSRK/AYSRI | 7 | 26 |
| 33R 38N 40Q 44S 70S 75Y 77T KNSRNQ/SRSYT | 30D 33R 44K 68E 70S 77R KDSRQS/KESDR | 7 | 27 |
| 33C 38A 44A 70S 75E 77R KNSCAS/ARSER | 30R 33R 68Y 75N KRSRQS/QYRNI | 7 | 28 |

* the underlined variants can cleave the identical target found in the GS gene of another species.

TABLE II

Sequence of heterodimeric I-CreI variants cleaving a DNA target from the mouse GS gene

| First I-CreI variant Sequence (SEQ ID NO: 109 to 123, 75, 124 to 128) | Second I-CreI variant Sequence (SEQ ID NO: 129 to 146, 99, 147 to 151) | Target Exon | SEQ ID NO: |
|---|---|---|---|
| 32C 33C 38H 44K 68Y 70S 75N KNCCHS/KYSNI | 30R 44T 68Y 70S 75R 77T KRSYQS/TYSRT | 2 | 29 |
| 30R 33R 38E 44D 68Y 70S 75Y 77Q KRSRES/DYSYQ | 30R 32G 44R 68H KRGYQS/RHRDI | 2 | 30 |
|  | 30R 32G 44K 68H KRGYQS/KHRDI |  |  |
|  | 30R 32G 44K 68N KRGYQS/KNRDI |  |  |
|  | 30R 32C 44R 68H KRCYQS/RHRDI |  |  |
| 30H 32H 33C 40T 44R 68Y 70S 75E 77V KHHCQT/RYSEV | 30R 32T 33N 40Q 44I 70C 75N 77R KRTNQQ/IRCNR | 2 | 31 |
| 33R 38A 40Q 44R 68Y 70S 75E 77R KNSRAQ/RYSER | 33H 38A 44V 68E 75N 77R 80K KNSHAS/VERNR + K80 | 2 | 32 |
| 30R 32G 33R 40A 44R 68Y 70S 75E 77R KRGRQA/RYSER | 32R 33D 44T 68Y 70S 75R 77T KNRDQS/TYSRT | 3 | 33 |
| 44L 70N 75N 80K KNSYQS/LRNNI + K80 | 24V 44N 68Y 70S 75Y 77N KNSYQS/NYSYN + V24 | 4 | 34 |
| 30D 33R 44Y 70S 77V KDSRQS/YRSDV | 30H 32H 33C 38A 44D 70S 75R 77Q KHHCAS/DRSRQ | 4 | 35 |
| 33T 44D 68Y 70S 75S 77R KNSTQS/DYSSR | 33R 38A 40Q 44R 68N 70S 75Q KNSRAQ/RNSQI | 4 | 36 |
| 32H 33H 68H 70S 75N 77R KNHHQS/QHSNR | 33G 40Q 68Y 70S 75R 77V KNSGQQ/QYSRV | 5 | 37 |
| 30D 33R 38T 44A 68Y 70S 75Y 77K KDSRTS/AYSYK | 30R 32T 44R 68S 70S 75N 77T KRTYQS/RSSNT | 5 | 38 |
| 33C 40Q 70S 75N 77R KNSCQQ/QRSNR | 32D 38Y 44T 68Y 70S 75R 77V KNDYYS/TYSRV | 6 | 39 |
| 30R 44R 68Y 70S 75E 77Q KRSYQS/RYSEQ | 38R 40K 44K 68S 70S 75N KNSYRK/KSSNI | 6 | 40 |
| 33C 38A 44N 68Y 70S 75R 77V KNSCAS/NYSRV | 32T 68H 70S 75N 77R KNTYQS/QHSNR | 6 | 41 |
| 33S 38R 40D 70S 75N KNSSRD/QRSNI | 44K 68E 70S 77R KNSYQS/KESDR | 6 | 42 |
| 32T 33C 44E 68C 70S 75N KNTCQS/ECSNI | 32N 33G 44K 68Y 70S 75N KNNGQS/KYSNI | 6 | 43 |
| 30S 33H 38K 44I 70S 75N 77R KSSHKS/IRSNR | 32D 38C 44K 68E 70S 77R KNDYCS/KESDR | 6 | 19 |
| 30T 33H 38R 44N 70S 75R 77Y KTSHRS/NRSRY | 32T 38W 44D 68Y 70S 75S 77R KNTYWS/DYSSR | 7 | 44 |
| 30S 33S 38H 44A 68Y 70S 75R 77V KNSYHS/AYSRV | 30D 33R 38G 68N 70S 75R 77V KDSRGS/QNSRV | 7 | 45 |
| 30D 33R 44K 68E 70S 77R KDSRQS/KESDR | 28N 38R 40K 44A 75N NNSYRK/ARRNI | 7 | 46 |

TABLE II-continued

Sequence of heterodimeric I-CreI variants cleaving a DNA target from the mouse GS gene

| First I-CreI variant Sequence (SEQ ID NO: 109 to 123, 75, 124 to 128) | Second I-CreI variant Sequence (SEQ ID NO: 129 to 146, 99, 147 to 151) | Target Exon | SEQ ID NO: |
|---|---|---|---|
| <u>33R 38N 40Q 44A 70S 75R 77L</u><br><u>KNSRNQ/ARSRL</u> | <u>30W 33C 44K 68A 70S 77K</u><br><u>KWSCQS/KASDK</u> | 7 | <u>47</u> |
| 30G 38K 44T 70S 75E 77R<br>KGSYKS/TRSER | 38G 40Q 44K 68Y 70S 75N 77Q<br>KNSYGQ/KYSNQ | 7 | 48 |

\* the underlined variants can cleave the identical target found in the Chinese Hamster GS gene.

TABLE III

Sequence of heterodimeric I-CreI variants cleaving a DNA target from the Chinese Hamster GS gene

| First I-CreI variant Sequence (SEQ ID NO: 109, 110, 152 to 155, 114, 156 to 159, 75 160 to 162, 126, 127, 163) | Second I-CreI variant Sequence (SEQ ID NO: 129 to 133, 164 to 167, 137, 168 to 171, 99, 172 to 174, 149, 150, 175) | Target Exon | SEQ ID NO: |
|---|---|---|---|
| <u>32C 33C 38H 44K 68Y 70S 75N</u><br><u>KNCCHS/KYSNI</u> | 30R 44T 68Y 70S 75R 77T<br>KRSYQS/TYSRT | 2 | 29 |
| <u>30R 33R 38E 44D 68Y 70S 75Y 77Q</u><br><u>KRSRES/DYSYQ</u> | <u>30R 32G 44R 68H</u><br><u>KRGYQS/RHRDI</u> | 2 | 30 |
| | <u>30R 32G 44K 68H</u><br><u>KRGYQS/KHRDI</u> | | |
| | <u>30R 32G 44K 68N</u><br><u>KRGYQS/KNRDI</u> | | |
| | <u>30R 32C 44R 68H</u><br><u>KRCYQS/RHRDI</u> | | |
| 32H 33C 40A 44R 68Y 70S 75E 77R<br>KNHCQA/RYSER | 30R 32T 33N 40Q 44I 70S 75N 77R<br>KRTNQQ/IRSNR | 2 | 49 |
| 33R 38D 40R 44K 68Y 70S 75E 77V<br>KNSRDR/KYSEV | 33G 40G 44T 68Y 70S 75Y 77R<br>KNSGQG/TYSYR | 2 | 50 |
| 33N 40R 44K 68Y 70S 75E 77V<br>KNSNQR/KYSEV | 30R 32D 44N 68Y 70S 75Y 77Q<br>KRDYQS/NYSYQ | 3 | 51 |
| 30R 44K 68E 70S 77R<br>KRSYQS/KESDR | 32H 33H 44R 68Y 70S 75E 77Y<br>KNHHQS/RYSEY | 3 | 52 |
| <u>44L 70N 75N 80K</u><br><u>KNSYQS/LRNNI + K80</u> | <u>24V 44N 68Y 70S 75Y 77N</u><br><u>KNSYQS/NYSYN + V24</u> | 4 | 34 |
| 30R 44K 68S 70S 75N 77V<br>KRSYQS/KSSNV | 30S 32T 33S 38R 44A 68Y 70S 75H<br>KSTSRS/AYSDH | 4 | 53 |
| 30S 33C 40A 44N 68K 70H 75N<br>KSSCQA/NKHNI | 32G 33H 68E 70S 75R 77R<br>KNGHQS/QESRR | 5 | 54 |
| 30R 68H 70S 75N 77R<br>KRSYQS/QHSNR | 30T 33G 68Y 70S 75R 77V<br>KTSGQS/QYSRV | 5 | 55 |
| 32R 33D 44E 68C 70S 75N<br>KNRDQS/ECSNI | 33N 38Y 40R 70D 75N 77R<br>KNSNYR/QRDNR | 6 | 56 |
| <u>30S 33H 38K 44I 70S 75N 77R</u><br><u>KSSHKS/IRSNR</u> | <u>32D 38C 44K 68E 70S 77R</u><br><u>KNDYCS/KESDR</u> | 6 | 19 |
| 33H 40R 44N 70S 75R 77Y<br>KNSHQT/NRSRY | 30R 38E 44D 68Y 70S 75S 77R<br>KRSYES/DYSSR | 7 | 57 |

TABLE III-continued

Sequence of heterodimeric I-CreI variants cleaving a
DNA target from the Chinese Hamster GS gene

| First I-CreI variant Sequence (SEQ ID NO: 109, 110, 152 to 155, 114, 156 to 159, 75 160 to 162, 126, 127, 163) | Second I-CreI variant Sequence (SEQ ID NO: 129 to 133, 164 to 167, 137, 168 to 171, 99, 172 to 174, 149, 150, 175) | Target Exon | SEQ ID NO: |
|---|---|---|---|
| 33C 38H 44V 68E 75N 77R 80K KNSCQH/VERNR + K80 | 28S 38R 40K 44N 70S 75R 77Y SNSYRK/NRSRY | 7 | 58 |
| 30D 33R 38T 44Y 70S 77V KDSRTS/YRSDV | 30K 33S 44D 68Y 70S 75S 77R KKSSQS/DYSSR | 7 | 59 |
| 30D 33R 44K 68E 70S 77R KDSRQS/KESDR | 28N 38R 40K 44A 75N NNSYRK/ARRNI | 7 | <u>46</u> |
| <u>33R 38N 40Q 44A 70S 75R 77L</u> KNSRNQ/ARSRL | 30W 33C 44K 68A 70S 77K KWSCQS/KASDK | 7 | <u>47</u> |
| 30G 38K 44A 70S 75E 77R KGSYKS/ARSER | 33R 40R 44A 70G 75N KNSRQR/ARGNI | 7 | 60 |

* the underlined variants can cleave the identical target found in the mouse GS gene.

The sequence of each I-CreI variant is defined by the mutated residues at the indicated positions. For example, the first heterodimeric variant of Table I consists of a first monomer having T, G, V, E, N, R and K at positions 30, 33, 44, 68, 75, 77 and 80, respectively and a second monomer having R, T, N, Q, D, S, R and T at positions 30, 32, 33, 40, 44, 70, 75, and 77 respectively. The positions are indicated by reference to I-CreI sequence (SEQ ID NO: 1); I-CreI has N, S, Y, Q, S, Q, R, R, D, I and E at positions 30, 32, 33, 38, 40, 44, 68, 70, 75, 77 and 80 respectively.

Each monomer (first monomer and second monomer) of the heterodimeric variant according to the present invention may also be named with a letter code, after the eleven residues at positions 28, 30, 32, 33, 38, 40, 44, 68 and 70, 75 and 77 and the additional residues which are mutated, as indicated above. For example, KTSGQS/ENRNR+80K or 28K30T32S33G38Q40S/44E68N70R75N77R +80K stands for I-CreI K28, T30, S32, G33, S38, S40/E44, N68, R70, N75, R77 and K80.

The heterodimeric variant as defined above may have only the amino acid substitutions as indicated above. In this case, the positions which are not indicated are not mutated and thus correspond to the wild-type I-CreI (SEQ ID NO: 1) or I-CreI N75 scaffold (SEQ ID NO: 4) sequence, respectively. Examples of such heterodimeric I-CreI variants cleaving the GS DNA targets of FIGS. 18 to 20 (nucleotide sequences SEQ ID NO: 5 to 60) include the variants consisting of a first and a second monomer corresponding to the following pairs of sequences: SEQ ID NO: 61 to 84 (first monomer) and SEQ ID NO: 85 to 108, respectively (second monomer; FIG. 18 and Table I); SEQ ID NO: 109 to 123, 75, 124 to 128 (first monomer) and SEQ ID NO: 129 to 146, 99, 147 to 151, respectively (second monomer; FIG. 19 and Table II); SEQ ID NO: 109, 110, 152 to 155, 114, 156 to 159, 75, 160 to 162, 126, 127, 163 (first monomer) and SEQ ID NO: 129 to 133, 164 to 167, 137, 168 to 171, 99, 172 to 174, 149, 150 and 175, respectively (second monomer; FIG. 20, Tables III and X).

Alternatively, the heterodimeric variant may consist of an I-CreI sequence comprising the amino acid substitutions as defined above. In the latter case, the positions which are not indicated may comprise additional mutations, for example one or more additional mutations as defined above.

In particular, one or both monomers of the heterodimeric variant comprise advantageously additional substitutions that increase the cleavage activity of the variant for the GS target.

For example, the heterodimeric variants formed by a first variant having any of the sequence SEQ ID NO: 211 to 229, 242 to 244 and 271 (Tables XI and XII) and a second variant having any of the sequence SEQ ID NO: 245 to 268 (Tables XIII and XIV) have additional substitutions that increase the cleavage activity for the GSCHO1 target (SEQ ID NO: 30).

Preferred heterodimeric variants cleaving the GSCHO1 target are presented in Table IV.

TABLE IV

Preferred heterodimeric I-CreI variants for the cleavage of the GSCHO1 target

| Sequence | SEQ ID NO: |
|---|---|
| First I-CreI variant | |
| 30R 33R 38E 44D 66H 68Y 70S 75Y 77Q 132V | 212 |
| 19A 30R 33R 38E 44D 68Y 70S 75Y 77Q 120A | 271 |
| 19S 30R 33R 38E 44D 57E 68Y 70S 75Y 77Q 118T 132V | 215 |
| Second I-CreI variant | |
| 30R 32G 44R 68H | 130 |
| 30R 32G 68A 77R 119L | 246 |
| 30R 33R 68A 77R | 250 |
| 19S 30R 32G 44K 45M 68H | 264 |

* The additional mutations which improve the cleavage activity of the variant against the GSCHO.1 target are in bold The invention encompasses I-CreI variants having at least 85% identity, preferably at least 90% identity, more preferably at least 95% (96%, 97%, 98%, 99%) identity with the sequences as defined above, said variant being able to cleave a DNA target from the GS gene.

The heterodimeric variant is advantageously an obligate heterodimer variant having at least one interesting pair of mutations corresponding to residues of the first and the second monomers which make an intermolecular interaction between the two I-CreI monomers, wherein the first mutation of said pair(s) is in the first monomer and the second mutation of said pair(s) is in the second monomer and said pair(s) of mutations prevent the formation of functional homodimers from each monomer and allow the formation of a functional heterodimer, able to cleave the genomic DNA target from the GS gene.

To form an obligate heterodimer, the monomers have advantageously at least one of the following pairs of mutations, respectively for the first and the second monomer:

a) the substitution of the glutamic acid at position 8 with a basic amino acid, preferably an arginine (first monomer) and the substitution of the lysine at position 7 with an acidic amino acid, preferably a glutamic acid (second monomer); the first monomer may further comprise the substitution of at least one of the lysine residues at positions 7 and 96, by an arginine, b) the substitution of the glutamic acid at position 61 with a basic amino acid, preferably an arginine (first monomer) and the substitution of the lysine at position 96 with an acidic amino acid, preferably a glutamic acid (second monomer); the first monomer may further comprise the substitution of at least one of the lysine residues at positions 7 and 96, by an arginine, c) the substitution of the leucine at position 97 with an aromatic amino acid, preferably a phenylalanine (first monomer) and the substitution of the phenylalanine at position 54 with a small amino acid, preferably a glycine (second monomer); the first monomer may further comprise the substitution of the phenylalanine at position 54 by a tryptophane and the second monomer may further comprise the substitution of the leucine at position 58 or lysine at position 57, by a methionine, and d) the substitution of the aspartic acid at position 137 with a basic amino acid, preferably an arginine (first monomer) and the substitution of the arginine at position 51 with an acidic amino acid, preferably a glutamic acid (second monomer).

For example, the first monomer may have the mutation D137R and the second monomer, the mutation R51D. The obligate heterodimer meganuclease comprises advantageously, at least two pairs of mutations as defined in a), b) c) or d), above; one of the pairs of mutation is advantageously as defined in c) or d). Preferably, one monomer comprises the substitution of the lysine residues at positions 7 and 96 by an acidic amino acid (aspartic acid (D) or glutamic acid (E)), preferably a glutamic acid (K7E and K96E) and the other monomer comprises the substitution of the glutamic acid residues at positions 8 and 61 by a basic amino acid (arginine (R) or lysine (K); for example, E8K and E61R). More preferably, the obligate heterodimer meganuclease, comprises three pairs of mutations as defined in a), b) and c), above. The obligate heterodimer meganuclease consists advantageously of a first monomer (A) having at least the mutations (i) E8R, E8K or E8H, E61R, E61K or E61H and L97F, L97W or L97Y; (ii) K7R, E8R, E61R, K96R and L97F, or (iii) K7R, E8R, F54W, E61R, K96R and L97F and a second monomer (B) having at least the mutations (iv) K7E or K7D, F54G or F54A and K96D or K96E; (v) K7E, F54G, L58M and K96E, or (vi) K7E, F54G, K57M and K96E. For example, the first monomer may have the mutations K7R, E8R or E8K, E61R, K96R and L97F or K7R, E8R or E8K, F54W, E61R, K96R and L97F and the second monomer, the mutations K7E, F54G, L58M and K96E or K7E, F54G, K57M and K96E. The obligate heterodimer may comprise at least one NLS and/or one tag as defined above; said NLS and/or tag may be in the first and/or the second monomer The subject-matter of the present invention is also a single-chain chimeric meganuclease (fusion protein) derived from an I-CreI variant as defined above. The single-chain meganuclease may comprise two I-CreI monomers, two I-CreI core domains (positions 6 to 94 of I-CreI) or a combination of both. Preferably, the two monomers/core domains or the combination of both, are connected by a peptidic linker.

The subject-matter of the present invention is also a polynucleotide fragment encoding a variant or a single-chain chimeric meganuclease as defined above; said polynucleotide may encode one monomer of a homodimeric or heterodimeric variant, or two domains/monomers of a single-chain chimeric meganuclease.

The subject-matter of the present invention is also a recombinant vector for the expression of a variant or a single-chain meganuclease according to the invention. The recombinant vector comprises at least one polynucleotide fragment encoding a variant or a single-chain meganuclease, as defined above. In a preferred embodiment, said vector comprises two different polynucleotide fragments, each encoding one of the monomers of a heterodimeric variant.

A vector which can be used in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those skilled in the art and commercially available.

Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosissarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

Preferred vectors include lentiviral vectors, and particularly self inactivating lentiviral vectors.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, Glutamine Synthetase, and hypoxanthine-guanine phosphoribosyl transferase for eukaryotic cell culture; TRP1, URA3 and LEU2 for *S. cerevisiae*; tetracycline, rifampicin or ampicillin resistance in *E. coli*.

Preferably said vectors are expression vectors, wherein the sequence(s) encoding the variant/single-chain meganuclease of the invention is placed under control of appropriate transcriptional and translational control elements to permit production or synthesis of said variant. Therefore, said polynucleotide is comprised in an expression cassette. More particularly, the vector comprises a replication origin, a promoter operatively linked to said polynucleotide, a ribosome-binding site, an RNA-splicing site (when genomic DNA is used), a polyadenylation site and a transcription termination site. It also can comprise an enhancer. Selection of the promoter will depend upon the cell in which the polypeptide is expressed. Preferably, when said variant is a heterodimer, the two polynucleotides encoding each of the monomers are included in one vector which is able to drive the expression of both polynucleotides, simultaneously. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes.

According to another advantageous embodiment of said vector, it includes a targeting construct comprising sequences sharing homologies with the region surrounding the genomic DNA cleavage site as defined above.

For instance, said sequence sharing homologies with the regions surrounding the genomic DNA cleavage site of the variant is a fragment of the mouse GS gene comprising positions: 2913-3112, 2971-3170, 2999-3198, 3045-3244; 4653-4852, 6360-6559, 6400-6599, 6445-6644, 7083-7282, 7105-7304, 7234-7433, 7266-7465, 7302-7501, 7314-7513, 7316-7515, 7423-7622, 7882-8081, 7906-8105, 7998-8197, 8005-8204 and 8012-8211 of SEQ ID NO: 3. Alternatively, said sequence sharing homologies with the regions surrounding the genomic DNA cleavage site of the variant is a fragment of the human GS gene comprising positions: 2988-3187, 3073-3272, 3075-3274, 3081-3280, 3121-3320, 3127-3326, 4540-4739, 5405-5604, 5425-5624, 5454-5653, 5823-6022, 5936-6135, 5954-6153, 6272-6471, 6341-6540, 6986-7185, 7046-7245, 7055-7254, 7079-7278, 7089-7288, 7136-7335, 7171-7370, 7178-7377 and 7185-7384 of SEQ ID NO: 272.

Alternatively, the vector coding for an I-CreI variant/single-chain meganuclease and the vector comprising the targeting construct are different vectors.

More preferably, the targeting DNA construct comprises:
a) sequences sharing homologies with the region surrounding the genomic DNA cleavage site as defined above, and
b) a sequence to be introduced flanked by sequences as in a) or included in sequences as in a).

Preferably, homologous sequences of at least 50 bp, preferably more than 100 bp and more preferably more than 200 bp are used. Therefore, the targeting DNA construct is preferably from 200 pb to 6000 pb, more preferably from 1000 pb to 2000 pb. Indeed, shared DNA homologies are located in regions flanking upstream and downstream the site of the break and the DNA sequence to be introduced should be located between the two arms. The sequence to be introduced may be any sequence used to alter the chromosomal DNA in some specific way including a sequence used to repair a mutation in the GS gene, restore a functional GS gene in place of a mutated one, modify a specific sequence in the GS gene, to attenuate or activate the GS gene, to inactivate or delete the GS gene or part thereof, to introduce a mutation into a site of interest or to introduce an exogenous gene or part thereof. Such chromosomal DNA alterations are used for genome engineering (animal models/recombinant cell lines) or genome therapy (gene correction or recovery of a functional gene). The targeting construct comprises advantageously a positive selection marker between the two homology arms and eventually a negative selection marker upstream of the first homology arm or downstream of the second homology arm. The marker(s) allow(s) the selection of cells having inserted the sequence of interest by homologous recombination at the target site.

For example FIGS. 18 to 20 indicate the targets from the human, mouse and Chinese Hamster GS genes, examples of variants which are able to cleave said targets and the minimal repair matrix for repairing the cleavage at each target site.

The sequence to be introduced is preferably a sequence for inactivating or deleting the GS gene or part thereof (FIG. 3A). Such chromosomal DNA alterations can be used for making genetically modified cell lines wherein the endogenous GS gene is inactivated and a transgene expression cassette is eventually inserted at the GS gene locus. Such chromosomal DNA alterations can also be used for making knock-out and knock-in cell/animals wherein the GS gene is inactivated (knock-out) and eventually replaced with an exogenous gene of interest (knock-in).

Following inactivation of the endogenous GS gene, Glutamine Synthetase may be used as a positive selection marker in further genome engineering strategies (targeted or random gene manipulation) at any locus of the genome of the GS deficient cell/animal.

For making knock-in cells/animals, the targeting DNA construct comprises a GS gene fragment which has at least 200 bp of homologous sequence flanking the target site of the I-CreI variant for repairing the cleavage, the sequence of an exogenous gene of interest included in an expression cassette and eventually a selection marker such as the neomycin resistance gene.

For the insertion of a sequence, DNA homologies are generally located in regions directly upstream and downstream to the site of the break (sequences immediately adjacent to the break; minimal repair matrix). However, when the insertion is associated with a deletion of ORF sequences flanking the cleavage site, shared DNA homologies are located in regions upstream and downstream the region of the deletion.

Alternatively, the sequence to be introduced is a sequence which repairs a mutation in the GS gene (gene correction or recovery of a functional gene), for the purpose of genome therapy (FIGS. 3C and 3D). For correcting the GS gene, cleavage of the gene occurs in the vicinity of the mutation, preferably, within 500 bp of the mutation (FIG. 3C). The targeting construct comprises a GS gene fragment which has at least 200 bp of homologous sequence flanking the target site (minimal repair matrix) for repairing the cleavage, and includes a sequence encoding a portion of wild-type GS gene corresponding to the region of the mutation for repairing the mutation (FIG. 3C). Consequently, the targeting construct for gene correction comprises or consists of the minimal repair matrix; it is preferably from 200 pb to 6000 pb, more preferably from 1000 pb to 2000 pb. Preferably, when the cleavage site of the variant overlaps with the mutation the repair matrix includes a modified cleavage site that is not cleaved by the variant which is used to induce said cleavage in the GS gene and a sequence encoding wild-type GS that does not change the open reading frame of the GS gene.

Alternatively, for restoring a functional gene (FIG. 3D), cleavage of the gene occurs upstream of a mutation. Preferably said mutation is the first known mutation in the sequence of the gene, so that all the downstream mutations of the gene can be corrected simultaneously. The targeting construct comprises the exons downstream of the cleavage site fused in frame (as in the cDNA) and with a polyadenylation site to stop transcription in 3'. The sequence to be introduced (exon knock-in construct) is flanked by introns or exons sequences surrounding the cleavage site, so as to allow the transcription of the engineered gene (exon knock-in gene) into a mRNA able to code for a functional protein (FIG. 3D). For example, the exon knock-in construct is flanked by sequences upstream and downstream of the cleavage site, from a minimal repair matrix as defined above.

The subject matter of the present invention is also a targeting DNA construct as defined above.

The subject-matter of the present invention is also a composition characterized in that it comprises at least one meganuclease as defined above (variant or single-chain chimeric meganuclease) and/or at least one expression vector encoding said meganuclease, as defined above.

In a preferred embodiment of said composition, it comprises a targeting DNA construct, as defined above.

Preferably, said targeting DNA construct is either included in a recombinant vector or it is included in an expression vector comprising the polynucleotide(s) encoding the meganuclease according to the invention.

The subject-matter of the present invention is further the use of a meganuclease as defined above, one or two polynucleotide(s), preferably included in expression vector(s), for genome engineering of the GS gene for non-therapeutic purposes. The GS gene may be the endogenous GS gene at its genomic locus or a transgene that has been inserted in an animal or a cell line, for example a GS knock-in animal or cell line.

According to an advantageous embodiment of said use, it is for inducing a double-strand break in a site of interest of the GS gene comprising a genomic DNA target sequence, thereby inducing a DNA recombination event, a DNA loss or cell death.

According to the invention, said double-strand break is for: repairing a specific sequence in the GS gene, modifying a specific sequence in the GS gene, restoring a functional GS gene in place of a mutated one, attenuating or activating the GS gene, introducing a mutation into a site of interest of the GS gene, introducing an exogenous gene or a part thereof, inactivating or deleting the GS gene or a part thereof, translocating a chromosomal arm, or leaving the DNA unrepaired and degraded.

Preferably it is for: (i) inactivating the GS gene by homologous recombination with an inactivation cassette (knock-out animal/cell line (FIG. 3A)) and eventually inserting a transgene expression cassette at the GS gene locus (knock-in animal/cell line (FIG. 3A) or (ii) inactivating the GS gene by non-homologous end joining (FIG. 3B)).

The subject-matter of the present invention is also a method for making a GS knock-out or knock-in recombinant cell, comprising at least the step of:

(a) introducing into a cell, a meganuclease as defined above (I-CreI variant or single-chain derivative), so as to into induce a double stranded cleavage at a site of interest of the GS gene comprising a DNA recognition and cleavage site for said meganuclease, simultaneously or consecutively, (b) introducing into the cell of step (a), a targeting DNA, wherein said targeting DNA comprises (1) DNA sharing homologies to the region surrounding the cleavage site and (2) DNA which repairs the site of interest upon recombination between the targeting DNA and the chromosomal DNA, so as to generate a recombinant cell having repaired the site of interest by homologous recombination, (c) isolating the recombinant cell of step (b), by any appropriate means.

The subject-matter of the present invention is also a method for making a GS knock-out or knock-in animal, comprising at least the step of:

(a) introducing into a pluripotent precursor cell or an embryo of an animal, a meganuclease as defined above, so as to induce a double stranded cleavage at a site of interest of the GS gene comprising a DNA recognition and cleavage site for said meganuclease, simultaneously or consecutively, (b) introducing into the animal precursor cell or embryo of step (a) a targeting DNA, wherein said targeting DNA comprises (1) DNA sharing homologies to the region surrounding the cleavage site and (2) DNA which repairs the site of interest upon recombination between the targeting DNA and the chromosomal DNA, so as to generate a genomically modified animal precursor cell or embryo having repaired the site of interest by homologous recombination, (c) developing the genomically modified animal precursor cell or embryo of step (b) into a chimeric animal, and (d) deriving a transgenic animal from the chimeric animal of step (c).

Preferably, step (c) comprises the introduction of the genomically modified precursor cell generated in step (b) into blastocysts so as to generate chimeric animals.

The targeting DNA is introduced into the cell under conditions appropriate for introduction of the targeting DNA into the site of interest.

For making knock-out cells/animals, the DNA which repairs the site of interest comprises sequences that inactivate the GS gene.

For making knock-in cells/animals, the DNA which repairs the site of interest comprises the sequence of an exogenous gene of interest, and eventually a selection marker, such as the neomycin resistance gene.

In a preferred embodiment, said targeting DNA construct is inserted in a vector.

Alternatively, the GS gene may be inactivated by repair of the double-strand break by non-homologous end joining (FIG. 3B).

The subject-matter of the present invention is also a method for making a GS-deficient cell, comprising at least the step of:

(a) introducing into a cell, a meganuclease as defined above, so as to induce a double stranded cleavage at a site of interest of the GS gene comprising a DNA recognition and cleavage site of said meganuclease, and thereby generate genomically modified GS deficient cell having repaired the double-strands break, by non-homologous end joining, and (b) isolating the genomically modified GS deficient cell of step (a), by any appropriate mean.

The subject-matter of the present invention is also a method for making a GS knock-out animal, comprising at least the step of:

(a) introducing into a pluripotent precursor cell or an embryo of an animal, a meganuclease, as defined above, so as to induce a double stranded cleavage at a site of interest of the GS gene comprising a DNA recognition and cleavage site of said meganuclease, and thereby generate genomically modified precursor cell or embryo having repaired the double-strands break by non-homologous end joining, (b) developing the genomically modified animal precursor cell or embryo of step (a) into a chimeric animal, and (c) deriving a transgenic animal from a chimeric animal of step (b).

Preferably, step (b) comprises the introduction of the genomically modified precursor cell obtained in step (a), into blastocysts, so as to generate chimeric animals.

The cells which are modified may be any cells of interest. For making knock-in/transgenic mice, the cells are pluripotent precursor cells such as embryo-derived stem (ES) cells, which are well-known in the art. For making recombinant human cell lines, the cells may advantageously be PerC6 (Fallaux et al., Hum. Gene Ther. 9, 1909-1917, 1998) or HEK293 (ATCC # CRL-1573) cells. For making mouse cell lines, the cells may advantageously be NSO, SP2/0 (BALB/c myeloma; ECACC #85110503 and #85072401), or L (ATCC #CRL-2648) cells. For making Chinese Hamster cell lines, the cells may advantageously be CHO-K1 (ATCC #CCL-61, DG44 (Invitrogen), or CHO-S (Invitrogen) cells.

The animal is preferably a mammal, more preferably a laboratory rodent (mice, rat, guinea-pig), or a cow, pig, horse or goat.

Said meganuclease can be provided directly to the cell or through an expression vector comprising the polynucleotide sequence encoding said meganuclease and suitable for its expression in the used cell.

For making recombinant cell lines expressing an heterologous protein of interest, the targeting DNA comprises a sequence encoding the product of interest (protein or RNA), and eventually a marker gene, flanked by sequences upstream and downstream the cleavage site, as defined above, so as to generate genomically modified cells having integrated the exogenous sequence of interest in the GS gene, by homologous recombination.

The sequence of interest may be any gene coding for a certain protein/peptide of interest, included but not limited to: reporter genes, receptors, signaling molecules, transcription factors, pharmaceutically active proteins and peptides, disease causing gene products and toxins. The sequence may also encode an RNA molecule of interest including for example a siRNA.

The expression of the exogenous sequence may be driven, either by the endogenous GS gene promoter or by a heterologous promoter, preferably a ubiquitous or tissue specific promoter, either constitutive or inducible, as defined above. In addition, the expression of the sequence of interest may be conditional; the expression may be induced by a site-specific recombinase (Cre, FLP . . . ).

Thus, the sequence of interest is inserted in an appropriate cassette that may comprise an heterologous promoter operatively linked to said gene of interest and one or more functional sequences including but not limited to (selectable) marker genes, recombinase recognition sites, polyadenylation signals, splice acceptor sequences, introns, tags for protein detection and enhancers.

The subject matter of the present invention is also a kit for making GS knock-out or knock-in cells/animals comprising at least a meganuclease and/or one expression vector, as defined above. Preferably, the kit further comprises a targeting DNA comprising a sequence that inactivates the GS gene flanked by sequences sharing homologies with the region of the GS gene surrounding the DNA cleavage site of said meganuclease. In addition, for making knock-in cells/animals, the kit includes also a vector comprising a sequence of interest to be introduced in the genome of said cells/animals and eventually a selectable marker gene, as defined above.

The subject-matter of the present invention is also the use of at least one meganuclease and/or one expression vector, as defined above, for the preparation of a medicament for preventing, improving or curing a pathological condition caused by a mutation in the GS gene as defined above, in an individual in need thereof.

Preferably said pathological condition is inherited systemic deficiency of glutamine.

The use of the meganuclease may comprise at least the step of (a) inducing in somatic tissue(s) of the donor/individual a double stranded cleavage at a site of interest of the GS gene comprising at least one recognition and cleavage site of said meganuclease by contacting said cleavage site with said meganuclease, and (b) introducing into said somatic tissue(s) a targeting DNA, wherein said targeting DNA comprises (1) DNA sharing homologies to the region surrounding the cleavage site and (2) DNA which repairs the GS gene upon recombination between the targeting DNA and the chromosomal DNA, as defined above. The targeting DNA is introduced into the somatic tissues(s) under conditions appropriate for introduction of the targeting DNA into the site of interest.

According to the present invention, said double-stranded cleavage may be induced, ex vivo by introduction of said meganuclease into somatic cells from the diseased individual and then transplantation of the modified cells back into the diseased individual.

The subject-matter of the present invention is also a method for preventing, improving or curing a pathological condition caused by a mutation in the GS gene, in an individual in need thereof, said method comprising at least the step of administering to said individual a composition as defined above, by any means. The meganuclease can be used either as a polypeptide or as a polynucleotide construct encoding said polypeptide. It is introduced into mouse cells, by any convenient means well-known to those in the art, which are appropriate for the particular cell type, alone or in association with either at least an appropriate vehicle or carrier and/or with the targeting DNA.

According to an advantageous embodiment of the uses according to the invention, the meganuclease (polypeptide) is associated with:

liposomes, polyethyleneimine (PEI); in such a case said association is administered and therefore introduced into somatic target cells.

membrane translocating peptides (Bonetta, The Scientist, 2002, 16, 38; Ford et al., Gene Ther., 2001, 8, 1-4; Wadia and Dowdy, Curr. Opin. Biotechnol., 2002, 13, 52-56); in such a case, the sequence of the variant/single-chain meganuclease is fused with the sequence of a membrane translocating peptide (fusion protein).

According to another advantageous embodiment of the uses according to the invention, the meganuclease (polynucleotide encoding said meganuclease) and/or the targeting DNA is inserted in a vector. Vectors comprising targeting DNA and/or nucleic acid encoding a meganuclease can be introduced into a cell by a variety of methods (e.g., injection, direct uptake, projectile bombardment, liposomes, electroporation). Meganucleases can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). Optionally, it may be preferable to incorporate a nuclear localization signal into the recombinant protein to be sure that it is expressed within the nucleus.

Once in a cell, the meganuclease and if present, the vector comprising targeting DNA and/or nucleic acid encoding a meganuclease are imported or translocated by the cell from the cytoplasm to the site of action in the nucleus.

For purposes of therapy, the meganucleases and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results in a decrease in the severity of one or more symptoms of the targeted disease and in a genome correction of the lesion or abnormality.

In one embodiment of the uses according to the present invention, the meganuclease is substantially non-immunogenic, i.e., engender little or no adverse immunological response. A variety of methods for ameliorating or eliminating deleterious immunological reactions of this sort can be used in accordance with the invention. In a preferred embodiment, the meganuclease is substantially free of N-formyl methionine. Another way to avoid unwanted immunological reactions is to conjugate meganucleases to polyethylene glycol ("PEG") or polypropylene glycol ("PPG") (preferably of 500 to 20,000 daltons average molecular weight (MW)). Conjugation with PEG or PPG, as described by Davis et al. (U.S. Pat. No. 4,179,337) for example, can provide non-immunogenic, physiologically active, water soluble endonuclease conjugates with anti-viral activity. Similar methods also using a polyethylene-poly-propylene glycol copolymer are described in Saifer et al. (U.S. Pat. No. 5,006,333).

The invention also concerns a prokaryotic or eukaryotic host cell which is modified by a polynucleotide or a vector as defined above, preferably an expression vector.

The invention also concerns a non-human transgenic animal or a transgenic plant, characterized in that all or a part of their cells are modified by a polynucleotide or a vector as defined above.

As used herein, a cell refers to a prokaryotic cell, such as a bacterial cell, or an eukaryotic cell, such as an animal, plant or yeast cell.

The subject-matter of the present invention is also the use of at least one meganuclease variant, as defined above, as a scaffold for making other meganucleases. For example, further rounds of mutagenesis and selection/screening can be performed on said variants, for the purpose of making novel meganucleases.

The different uses of the meganuclease and the methods of using said meganuclease according to the present invention include the use of the I-CreI variant, the single-chain chimeric meganuclease derived from said variant, the polynucleotide(s), vector, cell, transgenic plant or non-human transgenic mammal encoding said variant or single-chain chimeric meganuclease, as defined above.

The I-CreI variant according to the invention may be obtained by a method for engineering I-CreI variants able to cleave a genomic DNA target sequence from the GS gene, comprising at least the steps of:

(a) constructing a first series of I-CreI variants having at least one substitution in a first functional subdomain of the LAGLIDADG core domain situated from positions 28 to 40 of I-CreI, (b) constructing a second series of I-CreI variants having at least one substitution in a second functional subdomain of the LAGLIDADG core domain situated from positions 44 to 77 of I-CreI, (c) selecting and/or screening the variants from the first series of step (a) which are able to cleave a mutant I-CreI site wherein (i) the nucleotide triplet at positions −10 to −8 of the I-CreI site has been replaced with the nucleotide triplet which is present at positions −10 to −8 of said genomic target and (ii) the nucleotide triplet at positions +8 to +10 has been replaced with the reverse complementary sequence of the nucleotide triplet which is present at positions −10 to −8 of said genomic target, (d) selecting and/or screening the variants from the second series of step (b) which are able to cleave a mutant I-CreI site wherein (i) the nucleotide triplet at positions −5 to −3 of the I-CreI site has been replaced with the nucleotide triplet which is present at positions −5 to −3 of said genomic target and (ii) the nucleotide triplet at positions +3 to +5 has been replaced with the reverse complementary sequence of the nucleotide triplet which is present at positions −5 to −3 of said genomic target, (e) selecting and/or screening the variants from the first series of step (a) which are able to cleave a mutant I-CreI site wherein (i) the nucleotide triplet at positions +8 to +10 of the I-CreI site has been replaced with the nucleotide triplet which is present at positions +8 to +10 of said genomic target and (ii) the nucleotide triplet at positions −10 to −8 has been replaced with the reverse complementary sequence of the nucleotide triplet which is present at positions +8 to +10 of said genomic target, (f) selecting and/or screening the variants from the second series of step (b) which are able to cleave a mutant I-CreI site wherein (i) the nucleotide triplet at positions +3 to +5 of the I-CreI site has been replaced with the nucleotide triplet which is present at positions +3 to +5 of said genomic target and (ii) the nucleotide triplet at positions −5 to −3 has been replaced with the reverse complementary sequence of the nucleotide triplet which is present at positions +3 to +5 of said genomic target, (g) combining in a single variant, the mutation(s) at positions 28 to 40 and 44 to 77 of two variants from step (c) and step (d), to obtain a novel homodimeric I-CreI variant which cleaves a sequence wherein (i) the nucleotide triplet at positions −10 to −8 is identical to the nucleotide triplet which is present at positions −10 to −8 of said genomic target, (ii) the nucleotide triplet at positions +8 to +10 is identical to the reverse complementary sequence of the nucleotide triplet which is present at positions −10 to −8 of said genomic target, (iii) the nucleotide triplet at positions −5 to −3 is identical to the nucleotide triplet which is present at positions −5 to −3 of said genomic target and (iv) the nucleotide triplet at positions +3 to +5 is identical to the reverse complementary sequence of the nucleotide triplet which is present at positions −5 to −3 of said genomic target, and/or (h) combining in a single variant, the mutation(s) at positions 28 to 40 and 44 to 77 of two variants from step (e) and step (f), to obtain a novel homodimeric I-CreI variant which cleaves a sequence wherein (i) the nucleotide triplet at positions +3 to +5 is identical to the nucleotide triplet which is present at positions +3 to +5 of said genomic target, (ii) the nucleotide triplet at positions −5 to −3 is identical to the reverse complementary sequence of the nucleotide triplet which is present at positions +3 to +5 of said genomic target, (iii) the nucleotide triplet at positions +8 to +10 of the I-CreI site has been replaced with the nucleotide triplet which is present at positions +8 to +10 of said genomic target and (iv) the nucleotide triplet at positions −10 to −8 is identical to the reverse complementary sequence of the nucleotide triplet at positions +8 to +10 of said genomic target, (i) combining the variants obtained in steps (g) and (h) to form heterodimers, and (j) selecting and/or screening the heterodimers from step (i) which are able to cleave said genomic DNA target from the GS gene.

One of the step(s) (c), (d), (e) or (f) may be omitted. For example, if step (c) is omitted, step (d) is performed with a mutant I-CreI site wherein both nucleotide triplets at positions −10 to −8 and −5 to −3 have been replaced with the nucleotide triplets which are present at positions −10 to −8 and −5 to −3, respectively of said genomic target, and the nucleotide triplets at positions +3 to +5 and +8 to +10 have been replaced with the reverse complementary sequence of the nucleotide triplets which are present at positions −5 to −3 and −10 to −8, respectively of said genomic target.

The (intramolecular) combination of mutations in steps (g) and (h) may be performed by amplifying overlapping fragments comprising each of the two subdomains, according to well-known overlapping PCR techniques.

The (intermolecular) combination of the variants in step (i) is performed by co-expressing one variant from step (g) with one variant from step (h), so as to allow the formation of heterodimers. For example, host cells may be modified by one or two recombinant expression vector(s) encoding said variant(s). The cells are then cultured under conditions allowing the expression of the variant(s), so that heterodimers are formed in the host cells, as described previously in the International PCT Application WO 2006/097854 and Arnould et al., J. Mol. Biol., 2006, 355, 443-458.

The selection and/or screening in steps (c), (d), (e), (f) and/or (j) may be performed by using a cleavage assay in vitro or in vivo, as described in the International PCT Application WO 2004/067736, Arnould et al., J. Mol. Biol., 2006, 355, 443-458, Epinat et al., Nucleic Acids Res., 2003, 31, 2952-2962 and Chames et al., Nucleic Acids Res., 2005, 33, e178.

According to another advantageous embodiment of said method, steps (c), (d), (e), (f) and/or (j) are performed in vivo, under conditions where the double-strand break in the mutated DNA target sequence which is generated by said variant leads to the activation of a positive selection marker or a reporter gene, or the inactivation of a negative selection marker or a reporter gene, by recombination-mediated repair of said DNA double-strand break.

Furthermore, the homodimeric combined variants obtained in step (g) or (h) are advantageously submitted to a selection/screening step to identify those which are able to cleave a pseudo-palindromic sequence wherein at least the nucleotides at positions −11 to −3 (combined variant of step (g)) or +3 to +11 (combined variant of step (h)) are identical to the nucleotides which are present at positions −11 to −3 (combined variant of step (g)) or +3 to +11 (combined variant of step (h)) of said genomic target, and the nucleotides at positions +3 to +11 (combined variant of step (g)) or −11 to −3 (combined variant of step (h)) are identical to the reverse complementary sequence of the nucleotides which are present at positions −11 to −3 (combined variant of step (g)) or +3 to +11 (combined variant of step (h)) of said genomic target.

Preferably, the set of combined variants of step (g) or step (h) (or both sets) undergoes an additional selection/screening step to identify the variants which are able to cleave a pseudo-palindromic sequence wherein: (i) the nucleotides at positions −2 to +2 (four central bases) are identical to the nucleotides which are present at positions −2 to +2 of said genomic target, (ii) the nucleotides at positions −11 to −3 (combined variant of step g)) or +3 to +11 (combined variant of step (h)) are identical to the nucleotides which are present at positions −11 to −3 (combined variant of step (g)) or +3 to +11 (combined variant of step h)) of said genomic target, and (iii) the nucleotides at positions +3 to +11 (combined variant of step (g)) or −11 to −3 (combined variant of step (h)) are identical to the reverse complementary sequence of the nucleotides which are present at positions −11 to −3 (combined variant of step (g)) or +3 to +11 (combined variant of step (h)) of said genomic target. This additional screening step increases the probability of isolating heterodimers which are able to cleave the genomic target of interest (step (j)).

Steps (a), (b), (g), (h) and (i) may further comprise the introduction of additional mutations at other positions contacting the DNA target sequence or interacting directly or indirectly with said DNA target, at positions which improve the binding and/or cleavage properties of the variants, or at positions which either prevent or impair the formation of functional homodimers or favor the formation of the heterodimer, as defined above.

The additional mutations may be introduced by site-directed mutagenesis and/or random mutagenesis on a variant or on a pool of variants, according to standard mutagenesis methods which are well-known in the art, for example by using PCR.

In particular, random mutations may be introduced on the whole variant or in a part of the variant, in particular the C-terminal half of the variant (positions 80 to 163) to improve the binding and/or cleavage properties of the variants towards the DNA target from the gene of interest. Site-directed mutagenesis at positions which improve the binding and/or cleavage properties of the variants, for example at positions 19, 54, 80, 87, 105 and for 132, may also be combined with random-mutagenesis. The mutagenesis may be performed by generating random/site-directed mutagenesis libraries on a pool of variants, according to standard mutagenesis methods which are well-known in the art. Site-directed mutagenesis may be advantageously performed by amplifying overlapping fragments comprising the mutated position(s), as defined above, according to well-known overlapping PCR techniques. In addition, multiple site-directed mutagenesis, may advantageously be performed on a variant or on a pool of variants.

Preferably, the mutagenesis is performed on one monomer of the heterodimer formed in step (i) or obtained in step (j), advantageously on a pool of monomers, preferably on both monomers of the heterodimer of step (i) or (j).

Preferably, at least two rounds of selection/screening are performed according to the process illustrated by FIG. 4 of Arnould et al., J. Mol. Biol., 2007, 371, 49-65. In the first round, one of the monomers of the heterodimer is mutagenised (monomer Y in FIG. 4), co-expressed with the other monomer (monomer X in FIG. 4) to form heterodimers, and the improved monomers $Y^+$ are selected against the target from the gene of interest. In the second round, the other monomer (monomer X) is mutagenised, co-expressed with the improved monomers $Y^+$ to form heterodimers, and selected against the target from the gene of interest to obtain meganucleases $(X^+Y^+)$ with improved activity. The mutagenesis may be random-mutagenesis or site-directed mutagenesis on a monomer or on a pool of monomers, as indicated above. Both types of mutagenesis are advantageously combined. Additional rounds of selection/screening on one or both monomers may be performed to improve the cleavage activity of the variant.

The cleavage activity of the improved meganuclease obtainable by the method according to the present invention may be measured by a direct repeat recombination assay, in yeast or mammalian cells, using a reporter vector, by comparison with that of the initial meganuclease. The reporter vector comprises two truncated, non-functional copies of a reporter gene (direct repeats) and the genomic DNA target sequence which is cleaved by the initial meganuclease, within the intervening sequence, cloned in a yeast or a mammalian expression vector. Expression of the meganuclease results in cleavage of the genomic DNA target sequence. This cleavage induces homologous recombination between the direct repeats, resulting in a functional reporter gene (LacZ, for example), whose expression can be monitored by appropriate assay. A stronger signal is observed with the improved meganuclease, as compared to the initial meganuclease. Alternatively, the activity of the improved meganuclease towards its genomic DNA target can be compared to that of I-CreI towards the I-CreI site, at the same genomic locus, using a chromosomal assay in mammalian cells (Arnould et al., J. Mol. Biol., 2007, 371, 49-65).

The subject matter of the present invention is also an I-CreI variant having mutations at positions 28 to 40 and/or 44 to 77 of I-CreI that is useful for engineering the variants able to cleave a DNA target from the GS gene, according to the present invention. In particular, the invention encompasses the I-CreI variants as defined in step (c) to (f) of the method for engineering I-CreI variants, as defined above, including the variants at positions 28, 30, 32, 33, 38 and 40, or 44, 68, 70, 75 and 77 presented in Tables V and VII. The invention encompasses also the I-CreI variants as defined in step (g) and (h) of the method for engineering I-CreI variants, as defined above including the combined variants of Table V to VIII.

Single-chain chimeric meganucleases able to cleave a DNA target from the gene of interest are derived from the variants according to the invention by methods well-known in the art (Epinat et al., Nucleic Acids Res., 2003, 31, 2952-62; Chevalier et al., Mol. Cell., 2002, 10, 895-905; Steuer et al., Chembiochem., 2004, 5, 206-13; International PCT Applications WO 03/078619 and WO 2004/031346). Any of such methods, may be applied for constructing single-chain chimeric meganucleases derived from the variants as defined in the present invention.

The polynucleotide sequence(s) encoding the variant as defined in the present invention may be prepared by any method known by the man skilled in the art. For example, they are amplified from a cDNA template, by polymerase chain reaction with specific primers. Preferably the codons of said cDNA are chosen to favour the expression of said protein in the desired expression system.

The recombinant vector comprising said polynucleotides may be obtained and introduced in a host cell by the well-known recombinant DNA and genetic engineering techniques.

The I-CreI variant or single-chain derivative as defined in the present invention are produced by expressing the polypeptide(s) as defined above; preferably said polypeptide(s) are expressed or co-expressed (in the case of the variant only) in a host cell or a transgenic animal/plant modified by one expression vector or two expression vectors (in the case of the variant only), under conditions suitable for the expression or co-expression of the polypeptide(s), and the variant or single-chain derivative is recovered from the host cell culture or from the transgenic animal/plant.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In addition to the preceding features, the invention further comprises other features which will emerge from the description which follows, which refers to examples illustrating the I-CreI meganuclease variants and their uses according to the invention, as well as to the appended drawings in which:

FIG. 1: Modular structure of homing endonucleases and the combinatorial approach for custom meganucleases design. A. Tridimensional structure of the I-CreI homing endonuclease bound to its DNA target. The catalytic core is surrounded by two αββαββα a folds forming a saddle-shaped interaction interface above the DNA major groove. B. Different I-CreI variants binding different sequences derived from the I-CreI target sequence (top right and bottom left) to obtain heterodimers or single chain fusion molecules cleaving non palindromic chimeric targets (bottom right). C. The identification of smaller independent subunit, i.e., subunit within a single monomer or αββαββα fold (top right and bottom left) would allow for the design of novel chimeric molecules (bottom right), by combination of mutations within a same monomer. Such molecules would cleave palindromic chimeric targets (bottom right). D. The combination of the two former steps would allow a larger combinatorial approach, involving four different subdomains. In a first step, couples of novel meganucleases could be combined in new molecules ("half-meganucleases") cleaving palindromic targets derived from the target one wants to cleave. Then, the combination of such "half-meganuclease" can result in a heterodimeric species cleaving the target of interest. Thus, the identification of a small number of new cleavers for each subdomain would allow for the design of a very large number of novel endonucleases.

FIG. 2: Glutamine Synthetase coding sequence. A. The mouse Glutamine Synthetase gene (accession number NC000067.5). Exons are indicated as grey boxes. The GSCHO1 target is indicated with its sequence and position. B. The *Criteculus griseus* Glutamine Synthetase mRNA (accession number X03495). The ORF is indicated as a grey box. The GSCHO1 genomic target site is indicated with its sequence and its position relative to the Glutamine Synthetase mRNA sequence.

FIG. 3: Strategies for the utilization of a meganuclease cleaving the Glutamine Synthetase (GS) gene. A. Gene insertion and/or gene inactivation. Upon cleavage by a meganuclease and recombination with a repair matrix containing a gene of interest (gene insertion) or an inactivation cassette (gene inactivation), flanked by sequences sharing homology with the sequences surrounding the cleavage site, gene insertion or gene inactivation occurs. B. Gene inactivation by Non-Homologous End-Joining. Upon cleavage by a meganuclease, the DNA ends are degraded and rejoined by Non-Homologous-End-Joining (NHEJ), and gene inactivation occurs. C. Gene Correction. A mutation occurs within the GS gene. Upon cleavage by a meganuclease and recombination with a repair matrix the deleterious mutation is corrected. D. Exonic sequences knock-in. A mutation occurs within the GS gene. The mutated mRNA transcript is featured below the gene. In the repair matrix, exons located downstream of the cleavage site are fused in-frame (as in a cDNA), with a poly-adenylation site to stop transcription at the 3' end. Intronic and exonic sequences can be used as homologous regions. A knock-in of exonic sequences results in an engineered gene, transcribed into a mRNA able to code for a functional protein.

FIG. 4: The GSCHO1 target sequences and its derivatives. 10GCC_P, 10GGA_P, 5AGG_P and 5TTC_P are close derivatives cleaved by previously obtained I-CreI variants. They differ from C1221 by the boxed motives. C1221, 10GCC_P, 10GGA_P, 5AGG_P and 5TTC_P were first described as 24 bp sequences, but structural data suggest that only the 22 bp are relevant for protein/DNA interaction. However, positions ±12 are indicated in parenthesis. GSCHO1 is the DNA sequence located in the mouse and *Criteculus griseus* Glutamine Synthetase gene. In the GSCHO1.2 target, the GTGA sequence in the middle of the target is replaced with GTAC, the bases found in C1221. GSCHO1.3 is the palindromic sequence derived from the left part of GSCHO1.2, and GSCHO1.4 is the palindromic sequence derived from the right part of GSCHO1.2. As shown in the Figure, the boxed motives from 10GCC_P, 10GGA_P, 5AGG_P and 5TTC_P are found in the GSCHO1 series of targets.

Figure 5:
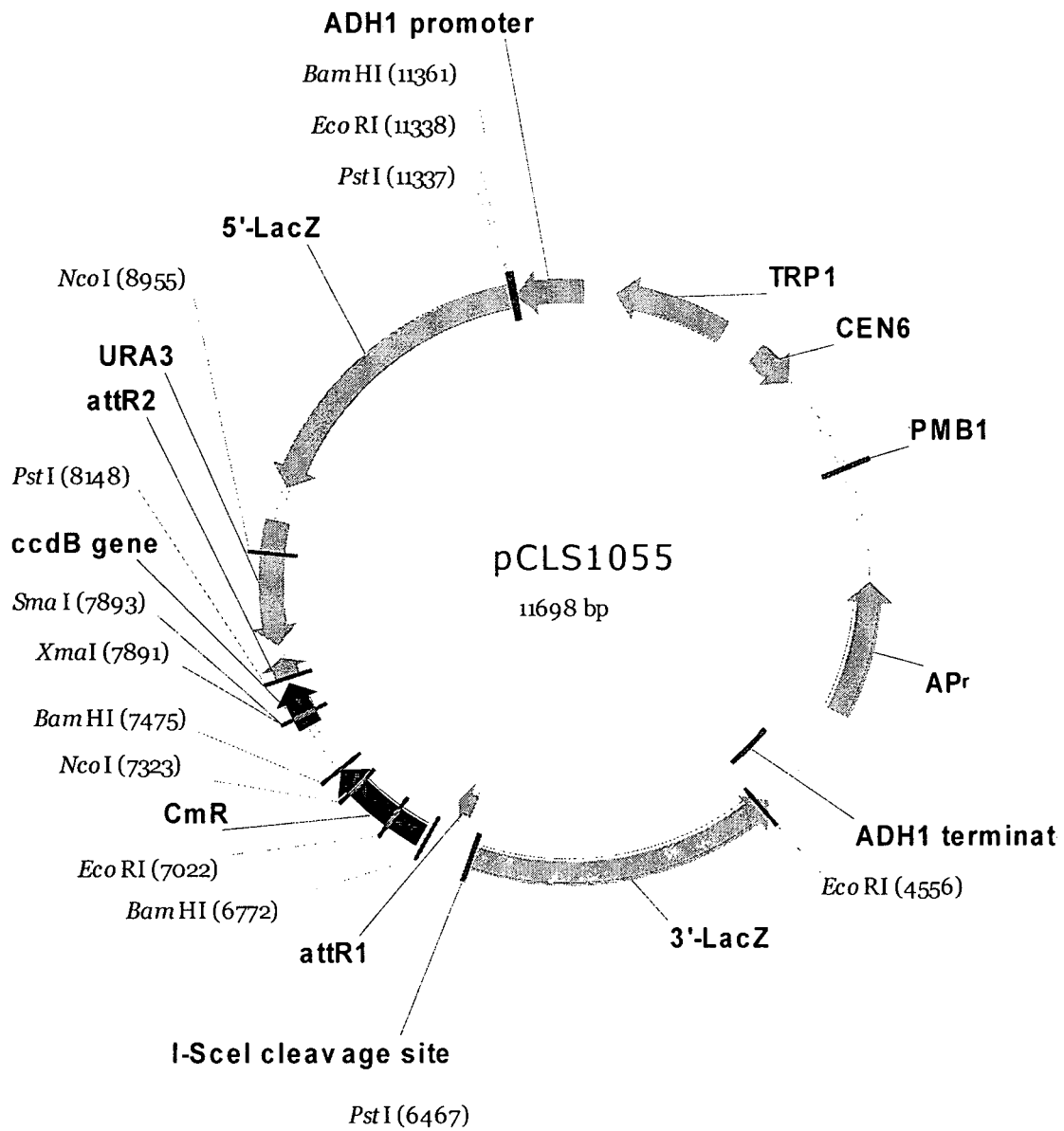

FIG. 5: pCLS1055 plasmid map.

Figure 6:
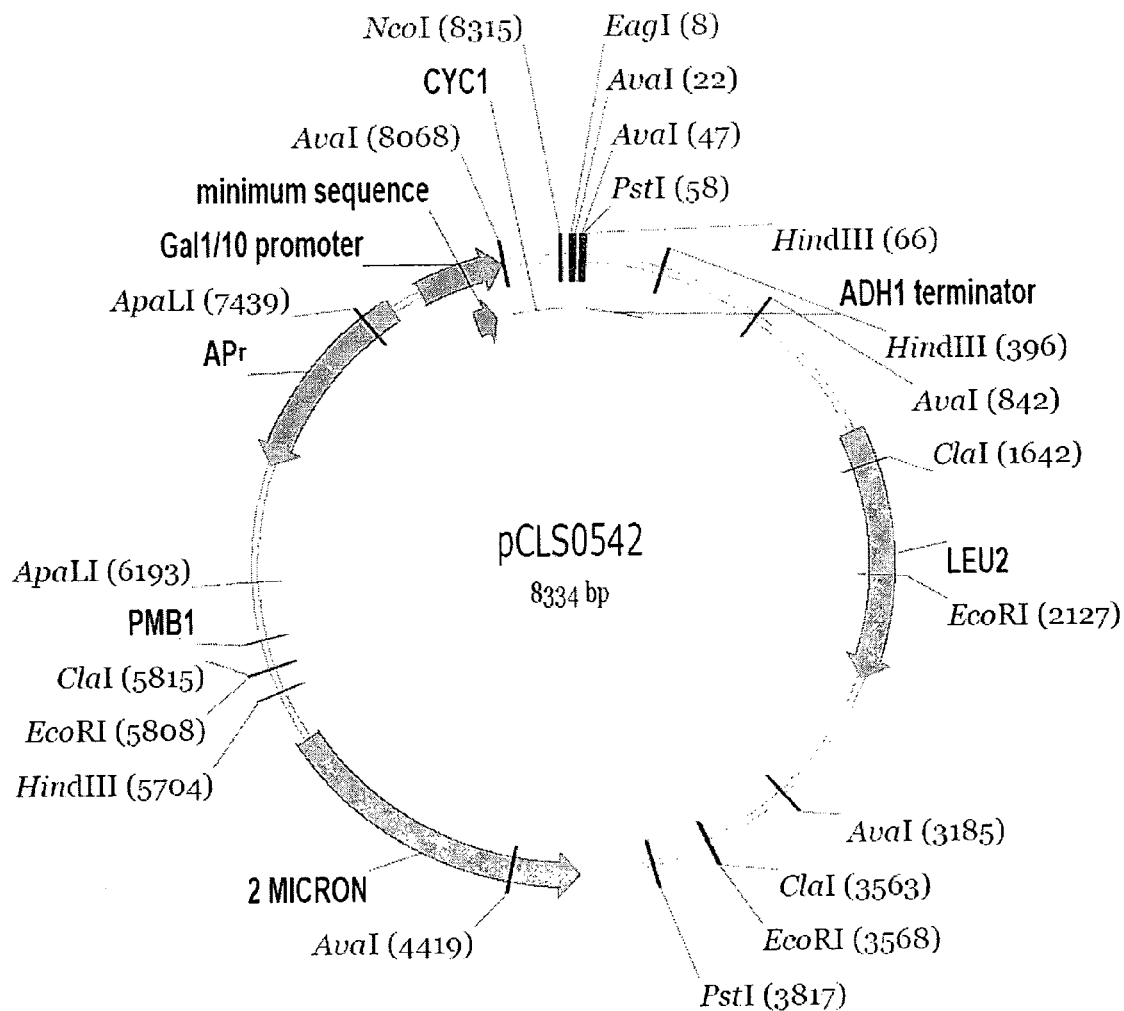

FIG. 6: pCLS0542 plasmid map.

Figure 7:
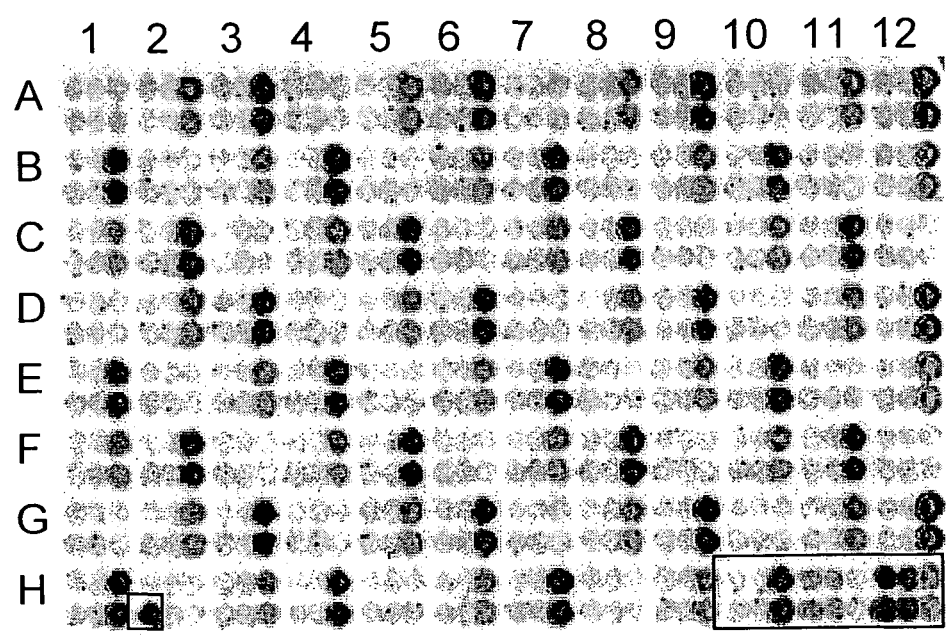

FIG. 7: Cleavage of GSCHO1.3 target by combinatorial variants. The figure displays an example of screening of I-CreI combinatorial variants with the GSCHO1.3 target. On the filter, the sequence of the positive variant at position H2 is KRSRES/DYSYQ (according to the nomenclature of Table VI). H10, H11, H12 are negative and positive controls of different strength.

Figure 8:
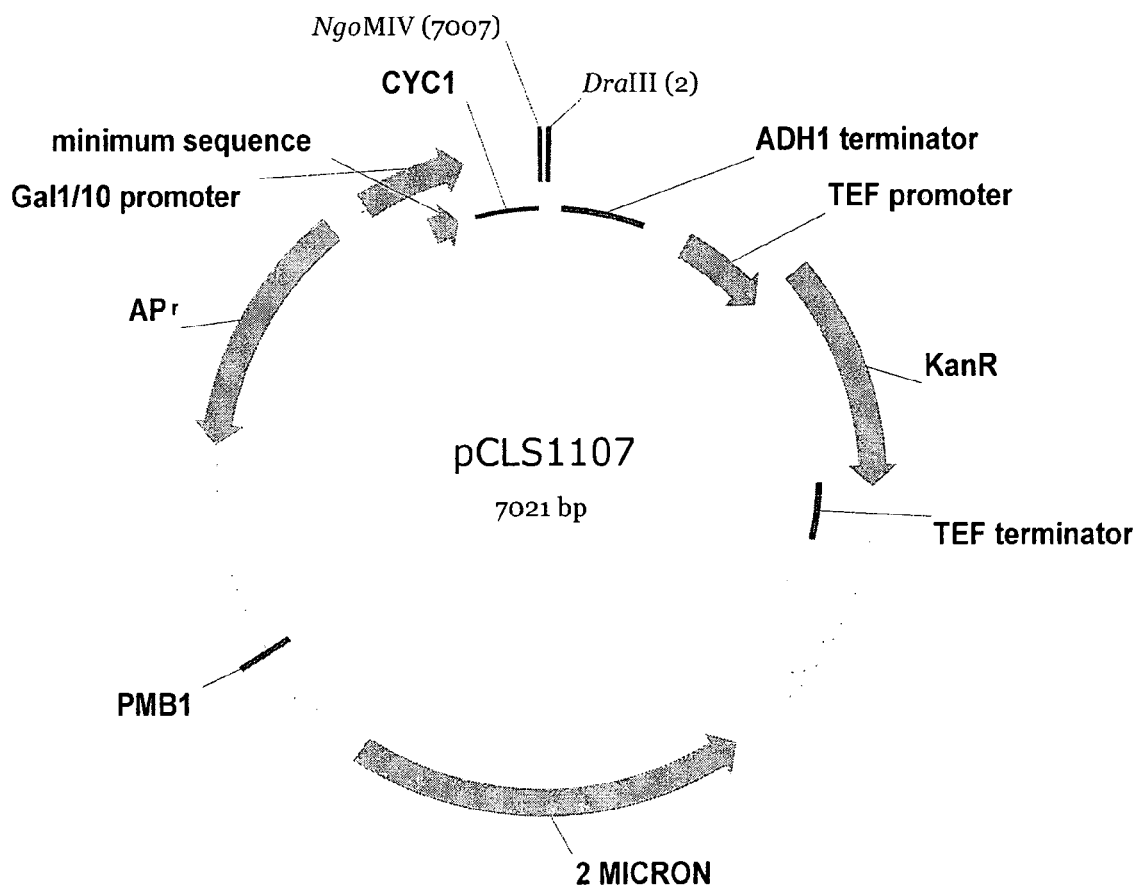

FIG. 8: pCLS1107 plasmid map.

Figure 9:
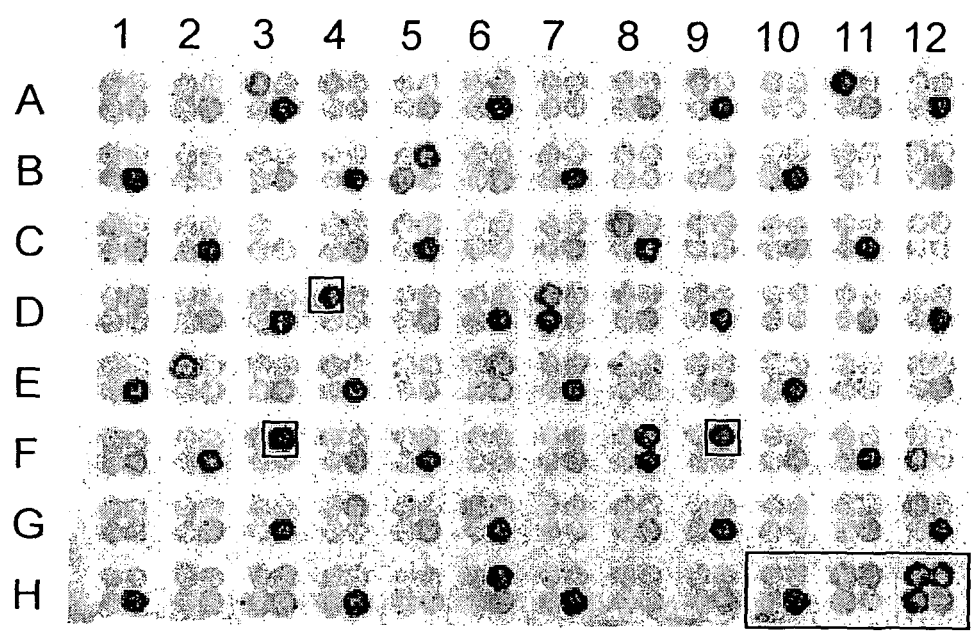

FIG. 9: Cleavage of GSCHO1.4 target by combinatorial variants. The figure displays an example of screening of I-CreI combinatorial variants with the GSCHO1.4 target. H10, H11 and H12 are negative and positive controls of different strength. On the filter, the sequence of the positive variants at positions D4, F3 and F9 are KRDYQS/RHRDI, KRGYQS/KARDI and KRDYQS/RNRDI, respectively (according to the nomenclature of Table VII).

FIG. 10: Cleavage of the GSCHO1.2 and GSCHO1 target sequences by heterodimeric combinatorial variants. A. Example of screening of combinations of I-CreI variants against the GSCHO1.2 target. B. Screening of the same combinations of I-CreI variants against the GSCHO1 target.

All heterodimers tested resulted in cleavage of the GSCHO1.2 target. The heterodimers displaying the strongest signal with the GSCHO1 target are observed at positions D3, D7, D9 and E2, corresponding to yeast co-expressing the GSCHO1.3 variant KRSRES/DYSYQ with the GSCHO1.4 variants KRGYQS/KHRDI, KRGYQS/KNRDI, KRCYQS/RHRDI or KRGYQS/RHRDI, respectively. E10, E11 and E12 are negative and positive controls of different strength.

Figure 11:
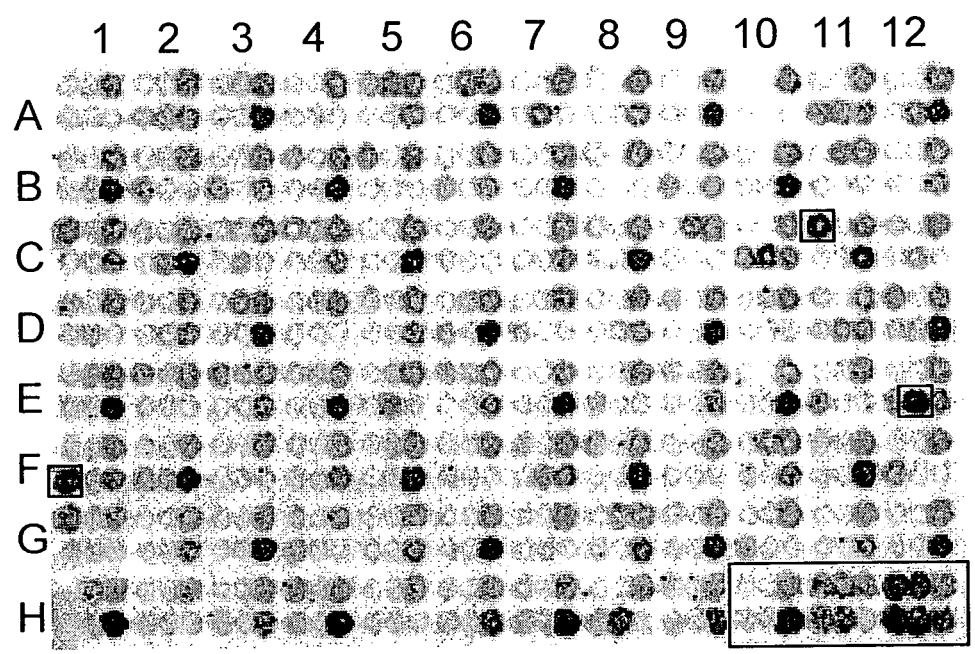

FIG. 11: Cleavage of the GSCHO1 target. Example of screening against the GSCHO1 target of I-CreI refined variants obtained by random mutagenesis of variants cleaving GSCHO1.3 (example 5) and co-expressed with a variant cutting GSCHO1.4 (KRGYQS/KNRDI according to Table VIII).
Each cluster contains 6 spots: In the 4 left spots, the yeast strain containing the GSCHO1 target and the GSCHO1.4 variant are mated with 4 different clones from the library (except for H10, H11 and H12: negative and positive controls of different strength). The top right spot is the GSCHO1.4 variant/GSCHO1 target strain mated with one of the initial GSCHO1.3 variants KRSRES/DYSYQ (according to the nomenclature of Table VI); the lower right spot is an internal control. On the filter, the sequence of the positive variants at positions C11, E12 and F1 are 30R,33R,38E,44D,66H,68Y, 70S,75Y,77Q,132V; 7E,19A,30R,33R,38E,44D,68Y, 70S,75Y,77Q,120A, and 30R,33R,38E,44D,68Y,70S,75Y,77Q,87L, respectively.

Figure 12:
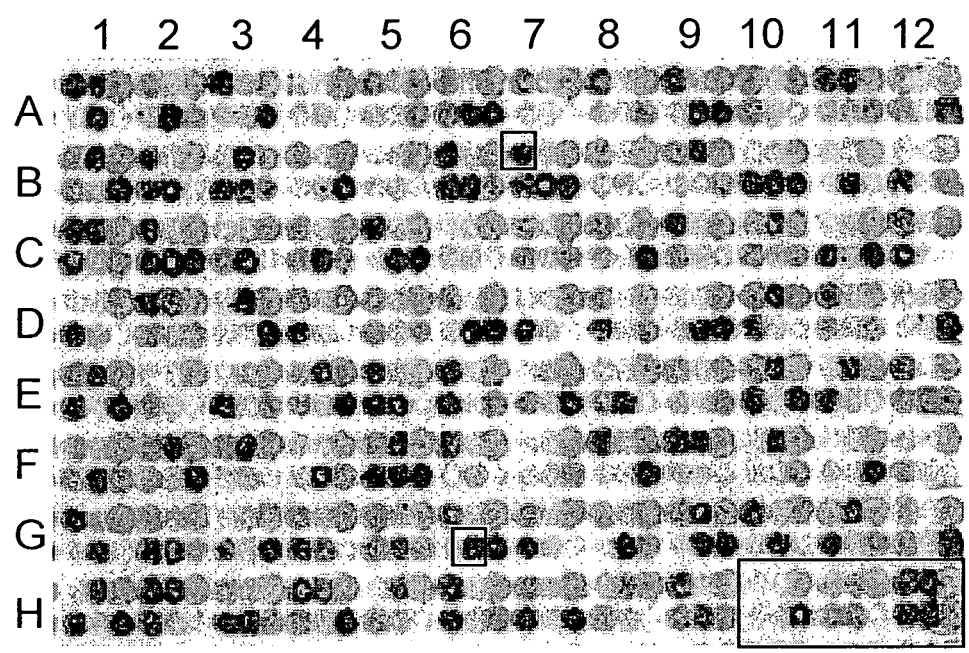

FIG. 12: Cleavage of the GSCHO1 target. Example of screen against the GSCHO1 target of the libraries constructed in example 6 by site-directed mutagenesis of initial variants cleaving the GSCHO1.3 target and co-expressed with a variant cutting GSCHO1.4 (KRGYQS/KNRDI according to Table VIII).
Each cluster contains 6 spots: For each spot, the yeast strain containing the GSCHO1 target and the GSCHO1.4 variant is mated with; 2 different clones from the library containing the E80K' substitution (left spots) 2 different clones from the F87L library (middle spots), or KRSRES/DYSYQ, a variant cleaving GSCHO1.3 described in example 3 (upper right spot). The lower right spot is an internal control. H10, H11 and H12 are negative and positive controls of different strength. The sequence of the positive variants at positions B7, and G6 are 30R,33R,38E,44D,68Y,70S,75Y,77Q,80K, and 30R,33R,38E,44D,68Y,70S,75Y,77Q, 87L, respectively.

Figure 13:
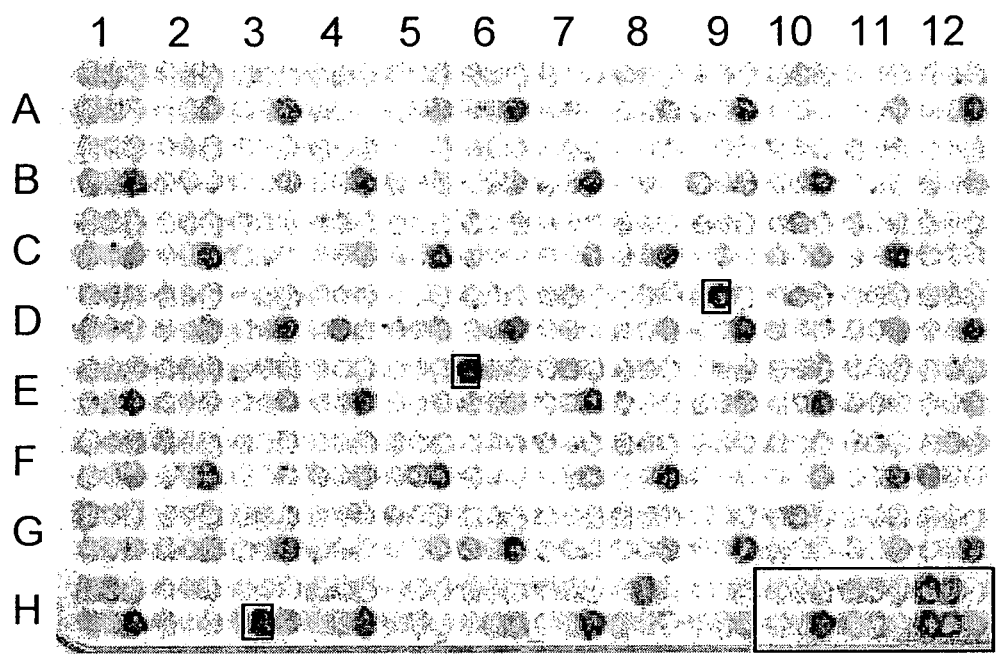

FIG. 13: Cleavage of the GSCHO1 target. Example of screen against the GSCHO1 target of I-CreI refined variants obtained by random mutagenesis of variants cleaving GSCHO1.4 (example 7) and co-expressed with a variant cutting GSCHO1.3 (KRSRES/DYSYQ according to Table VI).
Each cluster contains 6 spots: In the 4 left spots, the yeast strain containing the GSCHO1 target and the GSCHO1.3 variant are mated with 4 different clones from the library (except for H10, H11 and H12: negative and positive controls of different strength). The top right spot is the GSCHO1.3 variant/GSCHO1 target strain mated with one of the initial GSCHO1.4 variants KRGYQS/KYSNI (according to the nomenclature of Table VIII); the lower right spot is an internal control. On the filter, the sequence of the positive variants at positions E6, D9 and H3 are 30R,32G,44R,68H,132V,154G; 30R,33H,68A,77R, and 2S,30R,33H,68A,77R, respectively.

Figure 14:
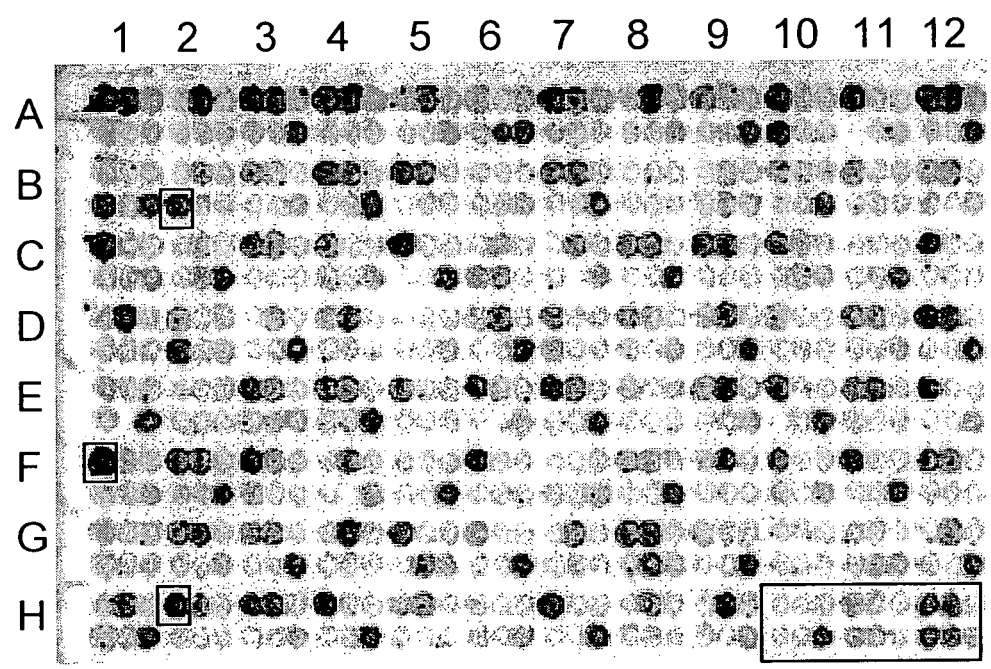

FIG. 14: Cleavage of the GSCHO1 target. Example of screen against the GSCHO1 target of the libraries constructed in example 8 by site-directed mutagenesis of initial variants cleaving the GSCHO1.4 target and co-expressed with a variant cutting GSCHO1.3 (KRSRES/DYSYQ according to Table VI).
Each cluster contains 6 spots: For each spot, the yeast strain containing the GSCHO1 target and the GSCHO1.3 variant is mated with; 2 different clones from the library containing the G19S substitution (top 2 spots) 2 different clones from the F54L library (bottom 2 spots), or KRGYQS/KYSNI, a variant cleaving GSCHO1.4 described in example 4 (upper right spot). The lower right spot is an internal control. H10, H11 and H12 are negative and positive controls of different strength. The sequence of the positive variants at positions B2, F1, and H2 are 30R,32G,44R,54L,68H; 19S,30R,32G, 44K,45M,68H and 19S,30R,33H,68A,77R, respectively.

Figure 15:
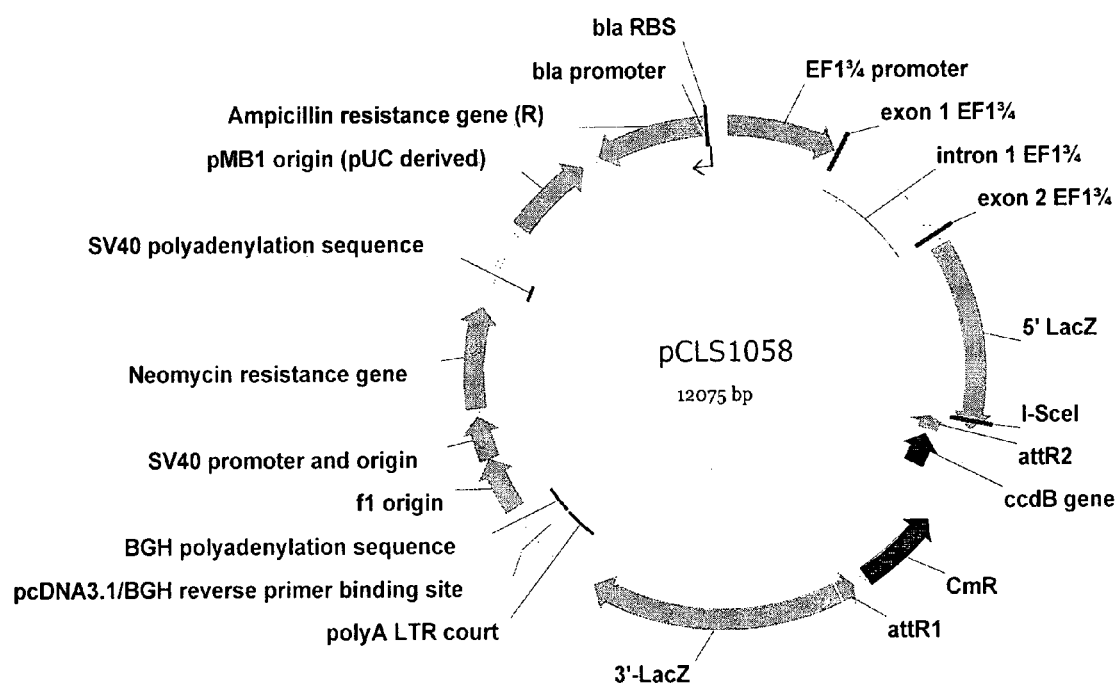

FIG. 15: pCLS1058 plasmid map.

Figure 16:
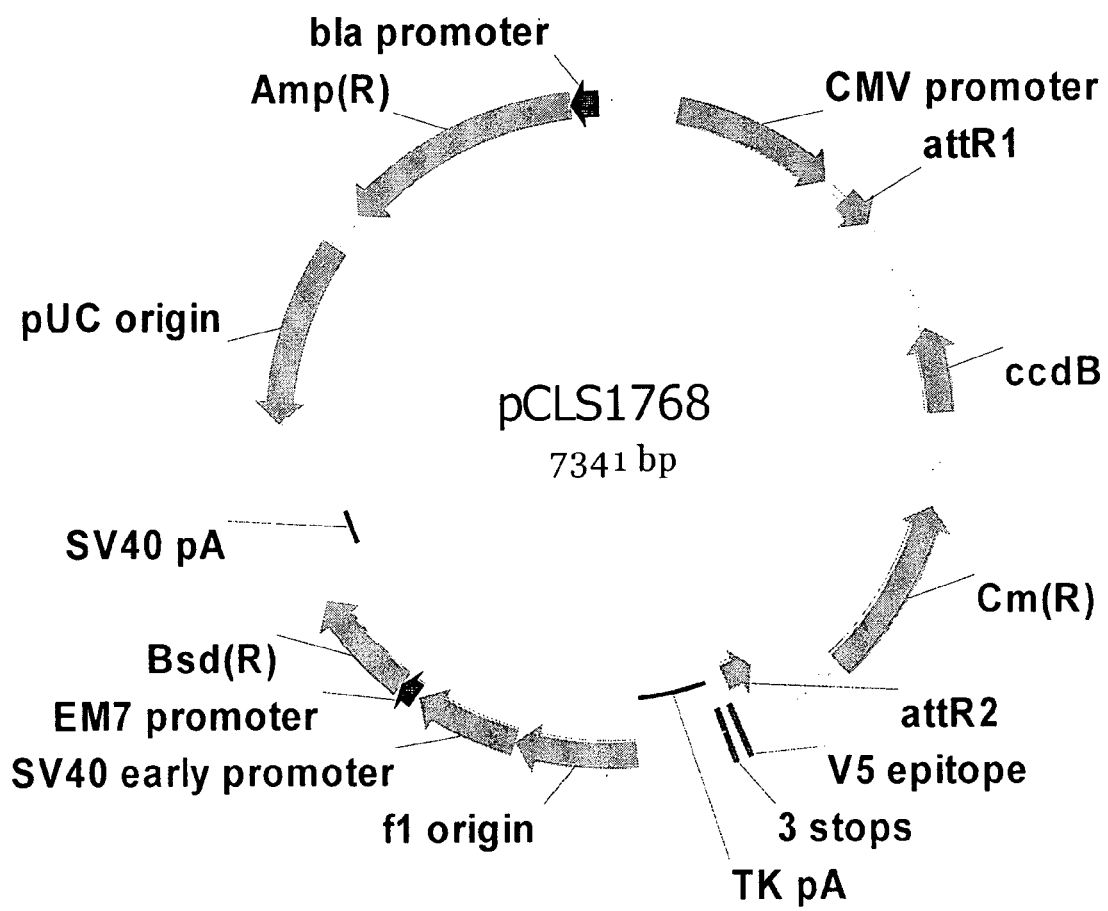

FIG. 16: pCLS1768 plasmid map.

Figure 17:
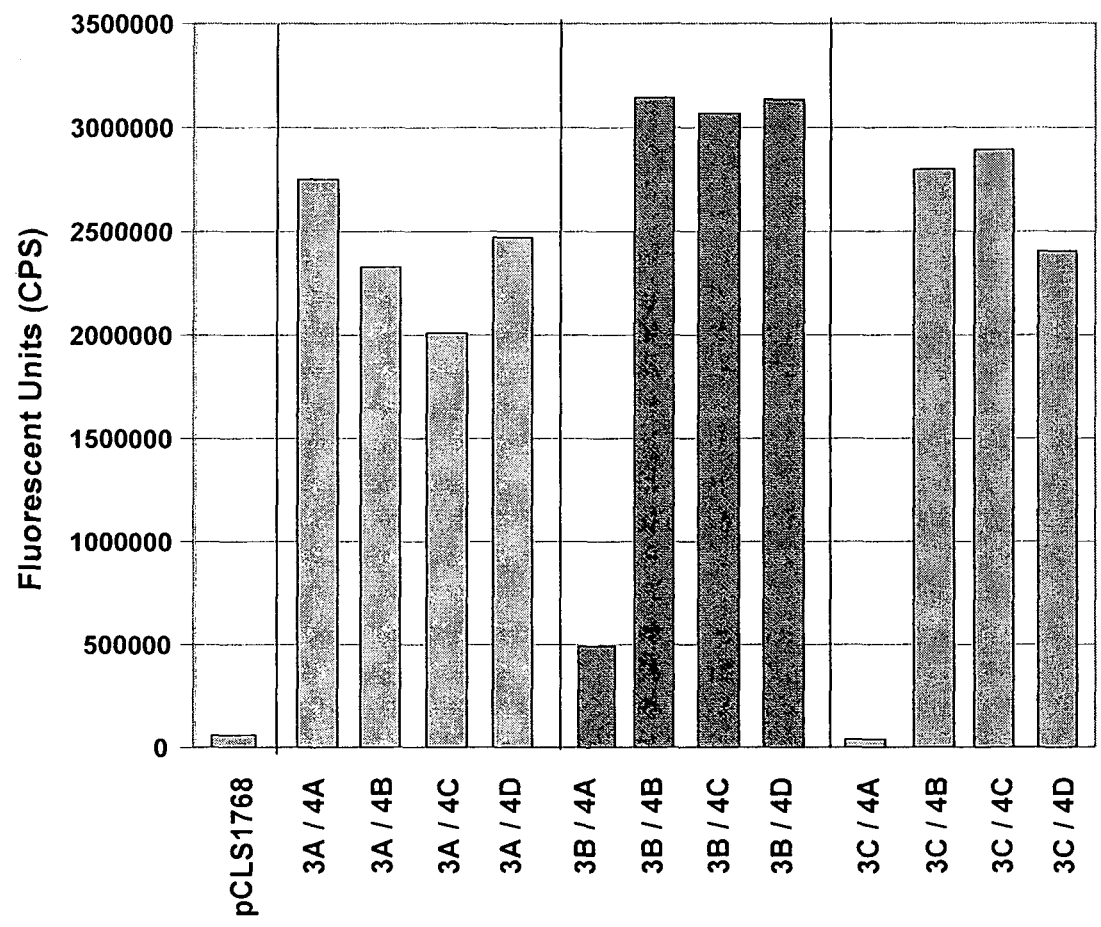

FIG. 17: GSCHO1 target cleavage in CHO cells. Extrachromosomal cleavage efficiency of the GSCHO1 target sequence in mammalian cells was compared for twelve heterodimeric combinations. The sequences of the variants tested are described in table XV. The negative control pCLS1768 is an empty expression vector.

FIG. 18 represents meganuclease target sequences found in the human GS gene and examples of I-CreI variants which are able to cleave said DNA targets; at least one example of variant (heterodimer formed by a first and a second I-CreI variant monomer) is presented for each target. The exons closest to the target sequences, and the exon junctions are indicated (columns 1 and 2), the sequence of the DNA target is presented (column 3), with its sequence identification number (column 4) and the position of its first nucleotide by reference to human GS gene sequence (9782 bp; accession number NC_000001.9; column 5). The minimum repair matrix for repairing the cleavage at the target site is indicated by its first nucleotide (start, column 10) and last nucleotide (end, column 11). The sequence of each I-CreI variant is defined by the mutated residues at the indicated positions (columns 6 and 8) and the corresponding sequence identification number (columns 7 and 9). For example, the first heterodimeric variant of FIG. 18 consists of a first monomer having T, G, V, E, N, R and K at positions 30, 33, 44, 68, 75, 77 and 80, respectively and a second monomer having R, T, N, Q, D, S, R and T at positions 30, 32, 33, 40, 44, 68, 70, 75 and 77, respectively. The positions are indicated by reference to I-CreI sequence (SEQ ID NO: 1); I-CreI has N, S, Y, S, Q, R, R, D, I and E, at positions 30, 32, 33, 40, 44, 68, 70, 75, 77 and 80, respectively.

FIG. 19 represents meganuclease target sequences found in the mouse GS gene and examples of I-CreI variants which are able to cleave said DNA targets; at least one example of variant (heterodimer formed by a first and a second I-CreI variant monomer) is presented for each target. The exons closest to the target sequences, and the exon junctions are indicated (columns 1 and 2), the sequence of the DNA target is presented (column 3), with its sequence identification number (column 4) and the position of its first nucleotide by reference to mouse GS gene sequence (SEQ ID NO: 3; column 5). The minimum repair matrix for repairing the cleavage at the target site is indicated by its first nucleotide (start, column 10) and last nucleotide (end, column 11). The sequence of each I-CreI variant is defined by the mutated residues at the indicated positions (columns 6 and 8) and the corresponding sequence identification number (columns 7 and 9). For example, the first heterodimeric variant of FIG. 19 consists of a first monomer having C, C, H, K, Y, S and N at positions 32, 33, 38, 44, 68, 70 and 75, respectively and a second monomer having R, T, Y, S, R and T at positions 30, 44, 68, 70, 75 and 77, respectively. The positions are indicated by reference to I-CreI sequence (SEQ ID NO: 1); I-CreI has N, S, Y, Q, Q, R, R, D, I and E, at positions 30, 32, 33, 38, 44, 68, 70, 75, 77 and 80 respectively.

FIG. 20 represents meganuclease target sequences found in the Chinese Hamster (*Criteculus griseus*.) GS gene and examples of I-CreI variants which are able to cleave said DNA targets; at least one example of variant (heterodimer formed by a first and a second I-CreI variant monomer) is presented for each target. The exons closest to the target sequences, are indicated (column 1), the sequence of the DNA target is presented (column 2), with its sequence identification number (column 3) and the position of its first nucleotide by reference to Chinese Hamster GS mRNA sequence (GenBank X03495; column 4). The sequence of each I-CreI variant is defined by the mutated residues at the indicated positions (columns 5 and 7) and the corresponding sequence identification number (columns 6 and 8). For example, the first heterodimeric variant of FIG. 20 consists of a first monomer having C, C, H, K, Y, S and N at positions 32, 33, 38, 44, 68, 70 and 75, respectively and a second monomer having R, T, Y, S, R and T at positions 30, 44, 68, 70, 75 and 77, respectively. The positions are indicated by reference to I-CreI sequence (SEQ ID NO: 1); I-CreI has N, S, Y, Q, Q, R, R, D, I and E, at positions 30, 32, 33, 38, 44, 68, 70, 75, 77 and 80 respectively.

EXAMPLE 1

Strategy for Engineering Novel Meganucleases Cleaving a Target from the Glutamine Synthetase (GS) Gene GSCHO1 is a 22 bp (non-palindromic) target located in the coding sequence of both the mouse and the *Criteculus griseus* (Chinese Hamster) Glutamine Synthetase gene. The target sequence corresponds to positions 3060-3083 of the mouse Glutamine Synthetase gene (accession number NC000067.5; FIG. 2A) and positions 204 to 227 of the *Criteculus griseus* Glutamine Synthetase (GS) cDNA (accession number X03495; FIG. 2B).

The GSCHO1 sequence is partly a patchwork of the 10GCC_P, 10GGA_P, 5AGG_P and 5_TTC_P targets (FIG. 4) which are cleaved by previously identified meganucleases, obtained as described in International PCT Applications WO 2006/097784 and WO 2006/097853; Arnould et al., J. Mol. Biol., 2006, 355, 443-458; Smith et al., Nucleic Acids Res., 2006. Thus, GSCHO1 could be cleaved by combinatorial variants resulting from these previously identified meganucleases.

The 10GCC_P, 10GGA_P, 5AGG_P and 5_TTC_P target sequences are 24 bp derivatives of C1221, a palindromic sequence cleaved by I-CreI (Arnould et al., precited). However, the structure of I-CreI bound to its DNA target suggests that the two external base pairs of these targets (positions –12 and 12) have no impact on binding and cleavage (Chevalier et al., Nat. Struct. Biol., 2001, 8, 312-316; Chevalier and Stoddard, Nucleic Acids Res., 2001, 29, 3757-3774; Chevalier et al., J. Mol. Biol., 2003, 329, 253-269), and in this study, only positions –11 to 11 were considered. Consequently, the GSCHO1 series of targets were defined as 22 bp sequences instead of 24 bp. GSCHO1 differs from C1221 in the 4 bp central region. According to the structure of the I-CreI protein bound to its target, there is no contact between the 4 central base pairs (positions –2 to 2) and the I-CreI protein (Chevalier et al., Nat. Struct. Biol., 2001, 8, 312-316; Chevalier and Stoddard, Nucleic Acids Res., 2001, 29, 3757-3774; Chevalier et al., J. Mol. Biol., 2003, 329, 253-269). Thus, the bases at these positions should not impact the binding efficiency. However, they could affect cleavage, which results from two nicks at the edge of this region. Thus, the gtga sequence in –2 to 2 was first substituted with the gtac sequence from C1221, resulting in target GSCHO1.2 (FIG. 4). Then, two palindromic targets, GSCHO1.3 and GSCHO1.4, were derived from GSCHO1.2 (FIG. 4). Since GSCHO1.3 and GSCHO1.4 are palindromic, they should be cleaved by homodimeric proteins. Thus, proteins able to cleave the GSCHO1.3 and GSCHO1.4 sequences as homodimers were first designed (examples 2 and 3) and then co-expressed to obtain heterodimers cleaving GSCHO1 (example 4). Heterodimers cleaving the GSCHO1.2 and GSCHO1 targets could be identified. In order to improve cleavage activity for the GSCHO1 target, a series of variants cleaving GSCHO1.3 and GSCHO1.4 was chosen, and then refined. The chosen variants were subjected to random or site-directed mutagenesis, and used to form novel heterodimers that were screened against the GSCHO1 target (examples 5, 6, 7 and 8). Heterodimers could be identified with an improved cleavage activity for the GSCHO1 target. Chosen heterodimers were subsequently cloned into mammalian expression vectors and screened against the GSCHO1 target in CHO cells (example 9). Strong cleavage activity of the GSCHO1 target could be observed for these heterodimers in mammalian cells.

EXAMPLE 2

Identification of Meganucleases Cleaving GSCHO1.3

This example shows that I-CreI variants can cut the GSCHO1.3 DNA target sequence derived from the left part of the GSCHO1.2 target in a palindromic form (FIG. 4). Target sequences described in this example are 22 bp palindromic sequences. Therefore, they will be described only by the first 11 nucleotides, followed by the suffix_P (For example, target GSCHO1.3 will be noted tgccccagggt_P).

GSCHO1.3 is similar to 10GCC_P at positions ±1, ±2, ±6, ±8, ±9, and ±10 and to 5AGG_P at positions ±1, ±2, ±3, ±4, ±5 and ±6. It was hypothesized that positions ±7 and ±11 would have little effect on the binding and cleavage activity. Variants able to cleave the 10GCC_P target were obtained by mutagenesis of I-CreI N75 or D75, at positions 28, 30, 32, 33, 38, 40 and 70, as described previously in Smith et al. Nucleic Acids Res., 2006, 34, e149; International PCT Applications WO 2007/060495 and WO 2007/049156. Variants able to cleave 5AGG_P were obtained by mutagenesis on I-CreI N75 at positions 24, 44, 68, 70, 75 and 77 as described in Arnould et al., J. Mol. Biol., 2006, 355, 443-458; Smith et al. Nucleic Acids Res., 2006, 34, e149; International PCT Applications WO 2006/097784, WO 2006/097853, WO 2007/060495 and WO 2007/049156.

Both sets of proteins are mutated at position 70. However, the existence of two separable functional subdomains was hypothesized. This implies that this position has little impact on the specificity at bases 10 to 8 of the target. Mutations at positions 24 found in variants cleaving the 5AGG_P target will be lost during the combinatorial process. But it was hypothesized that this will have little impact on the capacity of the combined variants to cleave the GSCHO1.3 target.

Therefore, to check whether combined variants could cleave the GSCHO1.3 target, mutations at positions 44, 68, 70, 75 and 77 from proteins cleaving 5AGG_P were combined with the 28, 30, 32, 33, 38 and 40 mutations from proteins cleaving 10GCC_P.

A) Material and Methods a) Construction of Target Vector

The target was cloned as follows: an oligonucleotide corresponding to the GSCHO1.3 target sequence flanked by gateway cloning sequences was ordered from PROLIGO: 5' tggcatacaagtttctgccccagggtaccctggggcagcaatcgtctgtca 3' (SEQ ID NO: 183). Double-stranded target DNA, generated by PCR amplification of the single stranded oligonucleotide, was cloned using the Gateway protocol (INVITROGEN) into the yeast reporter vector (pCLS1055, FIG. 5). Yeast reporter vector was transformed into *Saccharomyces cerevisiae* strain FYBL2-7B (MAT a, ura3Δ851, trp1Δ63, leu2Δ1, lys2Δ202), resulting in a reporter strain.

b) Mating of Meganuclease Expressing Clones and Screening in Yeast

I-CreI variants cleaving 10GCC_P or 5AGG_P were previously identified, as described in Smith et al. Nucleic Acids Res., 2006, 34, e149; International PCT Applications WO 2007/060495 and WO 2007/049156, and Arnould et al., J. Mol. Biol., 2006, 355, 443-458; International PCT Applications WO 2006/097784 and WO 2006/097853, respectively for the 10GCC_P and 5AGG_P targets. In order to generate I-CreI derived coding sequences containing mutations from both series, separate overlapping PCR reactions were carried out that amplify the 5' end (aa positions 1-43) or the 3' end (positions 39-167) of the I-CreI coding sequence. For both the 5' and 3' end, PCR amplification is carried out using primers (Gall OF 5'-gcaactttagtgctgacacatacagg-3' (SEQ ID NO: 186) or Gal10R 5'-acaaccttgattggagacttgacc-3'(SEQ ID NO: 187)) specific to the vector (pCLS0542, FIG. 6) and primers (assF 5'-ctannnttgaccttt-3' (SEQ ID NO: 188) or assR 5'-aaaggtcaannntag-3'(SEQ ID NO: 189)), where nnn codes for residue 40, specific to the I-CreI coding sequence for amino acids 39-43. The PCR fragments resulting from the amplification reaction realized with the same primers and with the same coding sequence for residue 40 were pooled. Then, each pool of PCR fragments resulting from the reaction with primers Gall OF and assR or assF and Gal10R was mixed in an equimolar ratio. Finally, approximately 25 ng of each final pool of the two overlapping PCR fragments and 75 ng of vector DNA (pCLS0542, FIG. 6) linearized by digestion with NcoI and EagI were used to transform the yeast *Saccharomyces cerevisiae* strain FYC2-6A (MATα, trp1Δ63, leu2Δ1, his3Δ200) using a high efficiency LiAc transformation protocol (Gietz and Woods, Methods Enzymol., 2002, 350, 87-96). An intact coding sequence containing both groups of mutations is generated by in vivo homologous recombination in yeast.

c) Mating of Meganuclease Expressing Clones and Screening in Yeast

Screening was performed as described previously (Arnould et al., J. Mol. Biol., 2006, 355, 443-458). Mating was performed using a colony gridder (QpixII, GENETIX). Variants were gridded on nylon filters covering YPD plates, using a low gridding density (4-6 spots/cm$^2$). A second gridding process was performed on the same filters to spot a second layer consisting of the reporter-harboring yeast strain. Membranes were placed on solid agar YPD rich medium, and incubated at 30° C. for one night, to allow mating. Next, filters were transferred to synthetic medium, lacking leucine and tryptophan, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

d) Sequencing of Variants

To recover the variant expression plasmids, yeast DNA was extracted using standard protocols and used to transform *E. coli*. Sequencing of variant ORFs was then performed on the plasmids by MILLEGEN SA. Alternatively, ORFs were amplified from yeast DNA by PCR (Akada et al., Biotechniques, 2000, 28, 668-670), and sequencing was performed directly on the PCR product by MILLEGEN SA.

B) Results

I-CreI combinatorial variants were constructed by associating mutations at positions 44, 68, 70, 75 and 77 from proteins cleaving 5AGG_P with the 28, 30, 32, 33, 38 and 40 mutations from proteins cleaving 10GCC_P on the I-CreI scaffold, resulting in a library of complexity 2303. Examples of combinatorial variants are displayed in Table V. This library was transformed into yeast and 4608 clones (2 times the diversity) were screened for cleavage against the GSCHO1.3 DNA target (tgccccagggt_P). Two positive clones were found (one strong cutter and one weak cutter), which after sequencing turned out to correspond to 2 different novel endonuclease variants (Table VI). Examples of positives are shown in FIG. 7. These two variants display non parental combinations at positions 28, 30, 32, 33, 38, 40 or 44, 68, 70, 75, 77. Such combinations likely result from PCR artifacts during the combinatorial process. Alternatively, the variants may be I-CreI combined variants resulting from micro-recombination between two original variants during in vivo homologous recombination in yeast.

GSCHO1.4 is similar to 5TTC_P at positions ±1, ±2, ±3, ±4, ±5 and ±8 and to 10GGA_P at positions ±1, ±2, ±3, ±4, ±8, ±9 and ±10. It was hypothesized that positions ±6, ±7 and ±11 would have little effect on the binding and cleavage activity. Variants able to cleave 5TTC_P were obtained by mutagenesis of I-CreI N75 at positions 44, 68, 70, 75 and 77,

TABLE V

Panel of variants* theoretically present in the combinatorial library

| Amino acids at positions 44, 68, 70, 75 and 77 (ex: ARNNI stands for A44, R68, N70, N75 and I77) | Amino acids at positions 28, 30, 32, 33, 38 and 40 (ex: KHSSQS stands for K28, H30, S32, S33, Q38 and S40) | | | | | | | | | |
|---|---|---|---|---|---|---|---|---|---|---|
| | KHSSQS | KKSAQS | KRDYQS | KRSCQS | KRSNQS | KTSYQS | KTSRQS | KNSHHS | KNSRES | KNSRQG | KTSHQS |
| ARNNI | | | | | | | | | | | |
| ARSER | | | | | | | | | | | |
| ARSNI | | | | | | | | | | | |
| ARSYY | | | | | | | | | | | |
| DRSRI | | | | | | | | | | | |
| HRSDI | | | | | | | | | | | |
| NRSHT | | | | | | | | | | | |
| NYSNT | | | | | | | | | | | |
| NRSYI | | | | | | | | | | | |
| NRSYN | | | | | | | | | | | |
| RTSYN | | | | | | | | | | | |
| RYSEY | | | | | | | | | | | |
| SRSYQ | | | | | | | | | | | |
| SYSYV | | | | | | | | | | | |
| TRSER | | | | | | | | | | | |
| TRSNS | | | | | | | | | | | |
| TSSKN | | | | | | | | | | | |
| TYSER | | | | | | | | | | | |
| YESRL | | | | | | | | | | | |
| YRSNI | | | | | | | | | | | |
| YRSNV | | | | | | | | | | | |
| YRSQI | | | | | | | | | | | |
| YRSQV | | | | | | | | | | | |
| YYSYR | | | | | | | | | | | |

*Only 264 out of the 2303 combinations are displayed. None of them were identified in the positive clones.

TABLE VI

| I-CreI variants capable of cleaving the GSCHO1.3 DNA target. | |
|---|---|
| Amino acids at positions 28, 30, 32, 33, 38, 40/44, 68, 70, 75 and 77 of the I-CreI variants (ex: KRSRES/TYSNI stands for K28, R30, S32, R33, E38, S40/T44, Y68, S70, N75 and I77) | SEQ ID NO: |
| KRSRES/TYSNI | 184 |
| KRSRES/DYSYQ | 110 |

EXAMPLE 3

Making of Meganucleases Cleaving GSCHO1.4

This example shows that I-CreI variants can cleave the GSCHO1.4 DNA target sequence derived from the right part of the GSCHO1.2 target in a palindromic form (FIG. 4). All target sequences described in this example are 22 bp palindromic sequences. Therefore, they will be described only by the first 11 nucleotides, followed by the suffix_P (for example, GSCHO1.4 will be called tggactttcgt_P).

as described previously (Arnould et al., J. Mol. Biol., 2006, 355, 443-458; Smith et al. Nucleic Acids Res., 2006, 34, e149; International PCT Applications WO 2006/097784, WO 2006/097853, WO 2007/060495 and WO 2007/049156). Variants able to cleave the 10GGA_P target were obtained by mutagenesis of I-CreI N75 or D75, at positions 28, 30, 32, 33, 38, 40 and 70, as described previously in Smith et al. Nucleic Acids Res., 2006, 34, e149; International PCT Applications WO 2007/060495 and WO 2007/049156.

Both sets of proteins are mutated at position 70. However, the existence of two separable functional subdomains was hypothesized. This implies that this position has little impact on the specificity at bases 10 to 8 of the target.

Therefore, to check whether combined variants could cleave the GSCHO1.4 target, mutations at positions 44, 68, 70, 75 and 77 from proteins cleaving 5TTC_P were combined with the 28, 30, 32, 33, 38 and 40 mutations from proteins cleaving 10GGA_P.

A) Material and Methods a) Construction of Target Vector

The experimental procedure is as described in example 2, with the exception that an oligonucleotide corresponding to the GSCHO1.4 target sequence was used: 5' tggcata-caagttttggactttcgtacgaaagtccaacaatcgtctgtca 3' (SEQ ID NO: 185).

b) Construction of Combinatorial Variants

I-CreI variants cleaving 10GGA_P or 5TTC_P were previously identified, as described in Smith et al. Nucleic Acids Res., 2006, 34, e149; International PCT Applications WO 2007/060495 and WO 2007/049156, and Arnould et al., J. Mol. Biol., 2006, 355, 443-458; International PCT Applications WO 2006/097784 and WO 2006/097853, respectively for the 10GGA_P and 5TTC_P targets. In order to generate I-CreI derived coding sequences containing mutations from both series, separate overlapping PCR reactions were carried out that amplify the 5' end (aa positions 1-43) or the 3' end (positions 39-167) of the I-CreI coding sequence. For both the 5' and 3' end, PCR amplification is carried out using primers (Gal10F 5'-gcaactttagtgctgacacatacagg-3' (SEQ ID NO: 186) or Gal10R 5'-acaaccttgattggagacttgacc-3' (SEQ ID NO: 187)) specific to the vector (pCLS1107, FIG. 8) and primers (assF 5'-ctannnttgaccttt-3' (SEQ ID NO: 188) or assR 5'-aaaggt-caannntag-3'(SEQ ID NO: 189)), where nnn codes for residue 40, specific to the I-CreI coding sequence for amino acids 39-43. The PCR fragments resulting from the amplification reaction realized with the same primers and with the same coding sequence for residue 40 were pooled. Then, each pool of PCR fragments resulting from the reaction with primers Gal10F. and assR or assF and Gal10R was mixed in an equimolar ratio. Finally, approximately 25 ng of each final pool of the two overlapping PCR fragments and 75 ng of vector DNA (pCLS1107, FIG. 8) linearized by digestion with DraIII and NgoMIV were used to transform the yeast *Saccharomyces cerevisiae* strain FYC2-6A (MATα, trp1Δ63, leu2 Δ1, his3Δ200) using a high efficiency LiAc transformation protocol (Gietz and Woods, Methods Enzymol., 2002, 350, 87-96). An intact coding sequence containing both groups of mutations is generated by in vivo homologous recombination in yeast.

c) Mating of Meganuclease Expressing Clones and Screening in Yeast

Screening was performed as described previously (Arnould et al., J. Mol. Biol., 2006, 355, 443-458). Mating was performed using a colony gridder (QpixII, GENETIX). Variants were gridded on nylon filters covering YPD plates, using a low gridding density (4-6 spots/cm²). A second gridding process was performed on the same filters to spot a second layer consisting of the reporter-harboring yeast strain. Membranes were placed on solid agar YPD rich medium, and incubated at 30° C. for one night, to allow mating. Next, filters were transferred to synthetic medium, lacking tryptophan, adding G418, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software. Positives resulting clones were verified by sequencing (MILLEGEN) as described in example 2.

B) Results

I-CreI combinatorial variants were constructed by associating mutations at positions 44, 68, 70, 75 and 77 from proteins cleaving 5TTC_P with the 28, 30, 32, 33, 38 and 40 mutations from proteins cleaving 10GGA_P on the I-CreI scaffold, resulting in a library of complexity 1600. Examples of combinatorial variants are displayed in Table VII. This library was transformed into yeast and 3456 clones (2.2 times the diversity) were screened for cleavage against the GSCHO1.4 DNA target (tggactttcgt_P). A total of 250 positive clones were found to cleave GSCHO1.4. Sequencing and validation by secondary screening of 91 of the best I-CreI variants resulted in the identification of 57 different novel endonucleases. Examples of positives are shown in FIG. 9. The sequence of several of the variants identified display non parental combinations at positions 28, 30, 32, 33, 38, 40 or 44, 68, 70, 75, 77 as well as additional mutations (see examples Table VIII). Such variants likely result from PCR artifacts during the combinatorial process. Alternatively, the variants may be I-CreI combined variants resulting from micro-recombination between two original variants during in vivo homologous recombination in yeast.

TABLE VII

Panel of variants* theoretically present in the combinatoriall library

| Amino acids at positions 44, 68, 70, 75 and 77 (ex: HNRDI stands for H44, N68, R70, D75 and I77) | Amino acids at positions 28, 30, 32, 33, 38 and 40 (ex: KRGYQS stands for K28, R30, G32, Y33, Q38 and S40) | | | | | | | | |
|---|---|---|---|---|---|---|---|---|---|
| | KRGYQS | KKSAQS | KKSSQS | KRSYQS | KNAHQS | KNERQS | KRDYQS | KRCYQS | KNTHQS | KTSHRS |
| HNRDI | | | | | | | + | | | |
| KAANI | | | | | | | | | | |
| KARDI | + | | | + | | | | | | |
| KASNT | | | | | | | | | | |
| KNSNI | + | | | | | | | | | |
| KRDNI | | | | | | | | | | |
| KRNDI | | | | | | | | | | |
| KYSNV | | | | | | | | | | |
| NHNNI | | | | | | | | | | |
| NYSRI | + | | | | | | | | | |
| NYSRY | + | + | + | + | | | | | | + |
| QASNR | | | | | | | | | | |
| QHHNI | | | | | | | | | | |
| QRHNI | | | | | | | | | | |
| QRNNI | | | | | | | | | | |
| QRPNI | | | | | | | | | | |
| QRRNI | | + | | | | | | | | |
| QTRDI | | | | | | | | | | |
| RHRDI | + | + | | | | | + | + | | + |

TABLE VII-continued

Panel of variants* theoretically present in the combinatoriall library

| Amino acids at positions 44, 68, 70, 75 and 77 (ex: HNRDI stands for H44, N68, R70, D75 and I77) | Amino acids at positions 28, 30, 32, 33, 38 and 40 (ex: KRGYQS stands for K28, R30, G32, Y33, Q38 and S40) | | | | | | | | |
|---|---|---|---|---|---|---|---|---|---|
| | KRGYQS | KKSAQS | KKSSQS | KRSYQS | KNAHQS | KNERQS | KRDYQS | KRCYQS | KNTHQS | KTSHRS |
| RNRDI | | | | + | | | + | | | |
| RTRDI | + | | | | | | | | | |
| TYSRV | + | + | | + | | | | | | + |

*Only 220 out of the 1600 combinations are displayed.
+ indicates that a functional combinatorial variant cleaving the GSCHO1.4 target was found among the identified positives.

TABLE VIII

I-CreI variants with additional mutations capable of cleaving the GSCHO1.4 DNA target.

| Amino acids at positions 28, 30, 32, 33, 38, 40/44, 68, 70, 75 and 77 of the I-CreI variants (ex: KRGYQS/KYSNI stands for K28, R30, G32, Y33, Q38, S40/ K44, Y68, S70, N75 and I77) | SEQ ID NO: |
|---|---|
| KRGYQS/KYSNI | 190 |
| KNSHNS/KNSNI + 47K | 191 |
| KRGYQS/KNANI + 59A | 192 |
| KRSTRS/KNSNI | 193 |
| KRGYQS/KYSNV + 45M | 194 |
| KRGYQS/RYSNI | 195 |
| KNAHQS/KPSNI | 196 |
| KRGYQS/KNRDI | 131 |
| KRGYQS/KNRDI | 132 |
| KHRHQS/NYSRY | 197 |
| KRDYQS/QRSRT + 80K | 198 |
| KRDYQS/TRSRI + 80K | 199 |
| KRGYQS/QYSRY | 200 |

EXAMPLE 4

Making of Meganucleases Cleaving GSCHO1.2 and GSCHO1

I-CreI variants able to cleave each of the palindromic GSCHO1.2 derived targets (GSCHO1.3 and GSCHO1.4) were identified in example 2 and example 3. Pairs of such variants (one cutting GSCHO1.3 and one cutting GSCHO1.4) were co-expressed in yeast. Upon co-expression, there should be three active molecular species, two homodimers, and one heterodimer. It was assayed whether the heterodimers that should be formed, cut the GSCHO1.2 and the non palindromic GSCHO1 targets.

A) Materials and Methods
a) Construction of Target Vector

The experimental procedure is as described in example 2, with the exception that an oligonucleotide corresponding to the GSCHO1.2 target sequence: 5' tggcatacaagtttctgc-cccagggtacgaaagtccaacaatcgtctgtca 3'(SEQ ID NO: 201) or the GSCHO1 target sequence: 5' tggcatacaagtttctgccccagggt-gagaaagtccaacaatcgtctgtca 3' (SEQ ID NO: 202) was used.

b) Co-expression of Variants

Yeast DNA was extracted from variants cleaving the GSCHO1.4 target in the pCLS1107 expression vector using standard protocols and was used to transform E. coli. The resulting plasmid DNA was then used to transform yeast strains expressing a variant cutting the GSCHO1.3 target in the pCLS0542 expression vector. Transformants were selected on synthetic medium lacking leucine and containing G418.

c) Mating of Meganucleases Coexpressing Clones and Screening in Yeast

Mating was performed using a colony gridder (QpixII, Genetix). Variants were gridded on nylon filters covering YPD plates, using a low gridding density (4-6 spots/cm$^2$). A second gridding process was performed on the same filters to spot a second layer consisting of different reporter-harboring yeast strains for each target. Membranes were placed on solid agar YPD rich medium, and incubated at 30° C. for one night, to allow mating. Next, filters were transferred to synthetic medium, lacking leucine and tryptophan, adding G418, with galactose (2%) as a carbon source, and incubated for five days at 37° C., to select for diploids carrying the expression and target vectors. After 5 days, filters were placed on solid agarose medium with 0.02% X-Gal in 0.5 M sodium phosphate buffer, pH 7.0, 0.1% SDS, 6% dimethyl formamide (DMF), 7 mM β-mercaptoethanol, 1% agarose, and incubated at 37° C., to monitor β-galactosidase activity. Results were analyzed by scanning and quantification was performed using appropriate software.

B) Results

Co-expression of variants cleaving the GSCHO1.4 target (14 variants chosen among those described in Table VII and Table VIII) and the two variants cleaving the GSCHO1.3 target (described in Table VI) resulted in efficient cleavage of the GSCHO1.2 target in all cases (FIG. 10A). In addition, some of these combinations were able to cut the GSCHO1 natural target that differs from the GSCHO1.2 sequence by 2 bp at positions 1 and 2 (FIG. 10B). Functional combinations are summarized in Table IX and Table X.

TABLE IX

Cleavage of the GSCHO1.2 target by the heterodimeric variants

| | | Amino acids at positions 28, 30, 32, 33, 38, 40/44, 68, 70, 75 and 77 of the I-CreI variants cleaving the GSCHO1.3 target (ex: KRSRES/TYSNI stands for K28, R30, S32, R33, E38, S40/T44, Y68, S70, N75 and I77) | |
|---|---|---|---|
| | | KRSRES/TYSNI | KRSRES/DYSYQ |
| Amino acids at positions 28, 30, 32, 33, 38, 40/44, 68, 70, 75 and 77 Of I-CreI variants cleaving the GSCHO1.4 target (ex: KRGYQS/RHRDI stands for K28, R30, G32, Y33, Q38, S40/R44, H68, R70, D75 and I77) | KRGYQS/RHRDI | + | + |
| | KRGYQS/KHRDI | + | + |
| | KRGYQS/KNRDI | + | + |
| | KRGYQS/NYSRY | + | + |
| | KRGYQS/RTRDI | + | + |
| | KRGYQS/TYSRV | + | + |
| | KRCYQS/RHRDI | + | + |
| | KRGYQS/KARDI | + | + |
| | KRGYQS/QYSRY | + | + |
| | KRGYQS/NYSRI | + | + |
| | KHRHQS/NYSRY | + | + |
| | KKSAQS/NYSRY | + | + |
| | KRDYQS/QRSRT + 80K | + | + |
| | KRDYQS/TRSRI + 80K | + | + |

+ indicates a functional combination

TABLE X

Cleavage of the GSCHO1 target by the heterodimeric variants

| | | Amino acids at positions 28, 30, 32, 33, 38, 40/44, 68, 70, 75 and 77 of the I-CreI variants cleaving the GSCHO1.3 target (ex: KRSRES/TYSNI stands for K28, R30, S32, R33, E38, S40/T44, Y68, S70, N75 and I77) | |
|---|---|---|---|
| | | KRSRES/TYSNI (SEQ ID NO: 184) | KRSRES/DYSYQ (SEQ ID NO: 110) |
| Amino acids at positions 28, 30, 32, 33, 38, 40/44, 68, 70, 75 and 77 Of I-CreI variants cleaving the GSCHO1.4 target (ex: KRGYQS/RHRDI stands for K28, R30, G32, Y33, Q38, S40/R44, H68, R70, D75 and I77) | KRGYQS/RHRDI (SEQ ID NO: 130) | | + |
| | KRGYQS/RHRDI (SEQ ID NO: 131) | | + |
| | KRGYQS/KNRDI (SEQ ID NO: 132) | | + |
| | KRGYQS/NYSRY (SEQ ID NO: 203) | | +* |
| | KRGYQS/RTRDI (SEQ ID NO: 204) | | +* |
| | KRGYQS/TYSRV (SEQ ID NO: 205) | | +* |
| | KRCYQS/RHRDI (SEQ ID NO: 133) | | + |
| | KRGYQS/RHRDI (SEQ ID NO: 206) | | +* |
| | KRGYQS/QYSRY (SEQ ID NO: 200) | | +* |
| | KRGYQS/NYSRI (SEQ ID NO: 207) | | |
| | KHRHQS/NYSRY (SEQ ID NO: 197) | | |
| | KKSAQS/NYSRY (SEQ ID NO: 208) | | +* |

TABLE X-continued

Cleavage of the GSCHO1 target by the heterodimeric variants

| | Amino acids at positions 28, 30, 32, 33, 38, 40/44, 68, 70, 75 and 77 of the I-CreI variants cleaving the GSCHO1.3 target (ex: KRSRES/TYSNI stands for K28, R30, S32, R33, E38, S40/T44, Y68, S70, N75 and I77) |
|---|---|
| KRDYQS/QRSRT + 80K (SEQ ID NO: 198) | +* |
| KRDYQS/TRSRI + 80K (SEQ ID NO: 199) | +* |

+ indicates a functional combination
*indicates that the combination weakly cuts the GSCHO1 target

EXAMPLE 5

Improvement of Meganucleases Cleaving GSCHO1 by Random Mutagenesis of Proteins Cleaving GSCHO1.3 and Assembly with Proteins Cleaving GSCHO1.4

I-CreI variants able to cleave the GSCHO1.2 and GSCHO1 target by assembly of variants cleaving the palindromic GSCHO1.3 and GSCHO1.4 target have been previously identified in example 4. However, these variants display stronger activity with the GSCHO1.2 target compared to the GSCHO1 target.

Therefore the two combinatorial variants cleaving GSCHO1.3 were mutagenized, and variants were screened for cleavage activity of GSCHO1 when co-expressed with a variant cleaving GSCHO1.4. According to the structure of the I-CreI protein bound to its target, there is no contact between the 4 central base pairs (positions −2 to 2) and the I-CreI protein (Chevalier et al., Nat. Struct. Biol., 2001, 8, 312-316; Chevalier and Stoddard, Nucleic Acids Res., 2001, 29, 3757-3774; Chevalier et al., J. Mol. Biol., 2003, 329, 253-269). Thus, it is difficult to rationally choose a set of positions to mutagenize, and mutagenesis was performed on the whole protein. Random mutagenesis results in high complexity libraries. Therefore, to limit the complexity of the variant libraries to be tested, only one of the two components of the heterodimers cleaving GSCHO1 was mutagenized.

Thus, in a first step, proteins cleaving GSCHO1.3 were mutagenized, and in a second step, it was assessed whether they could cleave GSCHO1 when co-expressed with a protein cleaving GSCHO1.4.

A) Material and Methods
a) Construction of Libraries by Random Mutagenesis

Random mutagenesis was performed on a pool of chosen variants, by PCR using $Mn^{2+}$. PCR reactions were carried out that amplify the I-CreI coding sequence using the primers preATGCreFor (5'-gcataaattactatacttctataga-cacgcaaacacaaatacacagcggccttgccacc-3'; SEQ ID NO: 209) and ICreIpostRev (5'-ggctcgaggagctcgtctagag-gatcgctcgagttatcagtcggccgc-3'; SEQ ID NO: 210), which are common to the pCLS0542 (FIG. 6) and pCLS1107 (FIG. 8) vectors. Approximately 25 ng of the PCR product and 75 ng of vector DNA (pCLS0542) linearized by digestion with NcoI and EagI were used to transform the yeast *Saccharomyces cerevisiae* strain FYC2-6A (MATα, trp1Δ63, leu2Δ1, his3Δ200) using a high efficiency LiAc transformation protocol (Gietz and Woods, Methods Enzymol., 2002, 350, 87-96). Expression plasmids containing an intact coding sequence for the I-CreI variant were generated by in vivo homologous recombination in yeast.

b) Variant-Target Yeast Strains, Screening and Sequencing

The yeast strain FYBL2-7B (MAT a, ura3Δ851, trp1Δ63, leu2Δ1, lys2Δ202) containing the GSCHO1 target in the yeast reporter vector (pCLS1055, FIG. 5) was transformed with variants, in the kanamycin vector (pCLS1107), cutting the GSCO1.4 target, using a high efficiency LiAc transformation protocol. Variant-target yeast strains were used as target strains for mating assays as described in example 4. Positives resulting clones were verified by sequencing (MIL-LEGEN) as described in example 2.

B) Results

The two variants cleaving GSCHO1.3, KRSRES/TYSNI and KRSRES/DYSYQ (I-CreI 30R,33R,38E,44T,68Y,70S, 75N and I-CreI 30R,33R,38E,44D,68Y,70S,75Y,77Q, also called KRSRES/TYSNI, and KRSRES/DYSYQ according to the nomenclature of Table VI), were pooled, randomly mutagenized and transformed into yeast. 2304 transformed clones were then mated with a yeast strain that contains (i) the GSCHO1 target in a reporter plasmid (ii) an expression plasmid containing a variant that cleaves the GSCHO1.4 target (I-CreI 30R,32G,44K,68N or KRGYQS/KNRDI according to the nomenclature of Table VIII). After mating with this yeast strain, 38 clones were found to cleave the GSCHO1 target more efficiently than the original variant. Thus, 38 positives contained proteins able to form heterodimers with KRGYQS/KNRDI with strong cleavage activity for the GSCHO1 target. An example of positives is shown in FIG. 11. Sequencing of these 38 positive clones indicates that 19 distinct variants listed in Table XI were identified.

TABLE XI

Functional variant combinations displaying strong cleavage activity for GSCHO1.

| VARIANT GSCHO1.4 | Optimized* Variants GSCHO1.3 (SEQ ID NO: 211 to 229) |
|---|---|
| I-CreI 28K30R32Y33G38Q 40S44K68N70R75D77I | I-CreI 7E 19A 30R 33R 38E 44D 68Y 70S 75Y 77Q 120A |
| | I-CreI 30R 33R 38E 44D 66H 68Y 70S 75Y 77Q 132V |

TABLE XI-continued

Functional variant combinations
displaying strong cleavage activity for GSCHO1.

Optimized* Variants GSCHO1.3
(SEQ ID NO: 211 to 229)

| (KRYGQS/ICNRDI) | I-CreI 30R 33R 38E 44D 68Y 70S 75Y 77Q 87L |
| --- | --- |
| | I-CreI 30R 33R 38E 43L 44D 68Y 70S 75Y 77Q |
| | I-CreI 19S 30R 33R 38E 44D 57E 68Y 70S 75Y 77Q 118T 132V |
| | I-CreI 24V 30R 33R 38E 44T 68Y 70S 75N 77T 80K 107R |
| | I-CreI 30R 33R 38E 44T 50R 68Y 70S 75N |
| | I-CreI 30R 33R 38E 39V 44D 68Y 70S 75Y 77Q |
| | I-CreI 30R 33R 38E 44D 68Y 70S 75Y 77Q 96R 129A |
| | I-CreI 30R 33R 38E 44D 45L 50R 68Y 70S 75Y 77Q |
| | I-CreI 30R 33R 38E 44D 68Y 70S 75Y 77Q 107R 129A |
| | I-CreI 30R 33R 38E 44D 68Y 70S 75Y 77Q 92R |
| | I-CreI 30R 33R 38E 44D 68Y 70S 75Y 77Q 161P |
| | I-CreI 30R 33R 38E 44D 68Y 70S 75Y 77Q 120E |
| | I-CreI 30R 33R 38E 44D 68Y 70S 75Y 77Q 87L 139R |
| | I-CreI 30R 33R 38E 44D 68Y 70S 75Y 77Q 105A |
| | I-CreI 30R 33R 38E 44D 64A 68Y 70S 75Y 77Q 87I 105A 117V 137N |
| | I-CreI 24V 30R 33R 38E 44D 68Y 70S 75Y 77Q |
| | I-CreI 30R 33R 38E 44T 68Y 70S 75N 132V |

*Mutations resulting from random mutagenesis are in bold.

EXAMPLE 6

Improvement of Meganucleases Cleaving GSCHO1 by Site-directed Mutagenesis of Proteins Cleaving GSCHO1.3 and Assembly with Proteins Cleaving GSCHO1.4

The initial I-CreI variants cleaving GSCHO1.3 described in Table VI and used for random mutagenesis in example 5 were also mutagenized by introducing selected amino-acid substitutions in the proteins and screening for more efficient variants cleaving GSCHO1 in combination with a variant cleaving GSCHO1.4.

Six amino-acid substitutions have been found in previous studies to enhance the activity of I-CreI derivatives: these mutations correspond to the replacement of Glycine 19 with Serine (G19S), Phenylalanine 54 with Leucine (F54L), Glutamic acid 80 with Lysine (E80K), Phenylalanine 87 with Leucine (F87L), Valine 105 with Alanine (V105A) and Isoleucine 132 with Valine (I132V). These mutations were individually introduced into the coding sequence of proteins cleaving GSCHO1.3, and the resulting proteins were tested for their ability to induce cleavage of the GSCHO1 target, upon co-expression with a variant cleaving GSCHO1.4.

A) Material and Methods
a) Site-directed Mutagenesis

Site-directed mutagenesis libraries were created by PCR on a pool of chosen variants. For example, to introduce the G19S substitution into the coding sequence of the variants, two separate overlapping PCR reactions were carried out that amplify the 5' end (residues 1-24) or the 3' end (residues 14-167) of the I-CreI coding sequence. For both the 5' and 3' end, PCR amplification is carried out using a primer with homology to the vector (Gal10F 5'-gcaactttagtgctgacacata-cagg-3' (SEQ ID NO: 186) or Gal10R 5'-acaaccttgattggagact-tgacc-3'(SEQ ID NO: 187)) and a primer specific to the I-CreI coding sequence for amino acids 14-24 that contains the substitution mutation G19S (G19SF 5'-gccggctttgtggactct-gacggtagcatcatc-3' (SEQ ID NO: 230) or G19SR 5'-gatgat-gctaccgtcagagtccacaaagccggc-3'(SEQ ID NO: 231)). The resulting PCR products contain 33 bp of homology with each other. The PCR fragments were purified. Approximately 25 ng of each of the two overlapping PCR fragments and 75 ng of vector DNA (pCLS0542, FIG. 6) linearized by digestion with NcoI and EagI were used to transform the yeast *Saccharomyces cerevisiae* strain FYC2-6A (MATα; trp1Δ63, leu2Δ1, his3Δ200) using a high efficiency LiAc transformation protocol (Gietz and Woods, Methods Enzymol., 2002, 350, 87-96). Intact coding sequences containing the G19S substitution are generated in vivo homologous recombination in yeast.

The same strategy is used with the following pair of oligonucleotides to create other libraries containing the F54L, E80K, F87L, V105A and I132V substitutions, respectively:

```
* F54LF:
                         (SEQ ID NO: 232 and 233)
5'-acccagcgccgttggctgctggacaaactagtg-3'
and F54LR:
5'-cactagtttgtccagcagccaacggcgctgggt-3';

* E80KF:
                         SEQ ID NO: 234 and 235)
5'-ttaagcaaaatcaagccgctgcacaacttcctg-3'
and E80KR:
5'-caggaagttgtgcagcggcttgattttgcttaa-3';
```

```
                            -continued
* F87LF:
                         SEQ ID NO: 236 and 237)
5'-aagccgctgcacaacctgctgactcaactgcag-3'
and F87LR:
5'-ctgcagttgagtcagcaggttgtgcagcggctt-3';

* V105AF:
                         SEQ ID NO: 238 and 239)
5'-aaacaggcaaacctggctctgaaaattatcgaa-3'
and V105AR:
5'-ttcgataattttcagagccaggtttgcctgttt-3';

* I132VF:
                         SEQ ID NO: 240 and 241)
5'-acctgggtggatcaggttgcagctctgaacgat-3'
and I132VR:
5'-atcgttcagagctgcaacctgatccacccaggt-3'.
``` c) Mating of Meganuclease Expressing Clones and Screening in Yeast

The experimental procedure is as described in example 5.

d) Sequencing of Variants

The experimental procedure is as described in example 2.

B) Results

Libraries containing one of six amino-acid substitutions (Glycine 19 with Serine, Phenylalanine 54 with Leucine, Glutamic acid 80 with Lysine, Phenylalanine 87 with Leucine, Valine 105 with Alanine and Isoleucine 132 with Valine) were constructed on a pool of two variants cleaving GSCHO1.3 KRSRES/TYSNI and KRSRES/DYSYQ (I-CreI 30R,33R,38E,44T,68Y,70S,75N and I-CreI 30R,33R,38E, 44D,68Y,70S,75Y,77Q, also called KRSRES/TYSNI, and KRSRES/DYSYQ, respectively, according to the nomenclature of Table VI). 192 transformed clones for each library were then mated with a yeast strain that contains (i) the GSCHO1 target in a reporter plasmid (ii) an expression plasmid containing a variant that cleaves the GSCHO1.4 target (I-CreI 30R,32G,44K,68N or KRGYQS/KNRDI) described in example 3.

After mating with this yeast strain, a large number of clones (>20) in each of the libraries, except for the library containing amino-acid substitution Phenylalanine 54 with Leucine, were found to cleave the GSCHO1 target more efficiently than the original variants. An example of positives is shown in FIG. 12. The sequence of the five best I-CreI variants cleaving the GSCHO1 target when forming a heterodimer with the KRGYQS/KNRDI variant are listed in Table XII.

TABLE XII

Functional variant combinations displaying strong cleavage activity for GSCHO1.

| VARIANT GSCHO1.4 I-CreI | Optimized* Variants GSCHO1.3 (SEQ ID NO: 242 to 244, 213, 226) |
|---|---|
|  | I-CreI 19S 30R 33R 38E 44D 68Y 70S 75Y 77Q |
| 28K30R32Y33G38Q40S | I-CreI 30R 33R 38E 44D 68Y 70S 75Y 77Q 132V |
| 44K68N70R75D77I | I-CreI 30R 33R 38E 44D 68Y 70S 75Y 77Q 80K |
| (KRYGQS/KNRDI) | I-CreI 30R 33R 38E 44D 68Y 70S 75Y 77Q 87L |
|  | I-CreI 30R 33R 38E 44D 68Y 70S 75Y 77Q 105A |

*Mutations resulting from site-directed mutagenesis are in bold.

EXAMPLE 7

Improvement of Meganucleases Cleaving GSCHO1 by Random Mutagenesis of Proteins Cleaving GSCHO1.4 and Assembly with Proteins Cleaving GSCHO1.3

As a complement to example 4 we also decided to perform random mutagenesis with variants that cleave GSCHO1.4. The mutagenized proteins cleaving GSCHO1.4 were then tested to determine if they could efficiently cleave GSCHO1 when co-expressed with a protein cleaving GSCHO1.3.

A) Material and Methods a) Construction of Libraries by Random Mutagenesis

Random mutagenesis was performed on a pool of chosen variants, by PCR using $Mn^{2+}$. PCR reactions were carried out that amplify the I-CreI coding sequence using the primers preATGCreFor (5'-gcataaattactatacttctataga-cacgcaaacacaaatacacacggccttgccacc-3'; SEQ ID NO: 209) and ICreIpostRev (5'-ggctcgaggagctcgtctagag-gatcgctcgagttatcagtcggccgo-3'; SEQ ID NO: 210). Approximately 25 ng of the PCR product and 75 ng of vector DNA (pCLS1107, FIG. 8) linearized by digestion with DraIII and NgoMIV were used to transform the yeast *Saccharomyces cerevisiae* strain FYC2-6A (MATα, trp1Δ63, leu2Δ1, his3Δ200) using a high efficiency LiAc transformation protocol (Gietz and Woods, Methods Enzymol., 2002, 350, 87-96). Expression plasmids containing an intact coding sequence for the I-CreI variant were generated by in vivo homologous recombination in yeast.

b) Variant-target Yeast Strains, Screening and Sequencing

The yeast strain FYBL2-7B (MAT α, ura3Δ851, trp1Δ63, leu2Δ1, lys2Δ202) containing the GSCHO1 target in the yeast reporter vector (pCLS1055, FIG. 5) was transformed with variants, in the leucine vector (pCLS0542), cutting the GSCHO1.3 target, using a high efficiency LiAc transformation protocol. Variant-target yeast strains were used as target strains for mating assays as described in example 4. Positives resulting clones were verified by sequencing (MILLEGEN) as described in example 2.

in a reporter plasmid (ii) an expression plasmid containing a variant that cleaves the GSCHO1.3 target (I-CreI 30R,33R, 38E,44D,68Y,70S,75Y,77Q or KRSRES/DYSYQ according to the nomenclature of table VI). After mating with this yeast strain, 254 clones were found to cleave the GSCHO1 target more efficiently than the original variants. Thus, 254 positives contained proteins able to form heterodimers with KRSRES/DYSYQ with strong cleavage activity for the GSCHO1 target. An example of positives is shown in FIG. 13. Sequencing 32 of the strongest positive clones indicates that 18 distinct variants listed in Table XIII were identified.

TABLE XIII

Functional variant combinations displaying strong cleavage activity for GSCHO1.

| VARIANT GSCHO1.3 | Optimized Variants GSCHO1.4 (SEQ ID NO: 245 to 262) |
|---|---|
| I-CreI 28K30R32S33R38E40S | I-CreI 3A 30R 33R 68A 75D 77R |
| 44D68Y70S75Y77Q | I-CreI 30R 32G 68A 75D 77R 119L |
| (KRSRES/DYSYQ) | I-CreI 19S 30R 32D 44R 68H 75D 161T |
| | I-CreI 30R 32G 44R 68H 75D 132V 154G |
| | I-CreI 2S 30R 33H 68A 75D 77R |
| | I-CreI 30R 33R 68A 75D 77R |
| | I-CreI 30R 33H 68A 75D 77R |
| | I-CreI 30R 32G 44R 68H 75D 125I 132V 160R |
| | I-CreI 30R 33H 68A 75D 77R 114F |
| | I-CreI 12H 30R 32A 33H 45M 68S 75D 77R |
| | I-CreI 30R 33H 60Y 68A 75D 77R |
| | I-CreI 30R 33H 50R 68A 75D 77R |
| | I-CreI 30R 33H 68A 75D 77R 110V 153N |
| | I-CreI 6K 30R 33H 68A 75D 77R 114P |
| | I-CreI 30R 33H 35L 68A 75D 77R |
| | I-CreI 30R 32G 33H 68S 75D 77R 137Y |
| | I-CreI 30R 33H 38H 68A 75D 77R |
| | I-CreI 30R 33H 68T 75D 77R |

* Mutations resulting from random mutagenesis are in bold.
** Variants are derived from the I-CreI N75 scaffold and position 75 was mutated to aspartic acid (D) during cycle of random mutagenesis.

B) Results

Nine variants cleaving GSCHO1.4 (I-CreI 30R,32G,44K, 68Y,70S,75N, I-CreI 33H,38N,44K,47K,68N,70S,75N, I-CreI 30K,33A,75N, I-CreI 30R,32G,44K,59A,68N,70A, 75N, I-CreI 30R,33T,38R,44K,68N,70S,75N, I-CreI 30R, 32G,44K,45M,68Y,70S,75N,77V, I-CreI 30R,32G,44K, 68N,70S,75N, I-CreI 30R,32G,44R,68Y,70S,75N and I-CreI 32A,33H,44K,68P,70S,75N also called KRGYQS/KYSNI, KNSHNS/KNSNI+47K, KKSAQS/QRRNI, KRGYQS/KNANI+59A, KRSTRS/KNSNI, KRGYQS/KYSNV+45M, KRGYQS/KNSNI, KRGYQS/KYSNI and KNAHQS/KPSNI, respectively, according to the nomenclature of Table VII and Table VIII) were pooled, randomly mutagenized and transformed into yeast. 4608 transformed clones were then mated with a yeast strain that contains (i) the GSCHO1 target

EXAMPLE 8

Improvement of Meganucleases Cleaving GSCHO1 by Site-directed Mutagenesis of Proteins Cleaving GSCHO1.4 and Assembly with Proteins Cleaving GSCHO1.3

The initial I-CreI variants cleaving GSCHO1.4 described in Tables 3 and 4 and used for random mutagenesis in example 7 were also mutagenized by introducing selected amino-acid substitutions in the proteins and screening for more efficient variants cleaving GSCHO1 in combination with a variant cleaving GSCHO1.3.

Six amino-acid substitutions have been found in previous studies to enhance the activity of I-CreI derivatives: these mutations correspond to the replacement of Glycine 19 with Serine (G19S), Phenylalanine 54 with Leucine (F54L), Glutamic acid 80 with Lysine (E80K), Phenylalanine 87 with Leucine (F87L), Valine 105 with Alanine (V105A) and Isoleucine 132 with Valine (I132V). These mutations were individually introduced into the coding sequence of proteins cleaving GSCHO1.3, and the resulting proteins were tested for their ability to induce cleavage of the GSCHO1 target, upon co-expression with a variant cleaving GSCHO1.4.

A) Material and Methods a) Site-directed Mutagenesis

Site-directed mutagenesis libraries were created by PCR on a pool of chosen variants. For example, to introduce the G19S substitution into the coding sequence of the variants, two separate overlapping PCR reactions were carried out that amplify the 5' end (residues 1-24) or the 3' end (residues 14-167) of the I-CreI coding sequence. For both the 5' and 3' end, PCR amplification is carried out using a primer with homology to the vector (Gal10F 5'-gcaactttagtgctgacacatacagg-3' or Gal10R 5'-acaaccttgattggagacttgacc-3') and a primer specific to the I-CreI coding sequence for amino acids 14-24 that contains the substitution mutation G19S (G19SF 5'-gccggctttgtggactctgacggtagcatcatc-3' (SEQ ID NO: 230) or G19SR 5'-gatgatgctaccgtcagagtccacaaagccggc-3' (SEQ ID NO: 231)). The resulting PCR products contain 33 bp of homology with each other. The PCR fragments were purified. Approximately 25 ng of each of the two overlapping PCR fragments and 75 ng of vector DNA (pCLS1107, FIG. 8) linearized by digestion with DraIII and NgoMIV were used to transform the yeast *Saccharomyces cerevisiae* strain FYC2-6A (MATα, trp1Δ63, leu2Δ1, his3Δ200) using a high efficiency LiAc transformation protocol (Gietz and Woods, Methods Enzymol., 2002, 350, 87-96). Intact coding sequences containing the G19S substitution are generated by in vivo homologous recombination in yeast.

The same strategy is used with the following pair of oligonucleotides to create other libraries containing the F54L, E80K, F87L, V105A and I132V substitutions, respectively:

```
* F54LF:
                         (SEQ ID NO: 232 and 233)
5'-acccagcgccgttggctgctggacaaactagtg-3'
and F54LR:
5'-cactagtttgtccagcagccaacggcgctgggt-3';

* E80KF:
                         SEQ ID NO: 234 and 235)
5'-ttaagcaaaatcaagccgctgcacaacttcctg-3'
and E80KR:
5'-caggaagttgtgcagcggcttgattttgcttaa-3';

* F87LF:
                         SEQ ID NO: 236 and 237)
5'-aagccgctgcacaacctgctgactcaactgcag-3'
and F87LR:
5'-ctgcagttgagtcagcaggttgtgcagcggctt-3';

* V105AF:
                         SEQ ID NO: 238 and 239)
5'-aaacaggcaaacctggctctgaaaattatcgaa-3'
and V105AR:
5'-ttcgataattacagagccaggtttgcctgttt-3';
```

```
-continued
* I132VF:
                         SEQ ID NO: 240 and 241)
5'-acctgggtggatcaggttgcagctctgaacgat-3'
and I132VR:
5'-atcgttcagagctgcaacctgatccacccaggt-3'.
``` c) Mating of Meganuclease Expressing Clones and Screening in Yeast

The experimental procedure is as described in example 7.

d) Sequencing of Variants

The experimental procedure is as described in example 2.

B) Results

Libraries containing one of six amino-acid substitutions (Glycine 19 with Serine, Phenylalanine 54 with Leucine, Glutamic acid 80 with Lysine, Phenylalanine 87 with Leucine, Valine 105 with Alanine and Isoleucine 132 with Valine) were constructed on a pool of nine variants cleaving GSCHO1.4 (I-CreI 30R,32G,44K,68Y,70S,75N, I-CreI 33H, 38N,44K,47K,68N,70S,75N, I-CreI 30K,33A,75N, I-CreI 30R,32G,44K,59A,68N,70A,75N, I-CreI 30R,33T,38R, 44K,68N,70S,75N, I-CreI 30R,32G,44K,45M,68Y,70S, 75N,77V, I-CreI 30R,32G,44K,68N,70S,75N, I-CreI 30R, 32G,44R,68Y,70S,75N and I-CreI 32A,33H,44K,68P,70S, 75N also called KRGYQS/KYSNI, KNSHNS/KNSNI+47K, KKSAQS/QRRNI, KRGYQS/KNANI+59A, KRSTRS/KN-SNI, KRGYQS/KYSNV+45M, KRGYQS/KNSNI, KRGYQS/RYSNI and KNAHQS/KPSNI, respectively, according to the nomenclature of Table VII and Table VIII). 192 transformed clones for each library were then mated with a yeast strain that contains (i) the GSCHO1 target in a reporter plasmid (ii) an expression plasmid containing a variant that cleaves the GSCHO1.3 target (I-CreI 30R,33R,38E,44D, 68Y,70S,75Y,77Q or KRSRES/DYSYQ) described in example 2.

After mating with this yeast strain, a large number of clones (>20) were found to cleave the GSCHO1 target more efficiently than the original variants for the libraries containing amino-acid substitution Glycine 19 with Serine, Phenylalanine 54 with Leucine and Isoleucine 132 with Valine. An example of positives is shown in FIG. 14. The sequence of the two best I-CreI variants from each library cleaving the GSCHO1 target when forming a heterodimer with the KRSRES/DYSYQ variant are listed in Table XIV. These variants display non parental combinations at positions 28, 30, 32, 33, 38, 40 or 44, 68, 70, 75, 77. Such combinations likely result from PCR induced mutations during the combinatorial process.

TABLE XIV

Functional variant combinations displaying strong cleavage activity for GSCHO1.

| VARIANT GSCHO1.3 | I-CreI 28K30R32S33R38E40S 75D 77R | Optimized* Variants GSCHO1.4 (SEQ ID NO: 263 to 268) I-CreI 19S 30R 33H 68A |
|---|---|---|
| | 44D68Y70S75Y77Q (KRSRES/DYSYQ) | I-CreI 19S 30R 32G 44K 45M 68H 75D |
| | | I-CreI 30R 33H 68A 75D 77R 132V |

TABLE XIV-continued

Functional variant combinations
displaying strong cleavage activity for
GSCHO1.

Optimized* Variants
GSCHO1.4
(SEQ ID NO: 263 to 268)

I-CreI 30R 32G 44R 68H
75D 132V

I-CreI 30R 32G 44R 54L
68H 75D

I-CreI 30R 33T 38R 44K
54L 68H 75D

*Mutations resulting from site-directed mutagenesis are in bold.
** Variants are derived from the I-CreI N75 scaffold and position 75 was mutated aspartic acid (D) during improvement.

EXAMPLE 9

Validation of GSCHO1 Target Cleavage in an Extrachromosomal Model in CHO Cells

I-CreI variants able to efficiently cleave the GSCHO1 target in yeast when forming heterodimers were described in examples 4, 5, 6, 7 and 8. In order to identify heterodimers displaying maximal cleavage activity for the GSCHO1 target in CHO cells, the efficiency of chosen combinations of variants to cut the GSCHO1 target was compared, using an extrachromosomal assay in CHO cells. The screen in CHO cells is a single-strand annealing (SSA) based assay where cleavage of the target by the meganucleases induces homologous recombination and expression of a LagoZ reporter gene (a derivative of the bacterial lacZ gene).

1) Materials and Methods
a) Cloning of GSCHO1 Target in a Vector for CHO Screen

The target was cloned as follows: oligonucleotide corresponding to the GSCHO1 target sequence flanked by gateway cloning sequence was ordered from PROLIGO: 5' tggcatacaagtttctgccccagggtgagaaagtccaacaatcgtctgtca 3' (SEQ ID NO: 202). Double-stranded target DNA, generated by PCR amplification of the single stranded oligonucleotide, was cloned using the Gateway protocol (INVITROGEN) into CHO reporter vector (pCLS1058, FIG. 15). Cloned target was verified by sequencing (MILLEGEN).

b) Re-cloning of Meganucleases

The ORF of I-CreI variants cleaving the GSCHO1.3 and GSCHO1.4 targets identified in examples 3, 5, 6, 7 and 8 were re-cloned in pCLS1768 (FIG. 16). ORFs were amplified by PCR on yeast DNA using the attB1-ICreIFor (5% ggggacaagtttgtacaaaaaagcaggcttcgaaggagatagaaccatggccaataccaaatataacaaagagttcc-3'; SEQ ID NO: 269) and attB2-ICreIRev (5'-ggggaccactttgtacaagaaagctgggtttagtcggccgccggggaggatttcttcttctcgc-3'; SEQ ID NO: 270) primers. PCR products were cloned in the CHO expression vector pCLS1768 (FIG. 16) using the Gateway protocol (INVITROGEN). Resulting clones were verified by sequencing (MILLEGEN).

c) Extrachromosomal Assay in Mammalian Cells

CHO cells were transfected with Polyfect® transfection reagent according to the supplier's protocol (QIAGEN). 72 hours after transfection, the level of Beta galactosidase expression for each transfection was quantified using the Beta-Glo® Assay System (Promega). The Beta-Glo Assay contains a luciferin-galactoside substrate (6-O-β-galactopyranosylluciferin) that can be cleaved by β-galactosidase to form luciferin that is then utilized in a firefly luciferase reaction to generate light. For each transfection, approximately 100,000 cells in 100 µl of medium were combined with an equal volume of Beta-Glo lysis/revelation buffer as described by the manufacturer (Promega). After 30 minutes of incubation at room temperature, signal was measured with a luminometer (Perkin Elmer Victor multilabel plate reader).

Per assay, 150 ng of target vector was cotransfected with 25 ng of each one of both variants (25 ng of variant cleaving palindromic GSCHO1.3 target and 25 ng of variant cleaving palindromic GSCHO1.4 target).

2) Results

Several variants described in examples 3, 5, 6, 7 and 8 were first recloned in pCLS1768 (FIG. 16). Then, in order to identify the heterodimer displaying the maximal cleavage activity with the GSCHO1 target in CHO cells, I-CreI variants cleaving the GSCHO1.3 or GSCHO1.4 targets (described in examples 3, 5, 6, 7 and 8) were tested together as heterodimers against the GSCHO1 target in the CHO extrachromosomal assay.

FIG. 17 shows the results obtained for 12 heterodimers tested and the values of the different combinations are compiled in Table XV. Analysis of the efficiencies of cleavage of the GSCHO1 sequence demonstrates that 10 of the 12 combinations of I-CreI variants are able to efficiently cut the GSCHO1 target in CHO cells.

TABLE XV

Functional heterodimeric combinations cutting the GSCHO1 target in CHO cells.

|  |  | Optimized variants cleaving GSCHO1.3 | | |
| --- | --- | --- | --- | --- |
|  |  | Mt 3A<br>30R 33R 38E 44D 66H<br>68Y 70S 75Y 77Q 132V<br>(SEQ ID NO: 212) | Mt 3B<br>19A 30R 33R 38E<br>44D 68Y 70S 75Y<br>77Q 120A<br>(SEQ ID NO: 271) | Mt 3C<br>19S 30R 33R 38E 44D<br>57E 68Y 70S 75Y 77Q<br>118T 132V<br>(SEQ ID NO: 215) |
| Optimized variants<br>cleaving GSCHO1.4 | Mt 4A<br>19S 30R<br>32G 44K<br>45M 68H<br>(SEQ ID<br>NO: 264) | $2.8 \times 10^6$ | $0.5 \times 10^6$ | $0.04 \times 10^6$ |

TABLE XV-continued

Functional heterodimeric combinations cutting the GSCHO1 target in CHO cells.

| | Optimized variants cleaving GSCHO1.3 | | |
|---|---|---|---|
| | Mt 3A<br>30R 33R 38E 44D 66H<br>68Y 70S 75Y 77Q 132V<br>(SEQ ID NO: 212) | Mt 3B<br>19A 30R 33R 38E<br>44D 68Y 70S 75Y<br>77Q 120A<br>(SEQ ID NO: 271) | Mt 3C<br>19S 30R 33R 38E 44D<br>57E 68Y 70S 75Y 77Q<br>118T 132V<br>(SEQ ID NO: 215) |
| Mt 4B<br>30R 32G<br>68A 77R<br>119L<br>(SEQ ID<br>NO: 246) | $2.3 \times 10^6$ | $3.1 \times 10^6$ | $2.8 \times 10^6$ |
| Mt 4C<br>30R 33R<br>68A 77R<br>(SEQ ID<br>NO: 250) | $2.0 \times 10^6$ | $3.1 \times 10^6$ | $2.9 \times 10^6$ |
| Mt 4D<br>30R 32G<br>44R 68H<br>(SEQ ID<br>NO: 130) | $2.5 \times 10^6$ | $3.1 \times 10^6$ | $2.4 \times 10^6$ |

The invention claimed is:

1. A method of cleaving a DNA target sequence from a glutamine synthetase gene comprising contacting said DNA target sequence with an I-CreI variant to thereby cleave said DNA target sequence wherein said I-CreI variant comprises a first monomer and a second monomer which are associated to form an active form, wherein said I-CreI variant comprises at least two substitutions in at least one of the monomers, said first monomer has a sequence that is at least 97% identical to SEQ ID NO: 271 and said second monomer has a sequence that is at least 97% identical to SEQ ID NO: 246 and wherein said DNA target sequence is SEQ ID NO: 30.

2. The method of claim 1, wherein said variant is a single-chain chimeric meganuclease comprising two I-CreI monomers.

3. The method of claim 1, wherein said contacting is in a cell.

4. The method of claim 1, wherein said I-CreI variant is expressed in a cell from a polynucleotide encoding said I-CreI variant.

5. The method of claim 1, wherein the cleavage of the DNA target sequence leads to a glutamine synthetase knock-out cell line.

6. The method of claim 1, further comprising insertion of a transgene at the locus of the DNA target sequence in the glutamine synthetase gene.

7. A method of cleaving a DNA target sequence from a glutamine synthetase gene comprising contacting said DNA target sequence with an I-CreI variant to thereby cleave said DNA target sequence
wherein said I-CreI variant comprises a first monomer and a second monomer which are associated to form an active form,
wherein said I-CreI variant comprises at least two substitutions in at least one of the monomers, wherein at least one substitution is of a residue in the range of positions 28 to 40 of I-CreI and at least one substitution is of a residue in the range of positions 44 to 77 of I-CreI and
wherein said variant is a heterodimer, resulting from the association of a first and a second monomer having different mutations in positions 28 to 40 and 44 to 77 of I-CreI and wherein the first monomer and the second monomer, respectively, are selected from the following pairs of sequences:
(i) one of SEQ ID NO: 61 to 84 (first monomer) and one of SEQ ID NO: 85 to 108 (second monomer);
(ii) one of SEQ ID NO: 63 and 109 to 128 (first monomer) and one of SEQ ID NO: 89 and 129 to 151 (second monomer); and
(iii) one of SEQ ID NO: 63, 109, 110, 113, 123, 127, and 152 to 163 (first monomer) and one of SEQ ID NO: 89, 130 to 134, 136, 146, 147, 164 to 175, 198-200, 203, and 206 to 208 (second monomer).

8. The method of claim 7, wherein said variant is a single-chain chimeric meganuclease comprising two I-CreI monomers.

9. The method of claim 7, wherein the cleavage of the DNA target sequence leads to a glutamine synthetase knock-out cell line.

10. The method of claim 7, further comprising insertion of a transqene at the locus of the DNA target sequence in the glutamine synthetase gene.

11. A method of cleaving a DNA target sequence from a glutamine synthetase gene comprising contacting said DNA target sequence with an I-CreI variant to thereby cleave said DNA target sequence
wherein said I-CreI variant comprises a first monomer and a second monomer which are associated to form an active form,
wherein said I-CreI variant comprises at least two substitutions in at least one of the monomers,
wherein at least one substitution is of a residue in the range of positions 28 to 40 of I-CreI and at least one substitution is of a residue in the range of positions 44 to 77 of I-CreI and
wherein said variant is a heterodimer, resulting from the association of a first and a second monomer having different mutations in positions 28 to 40 and 44 to 77 of I-CreI and
wherein at least one of the two I-CreI monomers has at least 95% sequence identity with one of the sequences selected from the group consisting of: SEQ ID NO: 61-136, 138-144, 147-175, 198-200, 203, and 206-208.

12. The method of claim 11, wherein said variant is a single-chain chimeric meganuclease comprising two I-CreI monomers.

13. The method of claim 11, wherein the cleavage of the DNA target sequence leads to a glutamine synthetase knock-out cell line.

14. The method of claim 11, further comprising insertion of a transqene at the locus of the DNA target sequence in the glutamine synthetase gene.

15. A method of cleaving a DNA target sequence from a glutamine synthetase gene comprising contacting said DNA target sequence with an I-CreI variant to thereby cleave said DNA target sequence
wherein said I-CreI variant comprises a first monomer and a second monomer which are associated to form an active form,
wherein said I-CreI variant comprises at least two substitutions in at least one of the monomers,
wherein at least one substitution is of a residue in the range of positions 28 to 40 of I-CreI and at least one substitution is of a residue in the range of positions 44 to 77 of I-CreI and
wherein said target sequence is SEQ ID NO: 30 and
wherein said I-CreI variant comprises a first monomer having any of SEQ ID NO: 211 to 229, 242 to 244 and 271 and a second monomer having any of SEQ ID NO: 245 to 268.

16. The method of claim 15, wherein said variant is a single-chain chimeric meganuclease comprising two I-CreI monomers.

17. The method of claim 15, wherein the cleavage of the DNA target sequence leads to a glutamine synthetase knock-out cell line.

18. The method of claim 15, further comprising insertion of a transgene at the locus of the DNA target sequence in the glutamine synthetase gene.

19. A method of cleaving a DNA target sequence from a glutamine synthetase gene comprising contacting said DNA target sequence with an I-CreI variant to thereby cleave said DNA target sequence
wherein said I-CreI variant comprises a first monomer and a second monomer which are associated to form an active form,
wherein said I-CreI variant comprises at least two substitutions in at least one of the monomers,
wherein at least one substitution is of a residue in the range of positions 28 to 40 of I-CreI and at least one substitution is of a residue in the range of positions 44 to 77 of I-CreI and
wherein said target sequence is SEQ ID NO: 30 and
wherein said I-CreI variant comprises a first monomer having at least 97% sequence identity with one of the sequences selected from the group consisting of: SEQ ID NO: 211 to 229, 242 to 244 and 271, and a second monomer having at least 97% sequence identity with one of the sequences selected from the group consisting of: SEQ ID NO: 245 to 268.

20. The method of claim 19, wherein said variant is a single-chain chimeric meganuclease comprising two I-CreI monomers.

21. The method of claim 19, wherein the cleavage of the DNA target sequence leads to a glutamine synthetase knock-out cell line.

22. The method of claim 19, further comprising insertion of a transgene at the locus of the DNA target sequence in the glutamine synthetase gene.

23. A method of cleaving a DNA target sequence from a glutamine synthetase gene comprising contacting said DNA target sequence with an I-CreI variant to thereby cleave said DNA target sequence
   wherein said I-CreI variant comprises a first monomer and a second monomer which are associated to form an active form,
   wherein said first monomer having has the sequence of SEQ ID NO: 271, and said second monomer having has the sequence of SEQ ID NO: 246, and
   wherein said DNA target sequence is SEQ ID NO: 30.

24. The method of claim 23, wherein said variant is a single-chain chimeric meganuclease comprising two I-CreI monomers.

25. The method of claim 23, wherein the cleavage of the DNA target sequence leads to a glutamine synthetase knock-out cell line.

26. The method of claim 23, further comprising insertion of a transgene at the locus of the DNA target sequence in the glutamine synthetase gene.

27. A method of cleaving a DNA target sequence from a glutamine synthetase gene comprising contacting said DNA target sequence with an I-CreI variant to thereby cleave said DNA target sequence
   wherein said I-CreI variant comprises a first monomer and a second monomer which are associated to form an active form,
   wherein said first monomer has a sequence that is at least 97% identical to one of the sequences selected from the group consisting of SEQ ID NO: 212, 215, and 271, and said second monomer has a sequence that is at least 97% identical to one of the sequences selected from the group consisting of SEQ ID NO: 130, 246, 250, and 264, and
   wherein said DNA target sequence is SEQ ID NO: 30.

28. The method of claim 27, wherein said first monomer has a sequence selected from the group consisting of SEQ ID NO: 212, 215, and 271, and said second monomer has a sequence selected from the group consisting of SEQ ID NO: 130, 246, 250, and 264.

29. The method of claim 27, wherein said variant is a single-chain chimeric meganuclease comprising two I-CreI monomers.

30. The method of claim 27, wherein the cleavage of the DNA target sequence leads to a glutamine synthetase knock-out cell line.

31. The method of claim 27, further comprising insertion of a transqene at the locus of the DNA target sequence in the glutamine synthetase gene.

* * * * *